(12) United States Patent
Nishio et al.

(10) Patent No.: US 8,883,434 B2
(45) Date of Patent: Nov. 11, 2014

(54) MUTANT ENZYME AND APPLICATION THEREOF

(75) Inventors: Kyoichi Nishio, Kakamigahara (JP); Satoshi Koikeda, Kakamigahara (JP)

(73) Assignee: Amano Enzyme Inc., Nagoya-shi (JP)

( * ) Notice: Subject to any disclaimer, the term of this patent is extended or adjusted under 35 U.S.C. 154(b) by 76 days.

(21) Appl. No.: 13/513,680

(22) PCT Filed: Nov. 22, 2010

(86) PCT No.: PCT/JP2010/070761
§ 371 (c)(1),
(2), (4) Date: Jun. 4, 2012

(87) PCT Pub. No.: WO2011/068050
PCT Pub. Date: Jun. 9, 2011

(65) Prior Publication Data
US 2012/0244565 A1 Sep. 27, 2012

(30) Foreign Application Priority Data
Dec. 5, 2009 (JP) ................................ 2009-277096

(51) Int. Cl.
| | | |
|---|---|---|
| *C12Q 1/54* | (2006.01) | |
| *C12N 9/04* | (2006.01) | |
| *C12P 21/06* | (2006.01) | |
| *C12P 19/34* | (2006.01) | |
| *C12N 15/00* | (2006.01) | |
| *C12N 1/20* | (2006.01) | |
| *C12N 1/00* | (2006.01) | |
| *C07H 21/04* | (2006.01) | |
| *C07K 1/00* | (2006.01) | |

(52) U.S. Cl.
CPC ... *C12Y 101/9901* (2013.01); *C12Y 101/03004* (2013.01); *C07K 2319/21* (2013.01); *C12N 9/0006* (2013.01)
USPC ........... 435/14; 435/190; 435/69.1; 435/91.1; 435/320.1; 435/252.3; 435/254.11; 536/23.1; 536/23.2; 530/350

(58) Field of Classification Search
USPC ........... 435/14, 190, 69.1, 91.1, 320.1, 252.3, 435/254.11; 536/23.1, 23.2; 530/350
See application file for complete search history.

(56) References Cited

U.S. PATENT DOCUMENTS

| | | | |
|---|---|---|---|
| 7,553,649 B2 * | 6/2009 | Tsuji et al. ................. | 435/190 |
| 7,816,025 B2 * | 10/2010 | Kubo et al. ................ | 429/437 |
| 2006/0063217 A1 | 3/2006 | Omura et al. | |
| 2009/0181408 A1 | 7/2009 | Tanaka et al. | |

FOREIGN PATENT DOCUMENTS

| | | |
|---|---|---|
| JP | 09-506249 A | 6/1997 |
| JP | 2000-350588 A | 12/2000 |
| JP | 2001-197888 A | 7/2001 |
| JP | 2001-346587 A | 12/2001 |
| JP | 2008-237210 A | 10/2008 |
| JP | 2009-159964 A | 7/2009 |
| JP | 2009-225800 A | 10/2009 |
| JP | 2009-225801 A | 10/2009 |
| WO | WO-95/14784 A1 | 6/1995 |
| WO | WO-2004/058958 A1 | 7/2004 |
| WO | WO-2007/139013 A1 | 12/2007 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*

(Continued)

*Primary Examiner* — Ganapathirama Raghu
(74) *Attorney, Agent, or Firm* — Edwards Wildman Palmer LLP

(57) ABSTRACT

An object is to provide a novel enzyme that exhibits glucose dehydrogenase activity. Furthermore, another object is to provide a novel method pertaining to enzyme modification. Provided is a mutated enzyme containing an amino acid sequence wherein one or at least two amino acids selected from the group consisting of (1) to (13) are substituted with another amino acid in the amino acid sequence of a microorganism-derived glucose oxidase: (1) the amino acid corresponding to the amino acid at position 115 of the amino acid sequence of SEQ ID NO: 1; (2) the amino acid corresponding to the amino acid at position 131 of the amino acid sequence of SEQ ID NO: 1; (3) the amino acid corresponding to the amino acid at position 132 of the amino acid sequence of SEQ ID NO: 1; (4) the amino acid corresponding to the amino acid at position 193 of the amino acid sequence of SEQ ID NO: 1; (5) the amino acid corresponding to the amino acid at position 353 of the amino acid sequence of SEQ ID NO: 1; (6) the amino acid corresponding to the amino acid at position 436 of the amino acid sequence of SEQ ID NO: 1; (7) the amino acid corresponding to the amino acid at position 446 of the amino acid sequence of SEQ ID NO: 1; (8) the amino acid corresponding to the amino acid at position 472 of the amino acid sequence of SEQ ID NO: 1; (9) the amino acid corresponding to the amino acid at position 511 of the amino acid sequence of SEQ ID NO: 1; (10) the amino acid corresponding to the amino acid at position 535 of the amino acid sequence of SEQ ID NO: 1; (11) the amino acid corresponding to the amino acid at position 537 of the amino acid sequence of SEQ ID NO: 1; (12) the amino acid corresponding to the amino acid at position 582 of the amino acid sequence of SEQ ID NO: 1; and (13) the amino acid corresponding to the amino acid at position 583 of the amino acid sequence of SEQ ID NO: 1.

21 Claims, 15 Drawing Sheets

(56) References Cited

OTHER PUBLICATIONS

Seffernick et al., Melamine deaminase and Atrazine chlorohydrolase: 98 percent identical but functionally different. J. Bacteriol., 2001, vol. 183 (8): 2405-2410.*

Whisstock et al., Prediction of protein function from protein sequence. Q. Rev. Biophysics., 2003, vol. 36 (3): 307-340.*

Witkowski et al., Conversion of b-ketoacyl synthase to a Malonyl Decarboxylase by replacement of the active cysteine with glutamine. Biochemistry, 1999, vol. 38: 11643-11650.*

Supplementary European Search Report dated May 14, 2013, issued for the European Patent Application No. 10 83 4502.6.

Guo, Y. et al., "Cloning and heterologous expression of glucose oxidase gene from *Aspergillus niger* Z-25 in *Pichia pastoris*", Appl Biochem Biotechnol, vol. 162, No. 2, Sep. 27, 2010, pp. 498-509.

Database UniProt [Online] Sep. 5, 2006, "SubName: Full=Glucose oxidase; EC=1.1.3.4; Flags: Fragment", XP002696019, retrieved from EBI accession No. UniPort:QOPGS3.

Zhu, Z. et al., "Making glucose oxidase fit for biofuel cell applications by directed protein evolution", Biosensors and Bioelectronics, vol. 21, No. 11, May 15, 2006, pp. 2046-2051.

Zhu, Z. et al., "Directed evolution of glucose oxidase from *Aspergillus niger* for ferrocenemethanol-mediated electron transfer", Biotechnology Journal, vol. 2, No. 2, Feb. 1, 2007, pp. 241-248.

Witt, S. et al., "Conserved arginine-516 of *Penicillium amagasakiense* glucose oxidase is essential for the efficient binding of β-D glucose", Biochemical Journal, The Biochemical Society, vol. 347, Jan. 1, 2000, pp. 553-559.

Yamaoka, H. et al., "Site directed mutagenesis studies of FAD-dependent glucose dehydrogenase catalytic subunit of *Burkholderia cepacia*", Biotechnology Letters, vol. 30, No. 11, Jun. 26, 2008, pp. 1967-1972.

Wohlfahrt, G. et al., "1.8 and 1.9 Å resolution structures of the *Penicillium amagasakiense* and *Aspergillus niger* glucose oxidases as a basis for modelling substrate complexes", ACTA Crystallographica Section D: Biological Crystallography, vol. 55, No. 5, May 1, 1999, pp. 969-977.

Hecht, H. J. et al., "Crystal structure of glucose oxidase from *Aspergillus niger* refined at 2•3 Å resolution", Journal of Molecular Biology, Academic Press, vol. 229, No. 1, Jan. 5, 1993, pp. 153-172.

Cavener, D. R. et al., "GMC oxidoreductases—A newly defined family of homologous proteins with diverse catalytic activities", Journal of Molecular Biology, vol. 223, No. 3, Feb. 5, 1992, pp. 811-814.

Horaguchi, Y. et al., "Construction of mutant glucose oxidases with increased dye-mediated dehydrogenase activity", International Journal of Molecular Sciences, vol. 13, No. 11, 2012, pp. 14149-14157.

T.G. Bak et al., "Studies on the Glucose Dehydrogenase of *Aspergillus oryzae*," Biochim. Biophys. Acta, 139, 1967, pp. 265-276.

T.G. Bak, "Studies on Glucose Dehydrogenase of *Aspergillus oryzae*," Biochim. Biophys. Acta, 139, 1967, pp. 277-293.

T.G. Bak, "Studies on Glucose Dehydrogenase of *Aspergillus oryzae*," Biochim. Biophys. Acta, 146, 1967, pp. 317-327.

T.G. Bak et al., "Studies on Glucose Dehydrogenase of *Aspergillus oryzae*," Biochim. Biophys. Acta, 146, 1967, pp. 328-335.

Y. Nakajima et al., "FAD Izonsei Glucose Dassuiso Koso no X-sen Kesshogakuteki Kenkyu", 26Q-pm115, Abstracts of "The 129th Annual Meeting of the Pharmaceutical Society of Japan," vol. 3, 2009, p. 118.

Y. Nakajima et al., "FAD Izonsei Glucose Dassuiso Koso no Kessho Kozo", 3T5a-5 (3P-109), Program and Abstracts of "The 82nd Annual Meeting of the Japanese Biochemical Society," 2009, (1 sheet).

Y. Guo et al., "Cloning and heterologous expression of glucose oxidase gene from *Aspergillus niger* Z-25 in *Pichia pastoris*," Appl Biochem Biotechnol, 162, 2010, pp. 498-509.

H. J. Hecht et al., "Crystal structure of glucose oxidase from *Aspergillus niger* refined at 2.3 Å resolution," J. Mol. Biol., 229, 1993, pp. 153-172.

International Search Report dated Dec. 28, 2010, issued for PCT/JP2010/070761.

Communication in European Patent Application 10 834 502.6-1406, mailed Dec. 16, 2013.

* cited by examiner

```
FAD-GDH(P. italicum)         PTYGESLQRKGGGLKFESKKTYSTHKGSSYPAYPSAKQLFPNSTALGAD  379
FAD-GDH(P. lilacinoechinulatum) PTIGESLQRKGGGLAYTSKKNYT--KAASYAYPSAEELFTNATTIGAQ  377
FAD-GDH(A. oryzae)           PTYGESLQRKFNGMAGESRGVLA----GASYYTPSIEIDTGNETDSIYA  376
FAD-GDH(A. terreus)          PTYGESLQRKAYGHRDASGKTSIS-----GTKAVSYPDVIDFYGDEAESVAK  372
GO(A. niger)                 P-YGLNLQGQTTSTVKERITSAGAG---GQQAANFATFNETFGDYAEKAHE  369
                                            5

FAD-GDH(P. italicum)         LLR-KLPAYAAGVASANGNITRAABHIREPFKIQSDLIFKREIPYAEILLS  428
FAD-GDH(P. lilacinoechinulatum) LLP-KLPAYAAGVASASGNYTRAABIEEPFKIQSDLIFKSHIPYAERLLE  426
FAD-GDH(A. oryzae)           SLRSGLSDYAAATVRYSNGBRRQRDLERLYGLGFSLIYKDRYPIAEILPR  425
FAD-GDH(A. terreus)          QIRANLKQYAAPTARANGNIRKAADLERLFEVQTRLIPKGRYPLAEVLNY  423
GO(A. niger)                 LLNTRLEQMAREAVARKG-FRNTTALLIQYENYRNWIYKDNVAYSELRLD  408
                                                                               6

FAD-GDH(P. italicum)         G-SGASYSGGYVGSYPFSRESVBLSSADP-TAAPTIDFKYPELDFDLRAQ  476
FAD-GDH(P. lilacinoechinulatum) P-FGFTYRGEYVGSYPFSRESTBISSSDP-TRPAIIDFKYPELDFDFRAQ  474
FAD-GDH(A. oryzae)           PGGERAVSSGWELLYFARKNTHIGSSDP-TRPAAINPNTPMELRDGKSQ  474
FAD-GDH(A. terreus)          PSSATSYPAGWALLFAMESYHIGSSNP-AEFPVINPNTPMELDMDAKSY  472
GO(A. niger)                 T---AGYASFDYWDLLPFTRGYYHILDKDFYLRFAYDPQRYLSELRLLGQ  456
                                            7                     8

FAD-GDH(P. italicum)         AQAARFIRELFKTEPLARTAGAETTPGLSTYA&GAIREA&SKFTYSK-YR  525
FAD-GDH(P. lilacinoechinulatum) VEAARFIRELFKTEPFADMAGAETSPGLSAVSSNAEHEGRSSFLKSN-FR  523
FAD-GDH(A. oryzae)           AGIAKYIRKILKSAPLNELIAKETKPGLSEIPATAADERKYVERLKAN-YR  523
FAD-GDH(A. terreus)          VAVAKYIRESFESYPLS-GIYKESTPGSYDVIPRKAEERSKERVFIRKNYR  521
GO(A. niger)                 AAATQLARNISSSGAKGTYPAGETIPG-IRLAYDADLSARVEYIPYIR-FR  534
                                                         9

FAD-GDH(P. italicum)         SNYIPTTAGKLFRELGGVVDTRLRYGTSSVRVVDASVNFTQGCSHLQS  573
FAD-GDH(P. lilacinoechinulatum) SNYIPTTAGREFREIGGVVDTRLRYGTSSVRVVDASYIPFQGCSHLQS  573
FAD-GDH(A. oryzae)           SNYHPVGTAAMRFRSIGGVVDHRLRVYGTSNVRVVDASVLFFQGCGHLYS  573
FAD-GDH(A. terreus)          SNYHPVGTAAMRREIGGVYDERLNVYGTTNSVRVVDASVLFFQGCGHLYS  571
GO(A. niger)                 PNYHGVGTCSMMFKDHGGVVHSAARVYGVQGLRVVIKSIFPTQGSSHVI  584
                             10 11                                              12 13

FAD-GDH(P. italicum)         TYYAVAERAABHIKGEL------  593   (SEQ ID NO:3)
FAD-GDH(P. lilacinoechinulatum) TIYAVAERAABHIKAQM------  590  (SEQ ID NO:4)
FAD-GDH(A. oryzae)           TLYAVAERAASDLIKEDAKSA-   593   (SEQ ID NO:5)
FAD-GDH(A. terreus)          TLYAVAERAABLIKABAGRE--   591   (SEQ ID NO:6)
GO(A. niger)                 VFYSMALKVADAILASVAQAQ    605   (SEQ ID NO:1)
```

| # | ID | GDH | GO | GDH/GO |
|---|---|---|---|---|
| 1 | 1-1-16 | 0.113 | 0.115 | 1.0 |
| 2 | 2-1-6 | 0.015 | 0.004 | 3.8 |
| 3 | 2-1-28 | 0.003 | 0.004 | 0.7 |
| 4 | 3-1-26 | 0.178 | 0.032 | 5.6 |
| 5 | 3-1-32 | 0.215 | 0.206 | 1.0 |
| 6 | 3-2-26 | 0.799 | 0.131 | 6.0 |
| 7 | 5-1-6 | 0.185 | 0.076 | 2.4 |
| 8 | 5-1-8 | 0.016 | 0.006 | 2.7 |
| 9 | 5-1-9 | 0.196 | 0.187 | 1.0 |
| 10 | 5-1-10 | 0.026 | 0.01 | 2.6 |
| 11 | 5-1-23 | 0.077 | 0.028 | 2.8 |
| 12 | 5-1-25 | 0.033 | 0.014 | 2.4 |
| 13 | 5-1-44 | 0.389 | 0.164 | 2.4 |
| 14 | 5-1-45 | 0.036 | 0.014 | 2.6 |
| 15 | 5-2-3 | 0.002 | 0.005 | 0.4 |
| 16 | 5-2-4 | 0.036 | 0.013 | 2.8 |
| 17 | 7-1-7 | 0.257 | 0.036 | 7.1 |
| 18 | 7-1-16 | 0.068 | 0.02 | 3.4 |
| 19 | 7-2-17 | 0.329 | 0.072 | 4.6 |
| 20 | 7-2-21 | 0.099 | 0.026 | 3.8 |
| 21 | 7-2-22 | 0.095 | 0.027 | 3.5 |
| 22 | 7-2-28 | 0.091 | 0.028 | 3.3 |
| 23 | 7-2-30 | 0.352 | 0.052 | 6.8 |
| 24 | 7-2-33 | 0.111 | 0.036 | 3.1 |
| 25 | 7-2-34 | 0.024 | 0.011 | 2.2 |
| 26 | 7-2-38 | 0.083 | 0.024 | 3.5 |
| 27 | 7-2-40 | 0.021 | 0.01 | 2.1 |
| 28 | 7-2-42 | 0.295 | 0.038 | 7.8 |
| 29 | 7-2-47 | 0.095 | 0.025 | 3.8 |
| 30 | 8-1-7 | 0.051 | 0.054 | 0.9 |
| 31 | 8-2-16 | -0.003 | 0.004 | -0.8 |
| 32 | 9-2-46 | 0.053 | 0.039 | 1.4 |
| 33 | 10-1-9 | -0.005 | 0.005 | -1.0 |
| 34 | 10-1-28 | -0.006 | 0.005 | -1.2 |
| 35 | 10-1-32 | -0.002 | 0.004 | -0.5 |
| 36 | 10-1-42 | 0.011 | 0.008 | 1.4 |
| 37 | 10-1-47 | 0.006 | 0.006 | 1.0 |
| 38 | 10-2-5 | 0.006 | 0.004 | 1.5 |
| 39 | 10-2-6 | 0.007 | 0.005 | 1.4 |
| 40 | 10-2-7 | 0.006 | 0.005 | 1.2 |
| 41 | 10-2-33 | 0.002 | 0.006 | 0.3 |
| 42 | 12-1-8 | 0.01 | 0.007 | 1.4 |
| 43 | 12-1-40 | 0.011 | 0.008 | 1.4 |
| 44 | 12-1-45 | 0.057 | 0.03 | 1.9 |
| 45 | 12-1-49 | 0.194 | 0.031 | 6.3 |
| 46 | 12-2-24 | 0.101 | 0.018 | 5.6 |
| 47 | 12-2-45 | 0.064 | 0.023 | 2.8 |
| 48 | 13-2-9 | 0.01 | 0.006 | 1.7 |
| 49 | 13-2-47 | 0.064 | 0.089 | 0.7 |
| 50 | pYES-GO | 0.166 | 0.256 | 0.6 |
| 51 | pYES2 | 0 | 0.005 | 0.0 |
| GO"Amano"2 | GO | 0.156 | 0.257 | 0.6 |
| GDH"Amano"3 | FAD-GDH | 1.896 | 0.003 | 632.0 |

FIG. 6

| | |
|---|---|
| 3-1-26 | T132V |
| 3-2-26 | T132A |
| 5-1-5 | T353A T353H |
| 5-1-9 | T353A |
| 5-1-44 | T353A |
| 7-1-7 | D446H |
| 7-2-17 | D446S D446H |
| 7-2-30 | D446H |
| 7-2-42 | D446H D446R |
| 12-1-49 | V582S |

FIG. 8

| | | | | | | | | | | | | | |
|---|---|---|---|---|---|---|---|---|---|---|---|---|---|
| A. niger (SEQ ID NO: 1) | L116 | G131 | T132 | Y193 | T363 | F436 | D446 | Y472 | I531 | P535 | T537 | V582 | M603 |
| P. janthinellum (SEQ ID NO: 2) | M116 | D131 | S132 | V193 | T363 | F436 | G446 | M472 | L531 | P535 | M637 | V582 | M603 |
| P. italicum (SEQ ID NO: 3) | I109 | M118 | A117 | L170 | M341 | L420 | E427 | M463 | T501 | S506 | V508 | L573 | G574 |
| P. blaconeochantalum (SEQ ID NO: 4) | T100 | M118 | V117 | L170 | M341 | L424 | E435 | M480 | S499 | G504 | F506 | L571 | G572 |
| A. oryzae (SEQ ID NO: 5) | V101 | M117 | A118 | L178 | M340 | L423 | E435 | M488 | S499 | G504 | F506 | L571 | G578 |
| A. terreus (SEQ ID NO: 6) | V100 | M116 | A117 | L577 | M339 | L422 | E433 | M459 | Y499 | G522 | F524 | L569 | V570 |

*FIG. 10*

| # | Sample | T132A | T35SA | D446H | V582S | GO assay Measured values | GO assay ΔABS | GDH assay Measured values | GDH assay ΔABS | GDH/GO |
|---|---|---|---|---|---|---|---|---|---|---|
| 1 | pYES-GO-M-1 | O | | | | 0.099 | 0.098 | 0.586 | 0.570 | 5.8 |
| 2 | pYES-GO-M-2 | | | | | 0.072 | 0.071 | 0.195 | 0.179 | 2.5 |
| 3 | pYES-GO-M-3 | | O | | | 0.016 | 0.015 | 0.215 | 0.199 | 13.3 |
| 4 | pYES-GO-M-4 | | | O | | 0.027 | 0.026 | 0.275 | 0.259 | 10.0 |
| 5 | pYES-GO-M-5 | | O | | | 0.037 | 0.036 | 0.208 | 0.192 | 5.3 |
| 6 | pYES-GO-M-6 | O | | | | 0.013 | 0.012 | 0.217 | 0.201 | 16.8 |
| 7 | pYES-GO-M-7 | O | O | O | O | 0.013 | 0.012 | 0.746 | 0.730 | 60.8 |
| 8 | pYES-GO-M-8 | | | | | 0.020 | 0.019 | 0.172 | 0.156 | 8.2 |
| 9 | pYES-GO-M-9 | | O | | | 0.013 | 0.012 | 0.281 | 0.265 | 22.1 |
| 10 | pYES-GO-M-10 | O | O | O | O | 0.007 | 0.006 | 0.270 | 0.254 | 42.3 |
| 11 | pYES-GO-M-11 | O | | | | 0.008 | 0.007 | 0.093 | 0.077 | 11.0 |
| 12 | pYES-GO-M-12 | | O | O | O | 0.008 | 0.007 | 0.186 | 0.170 | 24.3 |
| 13 | pYES-GO-M-13 | O | O | O | O | 0.003 | 0.002 | 0.126 | 0.110 | 55.0 |
| 14 | pYES-GO-M-14 | O | O | | O | 0.006 | 0.005 | 0.133 | 0.117 | 23.4 |
| 15 | pYES-GO-M-15 | | O | | O | 0.003 | 0.002 | 0.064 | 0.048 | 24.0 |
| 16 | pYES-GO-3 | | | | | 0.173 | 0.172 | 0.093 | 0.077 | 0.4 |
| 17 | pYES2 | | | | | 0.001 | 0.000 | 0.036 | 0.020 | — |
| 18 | 0.02u/mL GO-2 | | | | | 0.147 | 0.146 | 0.139 | 0.123 | 0.8 |
| 19 | 0.02u/mL GDH-8 | | | | | 0.003 | 0.002 | 1.589 | 1.573 | 786.5 |
| 20 | Blank | | | | | 0.001 | 0.000 | 0.016 | 0.000 | |

FIG. 11

| | T132A | D446H | V882S | Dm | PMS-NTB 0.1% Triton X-100 | | | ΔO.S. /ABS | Activity u/mL | Protein μg/mL | Specific activity u/mg |
|---|---|---|---|---|---|---|---|---|---|---|---|
| | | | | | Measured value T | Blank B | T-B | | | | |
| pYES-GO-M-6 0.25u/mL | O | | | 3 | 0.751 | 0.002 | 0.749 | 0.747 | 0.12 | 18.6 | 6.7 |
| pYES-GO-M-7 0.1u/mL | O | O | | 3 | 1.267 | 0.001 | 1.266 | 1.264 | 0.22 | 24.7 | 9.0 |
| pYES-GO-M-10 0.05u/mL | O | | O | 3 | 0.742 | 0.002 | 0.740 | 0.738 | 0.12 | 15.3 | 8.1 |
| pYES-GO-M-13 0.03u/mL | | O | O | 3 | 0.433 | 0.002 | 0.431 | 0.429 | 0.07 | 17.9 | 3.9 |
| GDH-8 | | | | | 1.420 | 0.001 | 1.419 | 1.417 | | | |
| | | | | | 0.869 | 0.001 | 0.868 | 0.866 | | | |
| | | | | | 0.353 | 0.001 | 0.352 | 0.350 | | | |
| | | | | | 0.151 | 0.002 | 0.149 | 0.147 | | | |
| Blank | | | | | 0.003 | 0.001 | 0.002 | 0.000 | | | |

FIG. 12

|  | GO activity | GDH activity | GDH/GO |
|---|---|---|---|
| D446H, V582S | 0.007 | 0.157 | 24.2 |
| D446H, V582R | 0.008 | 0.281 | 35.1 |
| D446H, V582L | 0.021 | 0.665 | 31.7 |
| D446H, V582P | 0.000 | 0.761 | —(*) |

FIG. 14

SEQUENCE LISTING

```
<160> NUMBER OF SEQ ID NOS: 64

<210> SEQ ID NO 1
<211> LENGTH: 605
<212> TYPE: PRT
<213> ORGANISM: Aspergillus niger

<400> SEQUENCE: 1

Met Gln Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ile Ala Gly
            35                  40                  45

Gly Gly Leu Thr Gly Leu Thr Thr Ala Ala Arg Leu Thr Glu Asn Pro
        50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
                100                 105                 110

Thr Ala Leu Ile Arg Ser Gly Asn Gly Leu Gly Gly Ser Thr Leu Val
            115                 120                 125

Asn Gly Gly Thr Trp Thr Arg Pro His Lys Ala Gln Val Asp Ser Trp
        130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
```

```
              195                 200                 205
Lys Ala Leu Met Ser Ala Val Glu Asp Arg Gly Val Pro Thr Lys Lys
210                 215                 220
Asp Leu Gly Cys Gly Asp Pro His Gly Val Ser Met Phe Pro Asn Thr
225                 230                 235                 240
Leu His Glu Asp Gln Val Arg Ser Asp Ala Ala Arg Glu Trp Leu Leu
                245                 250                 255
Pro Asn Tyr Gln Arg Pro Asn Leu Gln Val Leu Thr Gly Arg Tyr Val
                260                 265                 270
Gly Lys Val Leu Leu Ser Gln Asn Ala Thr Thr Pro Arg Ala Val Gly
                275                 280                 285
Val Glu Phe Gly Thr His Lys Gly Asn Thr His Asn Val Tyr Ala Lys
290                 295                 300
His Glu Val Leu Leu Ala Ala Gly Ser Ala Val Ser Pro Thr Ile Leu
305                 310                 315                 320
Glu Tyr Ser Gly Ile Gly Met Lys Ser Ile Leu Glu Pro Leu Gly Ile
                325                 330                 335
Asp Thr Val Val Asp Leu Pro Val Gly Leu Asn Leu Gln Asp Gln Thr
                340                 345                 350
Thr Ser Thr Val Arg Ser Arg Ile Thr Ser Ala Gly Ala Gly Gln Gly
                355                 360                 365
Gln Ala Ala Trp Phe Ala Thr Phe Asn Glu Thr Phe Gly Asp Tyr Ala
370                 375                 380
Glu Lys Ala His Glu Leu Leu Asn Thr Lys Leu Glu Gln Trp Ala Glu
385                 390                 395                 400
Glu Ala Val Ala Arg Gly Gly Phe His Asn Thr Thr Ala Leu Leu Ile
                405                 410                 415
Gln Tyr Glu Asn Tyr Arg Asp Trp Ile Val Lys Asp Asn Val Ala Tyr
                420                 425                 430
Ser Glu Leu Phe Leu Asp Thr Ala Gly Val Ala Ser Phe Asp Val Trp
                435                 440                 445
Asp Leu Leu Pro Phe Thr Arg Gly Tyr Val His Ile Leu Asp Lys Asp
450                 455                 460
Pro Tyr Leu Arg His Phe Ala Tyr Asp Pro Gln Tyr Phe Leu Asn Glu
465                 470                 475                 480
Leu Asp Leu Leu Gly Gln Ala Ala Thr Gln Leu Ala Arg Asn Ile
                485                 490                 495
Ser Asn Ser Gly Ala Met Gln Thr Tyr Phe Ala Gly Glu Thr Ile Pro
                500                 505                 510
Gly Asp Asn Leu Ala Tyr Asp Ala Asp Leu Ser Ala Trp Val Glu Tyr
                515                 520                 525
Ile Pro Tyr Asn Phe Arg Pro Asn Tyr His Gly Val Gly Thr Cys Ser
                530                 535                 540
Met Met Pro Lys Glu Met Gly Gly Val Val Asp Asn Ala Ala Arg Val
545                 550                 555                 560
Tyr Gly Val Gln Gly Leu Arg Val Ile Asp Gly Ser Ile Pro Pro Thr
                565                 570                 575
Gln Met Ser Ser His Val Met Thr Val Phe Tyr Ala Met Ala Leu Lys
                580                 585                 590
Val Ala Asp Ala Ile Leu Ala Asp Tyr Ala Ser Met Gln
                595                 600                 605

<210> SEQ ID NO 2
```

```
<211> LENGTH: 605
<212> TYPE: PRT
<213> ORGANISM: Penicillium amagasakiense

<400> SEQUENCE: 2

Met Val Ser Val Phe Leu Ser Thr Leu Leu Ser Ala Ala Ala Val
1               5                   10                  15

Gln Ala Tyr Leu Pro Ala Gln Ile Asp Val Gln Ser Ser Leu Leu
            20                  25                  30

Ser Asp Pro Ser Lys Val Ala Gly Lys Thr Tyr Asp Tyr Ile Ile Ala
            35                  40                  45

Gly Gly Gly Leu Thr Gly Leu Thr Val Ala Ala Lys Leu Thr Glu Asn
    50                  55                  60

Pro Lys Ile Lys Val Leu Val Ile Glu Lys Gly Phe Tyr Glu Ser Asn
65                  70                  75                  80

Asp Gly Ala Ile Ile Glu Asp Pro Asn Ala Tyr Gly Gln Ile Phe Gly
                85                  90                  95

Thr Thr Val Asp Gln Asn Tyr Leu Thr Val Pro Leu Ile Asn Asn Arg
                100                 105                 110

Thr Asn Asn Ile Lys Ala Gly Lys Gly Leu Gly Gly Ser Thr Leu Ile
            115                 120                 125

Asn Gly Asp Ser Trp Thr Arg Pro Asp Lys Val Gln Ile Asp Ser Trp
    130                 135                 140

Glu Lys Val Phe Gly Met Glu Gly Trp Asn Trp Asp Asn Met Phe Glu
145                 150                 155                 160

Tyr Met Lys Lys Ala Glu Ala Ala Arg Thr Pro Thr Ala Ala Gln Leu
                165                 170                 175

Ala Ala Gly His Ser Phe Asn Ala Thr Cys His Gly Thr Asn Gly Thr
            180                 185                 190

Val Gln Ser Gly Ala Arg Asp Asn Gly Gln Pro Trp Ser Pro Ile Met
    195                 200                 205

Lys Ala Leu Met Asn Thr Val Ser Ala Leu Gly Val Pro Val Gln Gln
    210                 215                 220

Asp Phe Leu Cys Gly His Pro Arg Gly Val Ser Met Ile Met Asn Asn
225                 230                 235                 240

Leu Asp Glu Asn Gln Val Arg Val Asp Ala Ala Arg Ala Trp Leu Leu
                245                 250                 255

Pro Asn Tyr Gln Arg Ser Asn Leu Glu Ile Leu Thr Gly Gln Met Val
                260                 265                 270

Gly Lys Val Leu Phe Lys Gln Thr Ala Ser Gly Pro Gln Ala Val Gly
            275                 280                 285

Val Asn Phe Gly Thr Asn Lys Ala Val Asn Phe Asp Val Phe Ala Lys
    290                 295                 300

His Glu Val Leu Leu Ala Ala Gly Ser Ala Ile Ser Pro Leu Ile Leu
305                 310                 315                 320

Glu Tyr Ser Gly Ile Gly Leu Lys Ser Val Leu Asp Gln Ala Asn Val
                325                 330                 335

Thr Gln Leu Leu Asp Leu Pro Val Gly Ile Asn Met Gln Asp Gln Thr
            340                 345                 350

Thr Thr Thr Val Ser Ser Arg Ala Ser Ser Ala Gly Ala Gly Gln Gly
            355                 360                 365

Gln Ala Val Phe Phe Ala Asn Phe Thr Glu Thr Phe Gly Asp Tyr Ala
    370                 375                 380

Pro Gln Ala Arg Asp Leu Leu Asn Thr Lys Leu Asp Gln Trp Ala Glu
```

-continued

```
            385                 390                 395                 400
        Glu Thr Val Ala Arg Gly Gly Phe His Asn Val Thr Ala Leu Lys Val
                        405                 410                 415
        Gln Tyr Glu Asn Tyr Arg Asn Trp Leu Leu Asp Glu Asp Val Ala Phe
                        420                 425                 430
        Ala Glu Leu Phe Met Asp Thr Glu Gly Lys Ile Asn Phe Asp Leu Trp
                        435                 440                 445
        Asp Leu Ile Pro Phe Thr Arg Gly Ser Val His Ile Leu Ser Ser Asp
        450                 455                 460
        Pro Tyr Leu Trp Gln Phe Ala Asn Asp Pro Lys Phe Phe Leu Asn Glu
        465                 470                 475                 480
        Phe Asp Leu Leu Gly Gln Ala Ala Ser Lys Leu Ala Arg Asp Leu
                        485                 490                 495
        Thr Ser Gln Gly Ala Met Lys Glu Tyr Phe Ala Gly Glu Thr Leu Pro
                        500                 505                 510
        Gly Tyr Asn Leu Val Gln Asn Ala Thr Leu Ser Gln Trp Ser Asp Tyr
                        515                 520                 525
        Val Leu Gln Asn Phe Arg Pro Asn Trp His Ala Val Ser Ser Cys Ser
        530                 535                 540
        Met Met Ser Arg Glu Leu Gly Gly Val Val Asp Ala Thr Ala Lys Val
        545                 550                 555                 560
        Tyr Gly Thr Gln Gly Leu Arg Val Ile Asp Gly Ser Ile Pro Pro Thr
                        565                 570                 575
        Gln Val Ser Ser His Val Met Thr Ile Phe Tyr Gly Met Ala Leu Lys
                        580                 585                 590
        Val Ala Asp Ala Ile Leu Asp Asp Tyr Ala Lys Ser Ala
                        595                 600                 605

<210> SEQ ID NO 3
<211> LENGTH: 592
<212> TYPE: PRT
<213> ORGANISM: Penicillium italicum

<400> SEQUENCE: 3

Met Arg Ser Leu Ile Gly Leu Ala Leu Leu Pro Leu Ala Val Ala Val
1               5                   10                  15

Pro His Ala Ser His Lys Ser Asp Ser Thr Tyr Asp Tyr Ile Ile Val
                20                  25                  30

Gly Gly Gly Thr Ser Gly Leu Val Val Ala Asn Arg Leu Ser Glu Gln
            35                  40                  45

Lys Asp Thr Thr Val Leu Val Ile Glu Ala Gly Gly Ser Val Tyr Asn
        50                  55                  60

Asn Pro Asn Val Thr Asn Thr Leu Gly Tyr Gly Lys Ala Phe Gly Thr
65                  70                  75                  80

Asp Ile Asp Trp Ala Tyr Glu Thr Thr Ala Gln Glu His Ala Gly Gly
                85                  90                  95

Phe Pro Gln Ile Val Arg Ala Gly Lys Ala Leu Gly Gly Thr Ser Thr
                100                 105                 110

Ile Asn Gly Met Ala Tyr Leu Arg Ala Gln Ala Ala Gln Ile Asp Ala
            115                 120                 125

Trp Glu Thr Val Gly Asn Lys Gly Trp Asn Trp Lys Thr Leu Leu Pro
        130                 135                 140

Tyr Phe Lys Lys Ser Glu Gln Phe Gln Asp Pro Ala Lys Tyr Pro Phe
145                 150                 155                 160
```

```
Leu Asp Gly Ser Gly Val Ser Phe Asp Pro Ala Tyr His Gly Phe Thr
            165                 170                 175
Gly Pro Leu Lys Val Gly Trp Ser Ser Thr Gln Leu Asn Asp Gly Leu
        180                 185                 190
Ala Gln Lys Leu Asn Ala Thr Tyr Gln Ser Leu Asp Val Pro Val Pro
    195                 200                 205
Tyr Asn Arg Asp Ala Asn Ser Gly Asp Met Val Gly Tyr Ser Val Tyr
210                 215                 220
Pro Lys Thr Val Asn Ala Asp Leu Asn Ile Arg Glu Asp Ala Ala Arg
225                 230                 235                 240
Ala Phe Tyr Tyr Pro Tyr Gln Asn Arg Thr Asn Leu His Val Trp Leu
            245                 250                 255
Asn Thr His Ala Asn Lys Ile Thr Trp Asn Glu Gly Ser Glu Ala Thr
        260                 265                 270
Ala Asn Gly Val Glu Val Thr Leu Ser Asn Gly Lys Lys Thr Val Val
    275                 280                 285
Lys Ala Thr Arg Glu Val Ile Leu Ala Ala Gly Ala Leu Lys Ser Pro
290                 295                 300
Val Leu Leu Glu Leu Ser Gly Val Gly Asn Pro Asp Ile Leu Ser Lys
305                 310                 315                 320
His Gly Ile Thr Thr Lys Ile Asn Leu Pro Thr Val Gly Glu Asn Leu
            325                 330                 335
Gln Asp Gln Met Asn Asn Gly Leu Lys Phe Glu Ser Lys Lys Thr Tyr
        340                 345                 350
Ser Thr Asp Lys Gly Ser Ser Tyr Val Ala Tyr Pro Ser Ala Asp Gln
    355                 360                 365
Leu Phe Pro Asn Ser Thr Ala Leu Gly Ala Asp Leu Leu Arg Lys Leu
370                 375                 380
Pro Ala Tyr Ala Ala Gln Val Ala Ser Ala Asn Gly Asn Ile Thr Lys
385                 390                 395                 400
Ala Arg Asp Ile Tyr Arg Phe Phe Lys Ile Gln Trp Asp Leu Ile Phe
            405                 410                 415
Lys Asp Glu Ile Pro Val Ala Glu Ile Leu Leu Ser Gly Ser Gly Ala
        420                 425                 430
Ser Tyr Ser Gly Glu Tyr Trp Gly Ser Val Pro Phe Ser Arg Gly Ser
    435                 440                 445
Val His Leu Ser Ser Ala Asp Pro Thr Ala Ala Pro Thr Ile Asp Pro
450                 455                 460
Lys Tyr Phe Met Leu Asp Phe Asp Leu His Ala Gln Ala Gln Ala Ala
465                 470                 475                 480
Arg Phe Ile Arg Glu Ile Phe Lys Thr Glu Pro Leu Ala Asp Thr Ala
            485                 490                 495
Gly Ala Glu Thr Thr Pro Gly Leu Ser Thr Val Ala Ala Gly Ala Asp
        500                 505                 510
Asp Glu Ala Trp Ser Lys Phe Ile Tyr Ser Lys Tyr Arg Ser Asn Tyr
    515                 520                 525
His Pro Ile Thr Thr Ala Gly Met Leu Pro Lys Glu Leu Gly Gly Val
530                 535                 540
Val Asp Thr Ser Leu Lys Val Tyr Gly Thr Ser Asn Val Arg Val Val
545                 550                 555                 560
Asp Ala Ser Val Met Pro Phe Gln Val Cys Gly His Leu Gln Ser Thr
            565                 570                 575
Val Tyr Ala Val Ala Glu Arg Ala Ala Asp Ile Ile Lys Gly Glu Leu
```

<210> SEQ ID NO 4
<211> LENGTH: 590
<212> TYPE: PRT
<213> ORGANISM: Penicillium lilacinoechinulatum

<400> SEQUENCE: 4

```
Met Arg Ser Leu Ile Ser Leu Ala Leu Leu Pro Leu Ala Ala Val
1               5                   10                  15

Pro His Val Ser Arg Ser Ser Glu Thr Thr Tyr Asp Tyr Ile Val Val
            20                  25                  30

Gly Gly Gly Thr Ser Gly Leu Val Ile Ala Asn Arg Leu Ser Glu Leu
            35                  40                  45

Glu Lys Val Asn Val Leu Val Ile Glu Ala Gly Gly Ser Val Tyr Asn
        50                  55                  60

Asn Pro Asn Val Thr Asp Thr Ala Gly Tyr Gly Lys Ala Phe Gly Thr
65                  70                  75                  80

Asp Ile Asp Trp Ala Tyr Glu Thr Val Lys Gln Glu Trp Gly Gly Gly
                85                  90                  95

Thr Lys Gln Thr Val Arg Ala Gly Lys Ala Leu Gly Gly Thr Ser Thr
            100                 105                 110

Ile Asn Gly Met Val Tyr Leu Arg Ala Gln Lys Ser Gln Ile Asp Ala
        115                 120                 125

Trp Glu Lys Ile Gly Asn Asp Gly Trp Asn Trp Lys Asn Leu Phe Pro
    130                 135                 140

Tyr Tyr Arg Lys Gly Glu Lys Phe Gln Val Pro Thr Asp Tyr Ala Phe
145                 150                 155                 160

Leu Glu Gly Thr Gly Val Ala Tyr Asp Pro Ala Phe His Gly Tyr Asn
                165                 170                 175

Gly Pro Leu Lys Val Gly Trp Thr Ser Thr Gln Leu Asn Asp Gly Leu
            180                 185                 190

Ala Gln Val Met Asn Ser Thr Tyr Gln Asn Met Ser Val Pro Val Pro
        195                 200                 205

Tyr Asn Lys Asp Pro Asn Gly Gly Gln Met Val Gly Tyr Ser Val Tyr
    210                 215                 220

Pro Lys Thr Val Asn Ser Glu Leu Asn Ile Arg Glu Asp Ala Ala Arg
225                 230                 235                 240

Ala Tyr Tyr Tyr Pro Tyr Gln Asn Arg Thr Asn Leu His Val Trp Leu
                245                 250                 255

Asn Ser His Val Asn Lys Leu Val Trp Lys Asp Gly Ala Asn Met Thr
            260                 265                 270

Ala Asp Gly Val Glu Val Lys Phe Ser Asn Gly Thr Thr Ala Thr Val
        275                 280                 285

Lys Ala Ala Arg Glu Val Ile Leu Ala Ala Gly Ala Leu Lys Ser Pro
    290                 295                 300

Leu Leu Leu Glu Leu Ser Gly Val Gly Asn Pro Asp Ile Leu Ser Arg
305                 310                 315                 320

His Gly Ile Asp Thr Lys Ile Asn Leu Pro Thr Ile Gly Glu Asn Leu
                325                 330                 335

Gln Asp Gln Met Asn Asn Gly Leu Ala Tyr Thr Ser Lys Lys Asn Tyr
            340                 345                 350

Thr Lys Ala Ala Ser Tyr Val Ala Tyr Pro Ser Ala Glu Glu Leu Phe
        355                 360                 365
```

```
Thr Asn Ala Thr Thr Ile Gly Ala Gln Leu Leu Arg Lys Leu Pro Ala
    370                 375                 380

Tyr Ala Ala Gln Val Ala Ser Ala Asn Gly Asn Val Thr Arg Ala Ala
385                 390                 395                 400

Asp Ile Glu Arg Phe Phe Lys Ile Gln Trp Asp Leu Ile Phe Lys Ser
                405                 410                 415

His Ile Pro Val Ala Glu Ile Leu Leu Glu Pro Phe Gly Phe Thr Tyr
            420                 425                 430

Asp Ser Glu Tyr Trp Gly Ser Val Pro Phe Ser Arg Gly Ser Ile His
        435                 440                 445

Ile Ser Ser Ser Asp Pro Thr Ala Pro Ala Ile Ile Asp Pro Lys Tyr
450                 455                 460

Phe Met Leu Asp Phe Asp Phe His Ala Gln Val Glu Ala Ala Arg Phe
465                 470                 475                 480

Ile Arg Glu Leu Phe Lys Thr Glu Pro Phe Ala Asp Met Ala Gly Ala
                485                 490                 495

Glu Thr Ser Pro Gly Leu Ser Ala Val Ser Ser Asn Ala Asp Asp Glu
            500                 505                 510

Gly Trp Ser Ser Phe Leu Lys Ser Asn Phe Arg Ser Asn Phe His Pro
        515                 520                 525

Ile Thr Thr Ala Gly Met Met Pro Lys Glu Ile Gly Gly Val Val Asp
530                 535                 540

Thr Ser Leu Lys Val Tyr Gly Thr Ser Asn Val Arg Val Val Asp Ala
545                 550                 555                 560

Ser Val Ile Pro Phe Gln Val Cys Gly His Leu Gln Ser Thr Ile Tyr
                565                 570                 575

Ala Val Ala Glu Arg Ala Ala Asp Ile Ile Lys Ala Gln Met
            580                 585                 590

<210> SEQ ID NO 5
<211> LENGTH: 593
<212> TYPE: PRT
<213> ORGANISM: Aspergillus oryzae

<400> SEQUENCE: 5

Met Leu Phe Ser Leu Ala Phe Leu Ser Ala Leu Ser Leu Ala Thr Ala
1               5                   10                  15

Ser Pro Ala Gly Arg Ala Lys Asn Thr Thr Tyr Asp Tyr Ile Val
            20                  25                  30

Val Gly Gly Gly Thr Ser Gly Leu Val Val Ala Asn Arg Leu Ser Glu
            35                  40                  45

Asn Pro Asp Val Ser Val Leu Leu Glu Gly Ala Ser Val Phe
50                  55                  60

Asn Asn Pro Asp Val Thr Asn Ala Asn Gly Tyr Gly Leu Ala Phe Gly
65                  70                  75                  80

Ser Ala Ile Asp Trp Gln Tyr Gln Ser Ile Asn Gln Ser Tyr Ala Gly
                85                  90                  95

Gly Lys Gln Gln Val Leu Arg Ala Gly Lys Ala Leu Gly Gly Thr Ser
            100                 105                 110

Thr Ile Asn Gly Met Ala Tyr Thr Arg Ala Glu Asp Val Gln Ile Asp
        115                 120                 125

Val Trp Gln Lys Leu Gly Asn Glu Gly Trp Thr Trp Lys Asp Leu Leu
    130                 135                 140

Pro Tyr Tyr Leu Lys Ser Glu Asn Leu Thr Ala Pro Thr Ser Ser Gln
145                 150                 155                 160
```

```
Val Ala Ala Gly Ala Ala Tyr Asn Pro Ala Val Gly Lys Glu Gly
                165                 170                 175

Pro Leu Lys Val Gly Trp Ser Gly Ser Leu Ala Ser Gly Asn Leu Ser
            180                 185                 190

Val Ala Leu Asn Arg Thr Phe Gln Ala Ala Gly Val Pro Trp Val Glu
        195                 200                 205

Asp Val Asn Gly Gly Lys Met Arg Gly Phe Asn Ile Tyr Pro Ser Thr
    210                 215                 220

Leu Asp Val Asp Leu Asn Val Arg Glu Asp Ala Ala Arg Ala Tyr Tyr
225                 230                 235                 240

Phe Pro Tyr Asp Asp Arg Lys Asn Leu His Leu Leu Glu Asn Thr Thr
                245                 250                 255

Ala Asn Arg Leu Phe Trp Lys Asn Gly Ser Ala Glu Glu Ala Ile Ala
            260                 265                 270

Asp Gly Val Glu Ile Thr Ser Ala Asp Gly Lys Val Thr Arg Val His
        275                 280                 285

Ala Lys Lys Glu Val Ile Ile Ser Ala Gly Ala Leu Arg Ser Pro Leu
    290                 295                 300

Ile Leu Glu Leu Ser Gly Val Gly Asn Pro Thr Ile Leu Lys Lys Asn
305                 310                 315                 320

Asn Ile Thr Pro Arg Val Asp Leu Pro Thr Val Gly Glu Asn Leu Gln
                325                 330                 335

Asp Gln Phe Asn Asn Gly Met Ala Gly Glu Gly Tyr Gly Val Leu Ala
            340                 345                 350

Gly Ala Ser Thr Val Thr Tyr Pro Ser Ile Ser Asp Val Phe Gly Asn
        355                 360                 365

Glu Thr Asp Ser Ile Val Ala Ser Leu Arg Ser Gln Leu Ser Asp Tyr
    370                 375                 380

Ala Ala Ala Thr Val Lys Val Ser Asn Gly His Met Lys Gln Glu Asp
385                 390                 395                 400

Leu Glu Arg Leu Tyr Gln Leu Gln Phe Asp Leu Ile Val Lys Asp Lys
                405                 410                 415

Val Pro Ile Ala Glu Ile Leu Phe His Pro Gly Gly Gly Asn Ala Val
            420                 425                 430

Ser Ser Glu Phe Trp Gly Leu Leu Pro Phe Ala Arg Gly Asn Ile His
        435                 440                 445

Ile Ser Ser Asn Asp Pro Thr Ala Pro Ala Ala Ile Asn Pro Asn Tyr
    450                 455                 460

Phe Met Phe Glu Trp Asp Gly Lys Ser Gln Ala Gly Ile Ala Lys Tyr
465                 470                 475                 480

Ile Arg Lys Ile Leu Arg Ser Ala Pro Leu Asn Lys Leu Ile Ala Lys
                485                 490                 495

Glu Thr Lys Pro Gly Leu Ser Glu Ile Pro Ala Thr Ala Ala Asp Glu
            500                 505                 510

Lys Trp Val Glu Trp Leu Lys Ala Asn Tyr Arg Ser Asn Phe His Pro
        515                 520                 525

Val Gly Thr Ala Ala Met Met Pro Arg Ser Ile Gly Gly Val Val Asp
    530                 535                 540

Asn Arg Leu Arg Val Tyr Gly Thr Ser Asn Val Arg Val Val Asp Ala
545                 550                 555                 560

Ser Val Leu Pro Phe Gln Val Cys Gly His Leu Val Ser Thr Leu Tyr
                565                 570                 575
```

-continued

```
            Ala Val Ala Glu Arg Ala Ser Asp Leu Ile Lys Glu Asp Ala Lys Ser
                        580                 585                 590

Ala

<210> SEQ ID NO 6
<211> LENGTH: 591
<212> TYPE: PRT
<213> ORGANISM: Aspergillus terreus

<400> SEQUENCE: 6

Met Leu Gly Lys Leu Ser Phe Leu Ser Ala Leu Ser Leu Ala Val Ala
1               5                   10                  15

Ala Pro Leu Ser Asn Ser Thr Ser Ala Lys Tyr Asp Tyr Ile Val Ile
            20                  25                  30

Gly Gly Gly Thr Ser Gly Leu Ala Val Ala Asn Arg Leu Ser Glu Asp
        35                  40                  45

Pro Asn Val Asn Val Leu Ile Leu Glu Ala Gly Gly Ser Val Trp Asn
50                  55                  60

Asn Pro Asn Val Thr Asn Val Asp Gly Tyr Gly Leu Ala Phe Gly Ser
65                  70                  75                  80

Asp Ile Asp Trp Gln Tyr Gln Ser Val Asn Gln Pro Tyr Gly Gly Asn
                85                  90                  95

Leu Ser Gln Val Leu Arg Ala Gly Lys Ala Leu Gly Gly Thr Ser Thr
            100                 105                 110

Ile Asn Gly Met Ala Tyr Thr Arg Ala Glu Asp Val Gln Ile Asp Ala
        115                 120                 125

Trp Glu Thr Ile Gly Asn Thr Gly Trp Thr Trp Lys Asn Leu Phe Pro
130                 135                 140

Tyr Tyr Arg Lys Ser Glu Asn Phe Thr Val Pro Thr Lys Ser Gln Thr
145                 150                 155                 160

Ser Leu Gly Ala Ser Tyr Glu Ala Gly Ala His Gly His Glu Gly Pro
                165                 170                 175

Leu Asp Val Ala Phe Thr Gln Ile Glu Ser Asn Asn Leu Thr Thr Tyr
            180                 185                 190

Leu Asn Arg Thr Phe Gln Gly Met Gly Leu Pro Trp Thr Glu Asp Val
        195                 200                 205

Asn Gly Gly Lys Met Arg Gly Phe Asn Leu Tyr Pro Thr Val Asn Leu
210                 215                 220

Glu Glu Tyr Val Arg Glu Asp Ala Ala Arg Ala Tyr Tyr Trp Pro Tyr
225                 230                 235                 240

Lys Ser Arg Pro Asn Leu His Val Leu Leu Asn Thr Phe Ala Asn Arg
                245                 250                 255

Ile Val Trp Asp Gly Glu Ala His Asp Gly His Ile Thr Ala Ser Gly
            260                 265                 270

Val Glu Ile Thr Ser Arg Asn Gly Thr Val Arg Val Ile Asn Ala Glu
        275                 280                 285

Lys Glu Val Ile Val Ser Ala Gly Ala Leu Lys Ser Pro Ala Ile Leu
290                 295                 300

Glu Leu Ser Gly Ile Gly Asn Pro Ser Val Leu Asp Lys His Asn Ile
305                 310                 315                 320

Pro Val Lys Val Asn Leu Pro Thr Val Gly Glu Asn Leu Gln Asp Gln
                325                 330                 335

Val Asn Ser His Met Asp Ala Ser Gly Asn Thr Ser Ile Ser Gly Thr
            340                 345                 350
```

```
Lys Ala Val Ser Tyr Pro Asp Val Tyr Asp Val Phe Gly Asp Glu Ala
            355                 360                 365

Glu Ser Val Ala Lys Gln Ile Arg Ala Asn Leu Lys Gln Tyr Ala Ala
        370                 375                 380

Asp Thr Ala Lys Ala Asn Gly Asn Ile Met Lys Ala Ala Asp Leu Glu
385                 390                 395                 400

Arg Leu Phe Glu Val Gln Tyr Asp Leu Ile Phe Lys Gly Arg Val Pro
                405                 410                 415

Ile Ala Glu Val Leu Asn Tyr Pro Gly Ser Ala Thr Ser Val Phe Ala
                420                 425                 430

Glu Phe Trp Ala Leu Leu Pro Phe Ala Arg Gly Ser Val His Ile Gly
            435                 440                 445

Ser Ser Asn Pro Ala Glu Phe Pro Val Ile Asn Pro Asn Tyr Phe Met
        450                 455                 460

Leu Asp Trp Asp Ala Lys Ser Tyr Val Ala Val Ala Lys Tyr Ile Arg
465                 470                 475                 480

Arg Ser Phe Glu Ser Tyr Pro Leu Ser Ser Ile Val Lys Glu Ser Thr
                485                 490                 495

Pro Gly Tyr Asp Val Ile Pro Arg Asn Ala Ser Glu Gln Ser Trp Lys
            500                 505                 510

Glu Trp Val Phe Asp Lys Asn Tyr Arg Ser Asn Phe His Pro Val Gly
        515                 520                 525

Thr Ala Ala Met Met Pro Arg Glu Ile Gly Gly Val Val Asp Glu Arg
        530                 535                 540

Leu Asn Val Tyr Gly Thr Thr Asn Val Arg Val Val Asp Ala Ser Val
545                 550                 555                 560

Leu Pro Phe Gln Val Cys Gly His Leu Val Ser Thr Leu Tyr Ala Val
                565                 570                 575

Ala Glu Arg Ala Ala Asp Leu Ile Lys Ala Asp Ala Gly Arg Arg
            580                 585                 590

<210> SEQ ID NO 7
<211> LENGTH: 605
<212> TYPE: PRT
<213> ORGANISM: Aspergillus niger

<400> SEQUENCE: 7

Met Ser Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ile Ala Gly
            35                  40                  45

Gly Gly Leu Thr Gly Leu Thr Thr Ala Ala Arg Leu Thr Glu Asn Pro
        50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
                100                 105                 110

Thr Ala Leu Ile Arg Ser Gly Asn Gly Leu Gly Gly Ser Thr Leu Val
            115                 120                 125

Asn Gly Gly Ala Trp Thr Arg Pro His Lys Ala Gln Val Asp Ser Trp
        130                 135                 140
```

```
Glu Thr Val Phe Gly Asn Gly Trp Asn Trp Asp Ser Val Ala Ala
145                 150                 155                 160

Tyr Ser Leu Gln Ala Glu Arg Ala Arg Ala Pro Asn Ala Lys Gln Ile
            165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Tyr Ser Pro Ile Val
        195                 200                 205

Lys Ala Leu Met Ser Ala Val Glu Asp Arg Gly Val Pro Thr Lys Lys
            210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
        290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ser Thr Val Arg Ser Arg Ile Thr Ser Ala Gly Ala Gly Gln Gly
            355                 360                 365

Gln Ala Ala Trp Phe Ala Thr Phe Asn Glu Thr Phe Gly Asp Tyr Ala
        370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
        420                 425                 430

Ser Glu Leu Phe Leu Asp Thr Ala Gly Val Ala Ser Phe Asp Val Trp
        435                 440                 445

Asp Leu Leu Pro Phe Thr Arg Gly Tyr Val His Ile Leu Asp Lys Asp
450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Val Glu Tyr
            515                 520                 525

Ile Pro Tyr Asn Phe Arg Pro Asn Tyr His Gly Val Gly Thr Cys Ser
        530                 535                 540

Met Met Pro Lys Glu Met Gly Gly Val Val Asp Asn Ala Ala Arg Val
545                 550                 555                 560
```

```
Tyr Gly Val Gln Gly Leu Arg Val Ile Asp Gly Ser Ile Pro Pro Thr
                565                 570                 575

Gln Met Ser Ser His Val Met Thr Val Phe Tyr Ala Met Ala Leu Lys
                580                 585                 590

Val Ala Asp Ala Ile Leu Ala Asp Tyr Ala Ser Met Gln
                595                 600                 605

<210> SEQ ID NO 8
<211> LENGTH: 605
<212> TYPE: PRT
<213> ORGANISM: Aspergillus niger

<400> SEQUENCE: 8

Met Ser Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ile Ala Gly
            35                  40                  45

Gly Gly Leu Thr Gly Leu Thr Thr Ala Ala Arg Leu Thr Glu Asn Pro
        50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
                100                 105                 110

Thr Ala Leu Ile Arg Ser Gly Asn Gly Leu Gly Gly Ser Thr Leu Val
            115                 120                 125

Asn Gly Gly Thr Trp Thr Arg Pro His Lys Ala Gln Val Asp Ser Trp
        130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335
```

```
Asp Thr Val Val Asp Leu Pro Val Gly Leu Asn Leu Gln Asp Gln Ala
            340                 345                 350

Thr Ser Thr Val Arg Ser Arg Ile Thr Ser Ala Gly Ala Gly Gln Gly
            355                 360                 365

Gln Ala Ala Trp Phe Ala Thr Phe Asn Glu Thr Phe Gly Asp Tyr Ala
        370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe Asp Val Trp
            435                 440                 445

Asp Leu Leu Pro Phe Thr Arg Gly Tyr Val His Ile Leu Asp Lys Asp
        450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Val Glu Tyr
            515                 520                 525

Ile Pro Tyr Asn Phe Arg Pro Asn Tyr His Gly Val Gly Thr Cys Ser
        530                 535                 540

Met Met Pro Lys Glu Met Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Val Met Thr Val Phe Tyr Ala Met Ala Leu Lys
            580                 585                 590

Val Ala Asp Ala Ile Leu Ala Asp Tyr Ala Ser Met Gln
        595                 600                 605

<210> SEQ ID NO 9
<211> LENGTH: 605
<212> TYPE: PRT
<213> ORGANISM: Aspergillus niger

<400> SEQUENCE: 9

Met Ser Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Glu Val Ala Gly Arg Thr Val Asp Tyr Ile Ile Ala Gly
        35                  40                  45

Gly Gly Leu Thr Gly Leu Thr Thr Ala Ala Arg Leu Thr Glu Asn Pro
    50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
```

```
                  100                 105                 110
Thr Ala Leu Ile Arg Ser Gly Asn Gly Leu Gly Gly Ser Thr Leu Val
            115                 120                 125
Asn Gly Gly Thr Trp Thr Arg Pro His Lys Ala Gln Val Asp Ser Trp
        130                 135                 140
Glu Thr Val Phe Gly Asn Glu Gly Trp Asn Trp Asp Ser Val Ala Ala
145                 150                 155                 160
Tyr Ser Leu Gln Ala Glu Arg Ala Arg Ala Pro Asn Ala Lys Gln Ile
                165                 170                 175
Ala Ala Gly His Tyr Phe Asn Ala Ser Cys His Gly Ile Asn Gly Thr
            180                 185                 190
Val His Ala Gly Pro Arg Asp Thr Gly Asp Asp Tyr Ser Pro Ile Val
        195                 200                 205
Lys Ala Leu Met Ser Ala Val Glu Asp Arg Gly Val Pro Thr Lys Lys
210                 215                 220
Asp Leu Gly Cys Gly Asp Pro His Gly Val Ser Met Phe Pro Asn Thr
225                 230                 235                 240
Leu His Glu Asp Gln Val Arg Ser Asp Ala Ala Arg Glu Trp Leu Leu
                245                 250                 255
Pro Asn Tyr Gln Arg Pro Asn Leu Gln Val Leu Thr Gly Arg Tyr Val
                260                 265                 270
Gly Lys Val Leu Leu Ser Gln Asn Ala Thr Thr Pro Arg Ala Val Gly
            275                 280                 285
Val Glu Phe Gly Thr His Lys Gly Asn Thr His Asn Val Tyr Ala Lys
        290                 295                 300
His Glu Val Leu Leu Ala Ala Gly Ser Ala Val Ser Pro Thr Ile Leu
305                 310                 315                 320
Glu Tyr Ser Gly Ile Gly Met Lys Ser Ile Leu Glu Pro Leu Gly Ile
                325                 330                 335
Asp Thr Val Val Asp Leu Pro Val Gly Leu Asn Leu Gln Asp Gln Thr
                340                 345                 350
Thr Ser Thr Val Arg Ser Arg Ile Thr Ser Ala Gly Ala Gly Gln Gly
            355                 360                 365
Gln Ala Ala Trp Phe Ala Thr Phe Asn Glu Thr Phe Gly Asp Tyr Ala
        370                 375                 380
Glu Lys Ala His Glu Leu Leu Asn Thr Lys Leu Glu Gln Trp Ala Glu
385                 390                 395                 400
Glu Ala Val Ala Arg Gly Gly Phe His Asn Thr Thr Ala Leu Leu Ile
                405                 410                 415
Gln Tyr Glu Asn Tyr Arg Asp Trp Ile Val Lys Asp Asn Val Ala Tyr
                420                 425                 430
Ser Glu Leu Phe Leu Asp Thr Ala Gly Val Ala Ser Phe His Val Trp
            435                 440                 445
Asp Leu Leu Pro Phe Thr Arg Gly Tyr Val His Ile Leu Asp Lys Asp
        450                 455                 460
Pro Tyr Leu Arg His Phe Ala Tyr Asp Pro Gln Tyr Phe Leu Asn Glu
465                 470                 475                 480
Leu Asp Leu Leu Gly Gln Ala Ala Thr Gln Leu Ala Arg Asn Ile
                485                 490                 495
Ser Asn Ser Gly Ala Met Gln Thr Tyr Phe Ala Gly Glu Thr Ile Pro
            500                 505                 510
Gly Asp Asn Leu Ala Tyr Asp Ala Asp Leu Ser Ala Trp Val Glu Tyr
        515                 520                 525
```

```
Ile Pro Tyr Asn Phe Arg Pro Asn Tyr His Gly Val Gly Thr Cys Ser
    530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Val Met Thr Val Phe Tyr Ala Met Ala Leu Lys
                580                 585                 590

Val Ala Asp Ala Ile Leu Ala Asp Tyr Ala Ser Met Gln
                595                 600                 605

<210> SEQ ID NO 10
<211> LENGTH: 605
<212> TYPE: PRT
<213> ORGANISM: Aspergillus niger

<400> SEQUENCE: 10

Met Ser Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ile Ala Gly
            35                  40                  45

Gly Gly Leu Thr Gly Leu Thr Thr Ala Ala Arg Leu Thr Glu Asn Pro
    50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
                100                 105                 110

Thr Ala Leu Ile Arg Ser Gly Asn Gly Leu Gly Gly Ser Thr Leu Val
            115                 120                 125

Asn Gly Gly Thr Trp Thr Arg Pro His Lys Ala Gln Val Asp Ser Trp
130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
    210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
                260                 265                 270

Gly Lys Val Leu Leu Ser Gln Asn Ala Thr Thr Pro Arg Ala Val Gly
            275                 280                 285

Val Glu Phe Gly Thr His Lys Gly Asn Thr His Asn Val Tyr Ala Lys
```

```
                    290                 295                 300
His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
                    340                 345                 350

Thr Ser Thr Val Arg Ser Arg Ile Thr Ser Ala Gly Ala Gly Gln Gly
                355                 360                 365

Gln Ala Ala Trp Phe Ala Thr Phe Asn Glu Thr Phe Gly Asp Tyr Ala
            370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
                    420                 425                 430

Ser Glu Leu Phe Leu Asp Thr Ala Gly Val Ala Ser Phe Asp Val Trp
                435                 440                 445

Asp Leu Leu Pro Phe Thr Arg Gly Tyr Val His Ile Leu Asp Lys Asp
            450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Thr Gln Leu Ala Arg Asn Ile
                    485                 490                 495

Ser Asn Ser Gly Ala Met Gln Thr Tyr Phe Ala Gly Glu Thr Ile Pro
                500                 505                 510

Gly Asp Asn Leu Ala Tyr Asp Ala Asp Leu Ser Ala Trp Val Glu Tyr
            515                 520                 525

Ile Pro Tyr Asn Phe Arg Pro Asn Tyr His Gly Val Gly Thr Cys Ser
                530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Ser Met Thr Val Phe Tyr Ala Met Ala Leu Lys
            580                 585                 590

Val Ala Asp Ala Ile Leu Ala Asp Tyr Ala Ser Met Gln
                595                 600                 605

<210> SEQ ID NO 11
<211> LENGTH: 605
<212> TYPE: PRT
<213> ORGANISM: Aspergillus niger

<400> SEQUENCE: 11

Met Ser Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ile Ala Gly
            35                  40                  45

Gly Gly Leu Thr Gly Leu Thr Thr Ala Ala Arg Leu Thr Glu Asn Pro
        50                  55                  60
```

```
Asp Ile Thr Val Leu Val Ile Glu Ser Gly Ser Tyr Glu Ser Asp Arg
 65                  70                  75                  80

Gly Pro Ile Ile Glu Asp Leu Asn Ala Tyr Gly Asp Ile Phe Gly Ser
             85                  90                  95

Ser Val Asp His Ala Tyr Glu Thr Val Glu Leu Ala Thr Asn Asn Gln
         100                 105                 110

Thr Ala Leu Ile Arg Ser Gly Asn Gly Leu Gly Gly Ser Thr Leu Val
     115                 120                 125

Asn Gly Gly Ala Trp Thr Arg Pro His Lys Ala Gln Val Asp Ser Trp
130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                 165                 170                 175

Ala Ala Gly His Tyr Phe Asn Ala Ser Cys His Gly Ile Asn Gly Thr
             180                 185                 190

Val His Ala Gly Pro Arg Asp Thr Gly Asp Tyr Ser Pro Ile Val
         195                 200                 205

Lys Ala Leu Met Ser Ala Val Glu Asp Arg Gly Val Pro Thr Lys Lys
     210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                 245                 250                 255

Pro Asn Tyr Gln Arg Pro Asn Leu Gln Val Leu Thr Gly Arg Tyr Val
             260                 265                 270

Gly Lys Val Leu Leu Ser Gln Asn Ala Thr Thr Pro Arg Ala Val Gly
     275                 280                 285

Val Glu Phe Gly Thr His Lys Gly Asn Thr His Asn Val Tyr Ala Lys
     290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                 325                 330                 335

Asp Thr Val Val Asp Leu Pro Val Gly Leu Asn Leu Gln Asp Gln Ala
             340                 345                 350

Thr Ser Thr Val Arg Ser Arg Ile Thr Ser Ala Gly Ala Gly Gln Gly
     355                 360                 365

Gln Ala Ala Trp Phe Ala Thr Phe Asn Glu Thr Phe Gly Asp Tyr Ala
370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                 405                 410                 415

Gln Tyr Glu Asn Tyr Arg Asp Trp Ile Val Lys Asp Asn Val Ala Tyr
             420                 425                 430

Ser Glu Leu Phe Leu Asp Thr Ala Gly Val Ala Ser Phe Asp Val Trp
     435                 440                 445

Asp Leu Leu Pro Phe Thr Arg Gly Tyr Val His Ile Leu Asp Lys Asp
     450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
```

```
                       485                 490                 495
Ser Asn Ser Gly Ala Met Gln Thr Tyr Phe Ala Gly Glu Thr Ile Pro
                500                 505                 510

Gly Asp Asn Leu Ala Tyr Asp Ala Asp Leu Ser Ala Trp Val Glu Tyr
            515                 520                 525

Ile Pro Tyr Asn Phe Arg Pro Asn Tyr His Gly Val Gly Thr Cys Ser
        530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Val Met Thr Val Phe Tyr Ala Met Ala Leu Lys
            580                 585                 590

Val Ala Asp Ala Ile Leu Ala Asp Tyr Ala Ser Met Gln
        595                 600                 605

<210> SEQ ID NO 12
<211> LENGTH: 605
<212> TYPE: PRT
<213> ORGANISM: Aspergillus niger

<400> SEQUENCE: 12

Met Ser Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Glu Val Ala Gly Arg Thr Val Asp Tyr Ile Ala Gly
        35                  40                  45

Gly Gly Leu Thr Gly Leu Thr Thr Ala Ala Arg Leu Thr Glu Asn Pro
    50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Ala Trp Thr Arg Pro His Lys Ala Gln Val Asp Ser Trp
130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255
```

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
    290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ser Thr Val Arg Ser Arg Ile Thr Ser Ala Gly Ala Gly Gln Gly
        355                 360                 365

Gln Ala Ala Trp Phe Ala Thr Phe Asn Glu Thr Phe Gly Asp Tyr Ala
    370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe His Val Trp
        435                 440                 445

Asp Leu Leu Pro Phe Thr Arg Gly Tyr Val His Ile Leu Asp Lys Asp
450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Thr Gln Leu Ala Arg Asn Ile
            485                 490                 495

Ser Asn Ser Gly Ala Met Gln Thr Tyr Phe Ala Gly Glu Thr Ile Pro
        500                 505                 510

Gly Asp Asn Leu Ala Tyr Asp Ala Asp Leu Ser Ala Trp Val Glu Tyr
    515                 520                 525

Ile Pro Tyr Asn Phe Arg Pro Asn Tyr His Gly Val Gly Thr Cys Ser
530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
            565                 570                 575

Gln Met Ser Ser His Val Met Thr Val Phe Tyr Ala Met Ala Leu Lys
        580                 585                 590

Val Ala Asp Ala Ile Leu Ala Asp Tyr Ala Ser Met Gln
    595                 600                 605

<210> SEQ ID NO 13
<211> LENGTH: 605
<212> TYPE: PRT
<213> ORGANISM: Aspergillus niger

<400> SEQUENCE: 13

Met Ser Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
            20                  25                  30

```
Asp Pro Lys Glu Val Ala Gly Arg Thr Val Asp Tyr Ile Ile Ala Gly
         35                  40                  45

Gly Gly Leu Thr Gly Leu Thr Thr Ala Ala Arg Leu Thr Glu Asn Pro
     50                  55                  60

Asp Ile Thr Val Leu Val Ile Glu Ser Gly Ser Tyr Glu Ser Asp Arg
 65              70                  75                  80

Gly Pro Ile Ile Glu Asp Leu Asn Ala Tyr Gly Asp Ile Phe Gly Ser
                 85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Ala Trp Thr Arg Pro His Lys Ala Gln Val Asp Ser Trp
130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ser Thr Val Arg Ser Arg Ile Thr Ser Ala Gly Ala Gly Gln Gly
        355                 360                 365

Gln Ala Ala Trp Phe Ala Thr Phe Asn Glu Thr Phe Gly Asp Tyr Ala
370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe Asp Val Trp
        435                 440                 445
```

```
Asp Leu Leu Pro Phe Thr Arg Gly Tyr Val His Ile Leu Asp Lys Asp
    450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
            500                 505                 510

Gly Asp Asn Leu Ala Tyr Asp Asp Leu Ser Ala Trp Val Glu Tyr
                515                 520                 525

Ile Pro Tyr Asn Phe Arg Pro Asn Tyr His Gly Val Gly Thr Cys Ser
    530                 535                 540

Met Met Pro Lys Glu Met Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Ser Met Thr Val Phe Tyr Ala Met Ala Leu Lys
            580                 585                 590

Val Ala Asp Ala Ile Leu Ala Asp Tyr Ala Ser Met Gln
                595                 600         605

<210> SEQ ID NO 14
<211> LENGTH: 605
<212> TYPE: PRT
<213> ORGANISM: Aspergillus niger

<400> SEQUENCE: 14

Met Ser Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ile Ala Gly
            35                  40                  45

Gly Gly Leu Thr Gly Leu Thr Thr Ala Ala Arg Leu Thr Glu Asn Pro
        50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Thr Trp Thr Arg Pro His Lys Ala Gln Val Asp Ser Trp
130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
210                 215                 220
```

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
            245                 250                 255

Pro Asn Tyr Gln Arg Pro Asn Leu Gln Val Leu Thr Gly Arg Tyr Val
        260                 265                 270

Gly Lys Val Leu Leu Ser Gln Asn Ala Thr Thr Pro Arg Ala Val Gly
    275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
            325                 330                 335

Asp Thr Val Val Asp Leu Pro Val Gly Leu Asn Leu Gln Asp Gln Ala
        340                 345                 350

Thr Ser Thr Val Arg Ser Arg Ile Thr Ser Ala Gly Ala Gly Gln Gly
    355                 360                 365

Gln Ala Ala Trp Phe Ala Thr Phe Asn Glu Thr Phe Gly Asp Tyr Ala
370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
            405                 410                 415

Gln Tyr Glu Asn Tyr Arg Asp Trp Ile Val Lys Asp Asn Val Ala Tyr
        420                 425                 430

Ser Glu Leu Phe Leu Asp Thr Ala Gly Val Ala Ser Phe His Val Trp
    435                 440                 445

Asp Leu Leu Pro Phe Thr Arg Gly Tyr Val His Ile Leu Asp Lys Asp
450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
            485                 490                 495

Ser Asn Ser Gly Ala Met Gln Thr Tyr Phe Ala Gly Glu Thr Ile Pro
        500                 505                 510

Gly Asp Asn Leu Ala Tyr Asp Ala Asp Leu Ser Ala Trp Val Glu Tyr
    515                 520                 525

Ile Pro Tyr Asn Phe Arg Pro Asn Tyr His Gly Val Gly Thr Cys Ser
530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
            565                 570                 575

Gln Met Ser Ser His Val Met Thr Val Phe Tyr Ala Met Ala Leu Lys
        580                 585                 590

Val Ala Asp Ala Ile Leu Ala Asp Tyr Ala Ser Met Gln
    595                 600                 605

<210> SEQ ID NO 15
<211> LENGTH: 605
<212> TYPE: PRT
<213> ORGANISM: Aspergillus niger

<400> SEQUENCE: 15

```
Met Ser Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Glu Val Ala Gly Arg Thr Val Asp Tyr Ile Ala Gly
            35                  40                  45

Gly Gly Leu Thr Gly Leu Thr Thr Ala Ala Arg Leu Thr Glu Asn Pro
50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
            115                 120                 125

Asn Gly Gly Thr Trp Thr Arg Pro His Lys Ala Gln Val Asp Ser Trp
130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
            195                 200                 205

Lys Ala Leu Met Ser Ala Val Glu Asp Arg Gly Val Pro Thr Lys Lys
210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
            275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Ala
            340                 345                 350

Thr Ser Thr Val Arg Ser Arg Ile Thr Ser Ala Gly Ala Gly Gln Gly
            355                 360                 365

Gln Ala Ala Trp Phe Ala Thr Phe Asn Glu Thr Phe Gly Asp Tyr Ala
370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415
```

```
Gln Tyr Glu Asn Tyr Arg Asp Trp Ile Val Lys Asp Asn Val Ala Tyr
            420                 425                 430
Ser Glu Leu Phe Leu Asp Thr Ala Gly Val Ala Ser Phe Asp Val Trp
            435                 440                 445
Asp Leu Leu Pro Phe Thr Arg Gly Tyr Val His Ile Leu Asp Lys Asp
            450                 455                 460
Pro Tyr Leu Arg His Phe Ala Tyr Asp Pro Gln Tyr Phe Leu Asn Glu
465                 470                 475                 480
Leu Asp Leu Leu Gly Gln Ala Ala Thr Gln Leu Ala Arg Asn Ile
                485                 490                 495
Ser Asn Ser Gly Ala Met Gln Thr Tyr Phe Ala Gly Glu Thr Ile Pro
                500                 505                 510
Gly Asp Asn Leu Ala Tyr Asp Ala Asp Leu Ser Ala Trp Val Glu Tyr
                515                 520                 525
Ile Pro Tyr Asn Phe Arg Pro Asn Tyr His Gly Val Gly Thr Cys Ser
                530                 535                 540
Met Met Pro Lys Glu Met Gly Gly Val Val Asp Asn Ala Ala Arg Val
545                 550                 555                 560
Tyr Gly Val Gln Gly Leu Arg Val Ile Asp Gly Ser Ile Pro Pro Thr
                565                 570                 575
Gln Met Ser Ser His Ser Met Thr Val Phe Tyr Ala Met Ala Leu Lys
                580                 585                 590
Val Ala Asp Ala Ile Leu Ala Asp Tyr Ala Ser Met Gln
                595                 600                 605

<210> SEQ ID NO 16
<211> LENGTH: 605
<212> TYPE: PRT
<213> ORGANISM: Aspergillus niger

<400> SEQUENCE: 16

Met Ser Thr Leu Leu Val Ser Ser Leu Val Val Ser Leu Ala Ala Ala
1               5                   10                  15
Leu Pro His Tyr Ile Arg Ser Asn Gly Ile Glu Ala Ser Leu Leu Thr
                20                  25                  30
Asp Pro Lys Glu Val Ala Gly Arg Thr Val Asp Tyr Ile Ile Ala Gly
            35                  40                  45
Gly Gly Leu Thr Gly Leu Thr Thr Ala Ala Arg Leu Thr Glu Asn Pro
        50                  55                  60
Asp Ile Thr Val Leu Val Ile Glu Ser Gly Ser Tyr Glu Ser Asp Arg
65                  70                  75                  80
Gly Pro Ile Ile Glu Asp Leu Asn Ala Tyr Gly Asp Ile Phe Gly Ser
                85                  90                  95
Ser Val Asp His Ala Tyr Glu Thr Val Glu Leu Ala Thr Asn Asn Gln
                100                 105                 110
Thr Ala Leu Ile Arg Ser Gly Asn Gly Leu Gly Gly Ser Thr Leu Val
            115                 120                 125
Asn Gly Gly Thr Trp Thr Arg Pro His Lys Ala Gln Val Asp Ser Trp
        130                 135                 140
Glu Thr Val Phe Gly Asn Glu Gly Trp Asn Trp Asp Ser Val Ala Ala
145                 150                 155                 160
Tyr Ser Leu Gln Ala Glu Arg Ala Arg Ala Pro Asn Ala Lys Gln Ile
                165                 170                 175
Ala Ala Gly His Tyr Phe Asn Ala Ser Cys His Gly Ile Asn Gly Thr
```

```
            180                 185                 190
Val His Ala Gly Pro Arg Asp Thr Gly Asp Tyr Ser Pro Ile Val
            195                 200                 205

Lys Ala Leu Met Ser Ala Val Glu Asp Arg Gly Val Pro Thr Lys Lys
            210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
            245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
            275                 280                 285

Val Glu Phe Gly Thr His Lys Gly Asn Thr His Asn Val Tyr Ala Lys
            290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
            325                 330                 335

Asp Thr Val Val Asp Leu Pro Val Gly Leu Asn Leu Gln Asp Gln Thr
            340                 345                 350

Thr Ser Thr Val Arg Ser Arg Ile Thr Ser Ala Gly Ala Gly Gln Gly
            355                 360                 365

Gln Ala Ala Trp Phe Ala Thr Phe Asn Glu Thr Phe Gly Asp Tyr Ala
            370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
            405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe His Val Trp
            435                 440                 445

Asp Leu Leu Pro Phe Thr Arg Gly Tyr Val His Ile Leu Asp Lys Asp
            450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
            485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Val Glu Tyr
            515                 520                 525

Ile Pro Tyr Asn Phe Arg Pro Asn Tyr His Gly Val Gly Thr Cys Ser
            530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
            565                 570                 575

Gln Met Ser Ser His Ser Met Thr Val Phe Tyr Ala Met Ala Leu Lys
            580                 585                 590

Val Ala Asp Ala Ile Leu Ala Asp Tyr Ala Ser Met Gln
            595                 600                 605
```

<210> SEQ ID NO 17
<211> LENGTH: 605
<212> TYPE: PRT
<213> ORGANISM: Aspergillus niger

<400> SEQUENCE: 17

```
Met Ser Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Glu Val Ala Gly Arg Thr Val Asp Tyr Ile Ile Ala Gly
        35                  40                  45

Gly Gly Leu Thr Gly Leu Thr Thr Ala Ala Arg Leu Thr Glu Asn Pro
    50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Ala Trp Thr Arg Pro His Lys Ala Gln Val Asp Ser Trp
    130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
    210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
    290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Ala
            340                 345                 350

Thr Ser Thr Val Arg Ser Arg Ile Thr Ser Ala Gly Ala Gly Gln Gly
        355                 360                 365

Gln Ala Ala Trp Phe Ala Thr Phe Asn Glu Thr Phe Gly Asp Tyr Ala
```

```
                    370                 375                 380
Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe His Val Trp
        435                 440                 445

Asp Leu Leu Pro Phe Thr Arg Gly Tyr Val His Ile Leu Asp Lys Asp
    450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Val Glu Tyr
        515                 520                 525

Ile Pro Tyr Asn Phe Arg Pro Asn Tyr His Gly Val Gly Thr Cys Ser
    530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Val Met Thr Val Phe Tyr Ala Met Ala Leu Lys
            580                 585                 590

Val Ala Asp Ala Ile Leu Ala Asp Tyr Ala Ser Met Gln
        595                 600                 605

<210> SEQ ID NO 18
<211> LENGTH: 605
<212> TYPE: PRT
<213> ORGANISM: Aspergillus niger

<400> SEQUENCE: 18

Met Ser Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ala Gly
            35                  40                  45

Gly Gly Leu Thr Gly Leu Thr Thr Ala Ala Arg Leu Thr Glu Asn Pro
        50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Ala Trp Thr Arg Pro His Lys Ala Gln Val Asp Ser Trp
    130                 135                 140
```

```
Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Tyr Ser Pro Ile Val
            195                 200                 205

Lys Ala Leu Met Ser Ala Val Glu Asp Arg Gly Val Pro Thr Lys Lys
        210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Ala
            340                 345                 350

Thr Ser Thr Val Arg Ser Arg Ile Thr Ser Ala Gly Ala Gly Gln Gly
            355                 360                 365

Gln Ala Ala Trp Phe Ala Thr Phe Asn Glu Thr Phe Gly Asp Tyr Ala
        370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe Asp Val Trp
        435                 440                 445

Asp Leu Leu Pro Phe Thr Arg Gly Tyr Val His Ile Leu Asp Lys Asp
450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Thr Gln Leu Ala Arg Asn Ile
            485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Val Glu Tyr
            515                 520                 525

Ile Pro Tyr Asn Phe Arg Pro Asn Tyr His Gly Val Gly Thr Cys Ser
        530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
```

-continued

```
                565                 570                 575
Gln Met Ser Ser His Ser Met Thr Val Phe Tyr Ala Met Ala Leu Lys
                580                 585                 590
Val Ala Asp Ala Ile Leu Ala Asp Tyr Ala Ser Met Gln
                595                 600                 605

<210> SEQ ID NO 19
<211> LENGTH: 605
<212> TYPE: PRT
<213> ORGANISM: Aspergillus niger

<400> SEQUENCE: 19

Met Ser Thr Leu Leu Val Ser Ser Leu Val Ser Leu Ala Ala Ala
1               5                   10                  15
Leu Pro His Tyr Ile Arg Ser Asn Gly Ile Glu Ala Ser Leu Leu Thr
                20                  25                  30
Asp Pro Lys Glu Val Ala Gly Arg Thr Val Asp Tyr Ile Ile Ala Gly
            35                  40                  45
Gly Gly Leu Thr Gly Leu Thr Thr Ala Ala Arg Leu Thr Glu Asn Pro
        50                  55                  60
Asp Ile Thr Val Leu Val Ile Glu Ser Gly Ser Tyr Glu Ser Asp Arg
65                  70                  75                  80
Gly Pro Ile Ile Glu Asp Leu Asn Ala Tyr Gly Asp Ile Phe Gly Ser
                85                  90                  95
Ser Val Asp His Ala Tyr Glu Thr Val Glu Leu Ala Thr Asn Asn Gln
                100                 105                 110
Thr Ala Leu Ile Arg Ser Gly Asn Gly Leu Gly Gly Ser Thr Leu Val
                115                 120                 125
Asn Gly Gly Ala Trp Thr Arg Pro His Lys Ala Gln Val Asp Ser Trp
            130                 135                 140
Glu Thr Val Phe Gly Asn Glu Gly Trp Asn Trp Asp Ser Val Ala Ala
145                 150                 155                 160
Tyr Ser Leu Gln Ala Glu Arg Ala Arg Ala Pro Asn Ala Lys Gln Ile
                165                 170                 175
Ala Ala Gly His Tyr Phe Asn Ala Ser Cys His Gly Ile Asn Gly Thr
                180                 185                 190
Val His Ala Gly Pro Arg Asp Thr Gly Asp Asp Tyr Ser Pro Ile Val
                195                 200                 205
Lys Ala Leu Met Ser Ala Val Glu Asp Arg Gly Val Pro Thr Lys Lys
            210                 215                 220
Asp Leu Gly Cys Gly Asp Pro His Gly Val Ser Met Phe Pro Asn Thr
225                 230                 235                 240
Leu His Glu Asp Gln Val Arg Ser Asp Ala Ala Arg Glu Trp Leu Leu
                245                 250                 255
Pro Asn Tyr Gln Arg Pro Asn Leu Gln Val Leu Thr Gly Arg Tyr Val
                260                 265                 270
Gly Lys Val Leu Leu Ser Gln Asn Ala Thr Thr Pro Arg Ala Val Gly
            275                 280                 285
Val Glu Phe Gly Thr His Lys Gly Asn Thr His Asn Val Tyr Ala Lys
            290                 295                 300
His Glu Val Leu Leu Ala Ala Gly Ser Ala Val Ser Pro Thr Ile Leu
305                 310                 315                 320
Glu Tyr Ser Gly Ile Gly Met Lys Ser Ile Leu Glu Pro Leu Gly Ile
                325                 330                 335
```

```
Asp Thr Val Val Asp Leu Pro Val Gly Leu Asn Leu Gln Asp Gln Thr
            340                 345                 350

Thr Ser Thr Val Arg Ser Arg Ile Thr Ser Ala Gly Ala Gly Gln Gly
        355                 360                 365

Gln Ala Ala Trp Phe Ala Thr Phe Asn Glu Thr Phe Gly Asp Tyr Ala
    370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe His Val Trp
        435                 440                 445

Asp Leu Leu Pro Phe Thr Arg Gly Tyr Val His Ile Leu Asp Lys Asp
    450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Val Glu Tyr
        515                 520                 525

Ile Pro Tyr Asn Phe Arg Pro Asn Tyr His Val Gly Thr Cys Ser
    530                 535                 540

Met Met Pro Lys Glu Met Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Ser Met Thr Val Phe Tyr Ala Met Ala Leu Lys
            580                 585                 590

Val Ala Asp Ala Ile Leu Ala Asp Tyr Ala Ser Met Gln
        595                 600                 605

<210> SEQ ID NO 20
<211> LENGTH: 605
<212> TYPE: PRT
<213> ORGANISM: Aspergillus niger

<400> SEQUENCE: 20

Met Ser Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Glu Val Ala Gly Arg Thr Val Asp Tyr Ile Ile Ala Gly
        35                  40                  45

Gly Gly Leu Thr Gly Leu Thr Thr Ala Ala Arg Leu Thr Glu Asn Pro
    50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110
```

```
Thr Ala Leu Ile Arg Ser Gly Asn Gly Leu Gly Gly Ser Thr Leu Val
        115                 120                 125

Asn Gly Gly Thr Trp Thr Arg Pro His Lys Ala Gln Val Asp Ser Trp
    130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
    210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
    290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Ala
            340                 345                 350

Thr Ser Thr Val Arg Ser Arg Ile Thr Ser Ala Gly Ala Gly Gln Gly
        355                 360                 365

Gln Ala Ala Trp Phe Ala Thr Phe Asn Glu Thr Phe Gly Asp Tyr Ala
    370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe His Val Trp
        435                 440                 445

Asp Leu Leu Pro Phe Thr Arg Gly Tyr Val His Ile Leu Asp Lys Asp
    450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Val Glu Tyr
        515                 520                 525
```

```
Ile Pro Tyr Asn Phe Arg Pro Asn Tyr His Gly Val Gly Thr Cys Ser
    530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Ser Met Thr Val Phe Tyr Ala Met Ala Leu Lys
                580                 585                 590

Val Ala Asp Ala Ile Leu Ala Asp Tyr Ala Ser Met Gln
                595                 600                 605

<210> SEQ ID NO 21
<211> LENGTH: 605
<212> TYPE: PRT
<213> ORGANISM: Aspergillus niger

<400> SEQUENCE: 21

Met Ser Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ala Gly
                35                  40                  45

Gly Gly Leu Thr Gly Leu Thr Thr Ala Ala Arg Leu Thr Glu Asn Pro
    50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
                100                 105                 110

Thr Ala Leu Ile Arg Ser Gly Asn Gly Leu Gly Gly Ser Thr Leu Val
                115                 120                 125

Asn Gly Gly Ala Trp Thr Arg Pro His Lys Ala Gln Val Asp Ser Trp
    130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
                180                 185                 190

Val His Ala Gly Pro Arg Asp Thr Gly Asp Asp Tyr Ser Pro Ile Val
                195                 200                 205

Lys Ala Leu Met Ser Ala Val Glu Asp Arg Gly Val Pro Thr Lys Lys
    210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
                260                 265                 270

Gly Lys Val Leu Leu Ser Gln Asn Ala Thr Thr Pro Arg Ala Val Gly
    275                 280                 285

Val Glu Phe Gly Thr His Lys Gly Asn Thr His Asn Val Tyr Ala Lys
    290                 295                 300
```

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
            325                 330                 335

Asp Thr Val Val Asp Leu Pro Val Gly Leu Asn Leu Gln Asp Gln Ala
        340                 345                 350

Thr Ser Thr Val Arg Ser Arg Ile Thr Ser Ala Gly Ala Gly Gln Gly
    355                 360                 365

Gln Ala Ala Trp Phe Ala Thr Phe Asn Glu Thr Phe Gly Asp Tyr Ala
370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
            405                 410                 415

Gln Tyr Glu Asn Tyr Arg Asp Trp Ile Val Lys Asp Asn Val Ala Tyr
        420                 425                 430

Ser Glu Leu Phe Leu Asp Thr Ala Gly Val Ala Ser Phe His Val Trp
    435                 440                 445

Asp Leu Leu Pro Phe Thr Arg Gly Tyr Val His Ile Leu Asp Lys Asp
450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Thr Gln Leu Ala Arg Asn Ile
            485                 490                 495

Ser Asn Ser Gly Ala Met Gln Thr Tyr Phe Ala Gly Glu Thr Ile Pro
        500                 505                 510

Gly Asp Asn Leu Ala Tyr Asp Ala Asp Leu Ser Ala Trp Val Glu Tyr
    515                 520                 525

Ile Pro Tyr Asn Phe Arg Pro Asn Tyr His Gly Val Gly Thr Cys Ser
530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
            565                 570                 575

Gln Met Ser Ser His Ser Met Thr Val Phe Tyr Ala Met Ala Leu Lys
        580                 585                 590

Val Ala Asp Ala Ile Leu Ala Asp Tyr Ala Ser Met Gln
    595                 600                 605

<210> SEQ ID NO 22
<211> LENGTH: 1818
<212> TYPE: DNA
<213> ORGANISM: Aspergillus niger

<400> SEQUENCE: 22
atgtctactc tccttgtgag ctcgcttgtg gtctccctcg ctgcggccct cccacactac    60
atcaggagca atggcatcga agccagcctc ctgactgacc ccaaggaggt tgccggccgc   120
actgtcgact acatcatcgc tggtggaggt ctgactggac tcaccactgc tgcccgtctg   180
acggagaacc ccgatatcac tgtgcttgtc atcgaaagtg gctcctacga gtctgacaga   240
ggtcctatca ttgaggacct gaacgcttac ggtgacattt ttggcagcag tgtggaccac   300
gcctacgaga ctgtcgagct cgccaccaac aatcagactg cgctgatccg ctccggaaat   360
ggtctcggtg gctctaccct cgtcaacggt ggcgcttgga ctcgccccca caaggcacaa   420

```
gttgactcat gggagaccgt cttcggaaat gagggctgga actgggacag cgtggccgcc     480
tactccctcc aggctgagcg tgctcgcgca ccaaatgcca aacagattgc tgctggccac     540
tactttaatg catcctgcca tggtatcaat ggtactgtcc acgccggacc ccgcgatacc     600
ggtgatgact actcccccat cgtcaaggct ctcatgagcg ctgtcgaaga caggggcgtt     660
cccaccaaga aggacttggg atgcggtgac ccccatggtg tgtccatgtt ccccaacacc     720
ttgcacgaag accaagtgcg ctctgatgcc gctcgtgaat ggctcctccc caactaccag     780
cgtcccaacc tgcaagtcct cactggacgg tatgttggaa aggtcctgct cagccagaac     840
gctaccacac ctcgtgccgt tggcgtggaa ttcggcaccc acaagggcaa cacccacaac     900
gtctacgcta agcacgaggt cctcctggcc gctggatccg ctgtctctcc caccatcctc     960
gaatattccg gtatcggaat gaagtccatt ctagagcctc ttggaattga caccgtcgtt    1020
gacctgcccg ttggtctcaa ccttcaggac cagaccacct ctaccgtccg ctcacgcatt    1080
acctccgccg gtgccggaca gggacaggcc gcttggttcg ctaccttcaa cgagaccttt    1140
ggcgactacg ccgaaaaggc tcacgagctg ctcaacacca gctggagca gtgggccgaa    1200
gaggccgtcg cccgtggcgg attccacaac accaccgctt tgctcatcca gtacgagaac    1260
taccgcgact ggatcgtcaa ggacaatgtc gcatactcgg aactcttcct cgacacggcc    1320
ggagtggcca gtttcgatgt gtgggatctt ctgcccttca ctagaggata cgtacacatc    1380
ctcgacaagg accoctacct ccgccatttc gcatacgacc ctcagtactt tctcaacgag    1440
cttgacctgc tcggccaggc tgccgccact cagctggccc gcaacatctc caactccggt    1500
gccatgcaaa cttatttcgc tggagagact attcccggtg acaacctcgc gtatgatgcc    1560
gacttgagcg cctgggttga gtatatcccg tacaacttcc gccctaacta ccatggtgtg    1620
ggtacttgct ccatgatgcc gaaggagatg ggcggtgttg tcgacaatgc tgcccgtgtg    1680
tatggtgtgc agggactgcg agtcatcgat ggttctattc cccctacgca aatgtcgtcc    1740
catgttatga cggtcttta tgccatggcc ttgaaggttg cggatgccat cttggcggat    1800
tatgcttcca tgcagtga                                                   1818
```

<210> SEQ ID NO 23
<211> LENGTH: 1818
<212> TYPE: DNA
<213> ORGANISM: Aspergillus niger

<400> SEQUENCE: 23

```
atgtctactc tccttgtgag ctcgcttgtg gtctccctcg ctgcggccct cccacactac      60
atcaggagca atggcatcga agccagcctc ctgactgacc ccaaggaggt tgccggccgc     120
actgtcgact acatcatcgc tggtggaggt ctgactggac tcaccactgc tgcccgtctg     180
acggagaacc ccgatatcac tgtgcttgtc atcgaaagtg gctcctacga gtctgacaga     240
ggtcctatca ttgaggacct gaacgcttac ggtgacattt ttggcagcag tgtggaccac     300
gcctacgaga ctgtcgagct cgccaccaac aatcagactg cgctgatccg ctccggaaat     360
ggtctcggtg gctctaccct cgtcaacggt ggcacctgga ctcgccccca caaggcacaa     420
gttgactcat gggagaccgt cttcggaaat gagggctgga actgggacag cgtggccgcc     480
tactccctcc aggctgagcg tgctcgcgca ccaaatgcca aacagattgc tgctggccac     540
tactttaatg catcctgcca tggtatcaat ggtactgtcc acgccggacc ccgcgatacc     600
ggtgatgact actcccccat cgtcaaggct ctcatgagcg ctgtcgaaga caggggcgtt     660
```

```
cccaccaaga aggacttggg atgcggtgac ccccatggtg tgtccatgtt ccccaacacc    720
ttgcacgaag accaagtgcg ctctgatgcc gctcgtgaat ggctcctccc caactaccag    780
cgtcccaacc tgcaagtcct cactggacgg tatgttggaa aggtcctgct cagccagaac    840
gctaccacac ctcgtgccgt tggcgtggaa ttcggcaccc acaagggcaa cacccacaac    900
gtctacgcta agcacgaggt cctcctggcc gctggatccg ctgtctctcc caccatcctc    960
gaatattccg gtatcggaat gaagtccatt ctagagcctc ttggaattga caccgtcgtt   1020
gacctgcccg ttggtctcaa ccttcaggac caggctacct ctaccgtccg ctcacgcatt   1080
acctccgccg gtgccggaca gggacaggcc gcttggttcg ctaccttcaa cgagaccttt   1140
ggcgactacg ccgaaaaggc tcacgagctg ctcaacacca gctggagca gtgggccgaa    1200
gaggccgtcg cccgtggcgg attccacaac accaccgctt tgctcatcca gtacgagaac   1260
taccgcgact ggatcgtcaa ggacaatgtc gcatactcgg aactcttcct cgacacggcc   1320
ggagtggcca gtttcgatgt gtgggatctt ctgcccttca ctagaggata cgtacacatc   1380
ctcgacaagg accccctacct ccgccatttc gcatacgacc ctcagtactt tctcaacgag   1440
cttgacctgc tcggccaggc tgccgccact cagctggccc gcaacatctc caactccggt   1500
gccatgcaaa cttatttcgc tggagagact attcccggtg acaacctcgc gtatgatgcc   1560
gacttgagcg cctgggttga gtatatcccg tacaacttcc gccctaacta ccatggtgtg   1620
ggtacttgct ccatgatgcc gaaggagatg ggcggtgttg tcgacaatgc tgcccgtgtg   1680
tatggtgtgc agggactgcg agtcatcgat ggttctattc cccctacgca aatgtcgtcc   1740
catgttatga cggtcttta tgccatggcc ttgaaggttg cggatgccat cttggcggat   1800
tatgcttcca tgcagtga                                                 1818

<210> SEQ ID NO 24
<211> LENGTH: 1818
<212> TYPE: DNA
<213> ORGANISM: Aspergillus niger

<400> SEQUENCE: 24
atgtctactc tccttgtgag ctcgcttgtg gtctccctcg ctgcggccct cccacactac     60
atcaggagca atggcatcga agccagcctc ctgactgacc ccaaggaggt tgccggccgc    120
actgtcgact acatcatcgc tggtggaggt ctgactggac tcaccactgc tgcccgtctg    180
acggagaacc ccgatatcac tgtgcttgtc atcgaaagtg gctcctacga gtctgacaga    240
ggtcctatca ttgaggacct gaacgcttac ggtgacattt ttggcagcag tgtgaccac    300
gcctacgaga ctgtcgagct cgccaccaac aatcagactg cgctgatccg ctccggaaat    360
ggtctcggtg gctctacccct cgtcaacggt ggcacctgga ctcgccccca caaggcacaa    420
gttgactcat gggagaccgt cttcggaaat gagggctgga actgggacag cgtggccgcc    480
tactccctcc aggctgagcg tgctcgcgca ccaaatgcca aacagattgc tgctggccac    540
tactttaatg catcctgcca tggtatcaat ggtactgtcc acgccggacc ccgcgatacc    600
ggtgatgact actccccccat cgtcaaggct ctcatgagcg ctgtcgaaga caggggcgtt    660
cccaccaaga aggacttggg atgcggtgac ccccatggtg tgtccatgtt ccccaacacc    720
ttgcacgaag accaagtgcg ctctgatgcc gctcgtgaat ggctcctccc caactaccag    780
cgtcccaacc tgcaagtcct cactggacgg tatgttggaa aggtcctgct cagccagaac    840
gctaccacac ctcgtgccgt tggcgtggaa ttcggcaccc acaagggcaa cacccacaac    900
gtctacgcta agcacgaggt cctcctggcc gctggatccg ctgtctctcc caccatcctc    960
```

```
gaatattccg gtatcggaat gaagtccatt ctagagcctc ttggaattga caccgtcgtt    1020
gacctgcccg ttggtctcaa ccttcaggac cagaccacct ctaccgtccg ctcacgcatt    1080
acctccgccg gtgccggaca gggacaggcc gcttggttcg ctaccttcaa cgagaccttt    1140
ggcgactacg ccgaaaaggc tcacgagctg ctcaacacca agctggagca gtgggccgaa    1200
gaggccgtcg cccgtggcgg attccacaac accaccgctt tgctcatcca gtacgagaac    1260
taccgcgact ggatcgtcaa ggacaatgtc gcatactcgg aactcttcct cgacacggcc    1320
ggagtggcca gtttccatgt gtgggatctt ctgcccttca ctagaggata cgtacacatc    1380
ctcgacaagg acccctacct ccgccatttc gcatacgacc ctcagtactt tctcaacgag    1440
cttgacctgc tcggccaggc tgccgccact cagctggccc gcaacatctc caactccggt    1500
gccatgcaaa cttatttcgc tggagagact attcccggtg acaacctcgc gtatgatgcc    1560
gacttgagcg cctgggttga gtatatcccg tacaacttcc gccctaacta ccatggtgtg    1620
ggtacttgct ccatgatgcc gaaggagatg ggcggtgttg tcgacaatgc tgcccgtgtg    1680
tatggtgtgc agggactgcg agtcatcgat ggttctattc cccctacgca aatgtcgtcc    1740
catgttatga cggtcttta tgccatggcc ttgaaggttg cggatgccat cttggcggat    1800
tatgcttcca tgcagtga                                                 1818

<210> SEQ ID NO 25
<211> LENGTH: 1818
<212> TYPE: DNA
<213> ORGANISM: Aspergillus niger

<400> SEQUENCE: 25
atgtctactc tccttgtgag ctcgcttgtg gtctccctcg ctgcggccct cccacactac     60
atcaggagca atggcatcga agccagcctc ctgactgacc caaggaggt tgccggccgc    120 actgtcgact acatcatcgc tggtggaggt ctgactggac tcaccactgc tgcccgtctg    180
acggagaacc ccgatatcac tgtgcttgtc atcgaaagtg gctcctacga gtctgacaga    240
ggtcctatca ttgaggacct gaacgcttac ggtgacattt ttggcagcag tgtggaccac    300
gcctacgaga ctgtcgagct cgccaccaac aatcagactg cgctgatccg ctccggaaat    360
ggtctcggtg gctctaccct cgtcaacggt ggcacctgga ctcgccccca caaggcacaa    420
gttgactcat gggagaccgt cttcggaaat gagggctgga ctgggacag cgtggccgcc    480 tactccctcc aggctgagcg tgctcgcgca ccaaatgcca aacagattgc tgctggccac    540
tactttaatg catcctgcca tggtatcaat ggtactgtcc acgccggacc ccgcgatacc    600
ggtgatgact actcccccat cgtcaaggct ctcatgagcg ctgtcgaaga caggggcgtt    660
cccaccaaga aggacttggg atgcggtgac ccccatggtg tgtccatgtt ccccaacacc    720
ttgcacgaag accaagtgcg ctctgatgcc gctcgtgaat ggctcctccc caactaccag    780
cgtcccaacc tgcaagtcct cactggacgg tatgttggaa aggtcctgct cagccagaac    840
gctaccacac tcgtgccgt tggcgtggaa ttcggcaccc acaagggcaa cacccacaac    900
gtctacgcta agcacgaggt cctcctggcc gctggatccg ctgtctctcc caccatcctc    960
gaatattccg gtatcggaat gaagtccatt ctagagcctc ttggaattga caccgtcgtt   1020
gacctgcccg ttggtctcaa ccttcaggac cagaccacct ctaccgtccg ctcacgcatt   1080
acctccgccg gtgccggaca gggacaggcc gcttggttcg ctaccttcaa cgagaccttt   1140
ggcgactacg ccgaaaaggc tcacgagctg ctcaacacca agctggagca gtgggccgaa   1200
```

```
gaggccgtcg cccgtggcgg attccacaac accaccgctt tgctcatcca gtacgagaac    1260
taccgcgact ggatcgtcaa ggacaatgtc gcatactcgg aactcttcct cgacacggcc    1320
ggagtggcca gtttcgatgt gtgggatctt ctgcccttca ctagaggata cgtacacatc    1380
ctcgacaagg acccctacct ccgccatttc gcatacgacc ctcagtactt tctcaacgag    1440
cttgacctgc tcggccaggc tgccgccact cagctggccc gcaacatctc caactccggt    1500
gccatgcaaa cttatttcgc tggagagact attcccggtg acaacctcgc gtatgatgcc    1560
gacttgagcg cctgggttga gtatatcccg tacaacttcc gccctaacta ccatggtgtg    1620
ggtacttgct ccatgatgcc gaaggagatg ggcggtgttg tcgacaatgc tgcccgtgtg    1680
tatggtgtgc agggactgcg agtcatcgat ggttctattc ccctacgca aatgtcgtcc    1740 cattctatga cggtctttta tgccatggcc ttgaaggttg cggatgccat cttggcggat    1800
tatgcttcca tgcagtga                                                 1818

<210> SEQ ID NO 26
<211> LENGTH: 1818
<212> TYPE: DNA
<213> ORGANISM: Aspergillus niger

<400> SEQUENCE: 26
atgtctactc tccttgtgag ctcgcttgtg gtctccctcg ctgcggccct cccacactac     60
atcaggagca atggcatcga agccagcctc ctgactgacc ccaaggaggt tgccggccgc    120
actgtcgact acatcatcgc tggtggaggt ctgactggac tcaccactgc tgcccgtctg    180
acggagaacc ccgatatcac tgtgcttgtc atcgaaagtg gctcctacga gtctgacaga    240
ggtcctatca ttgaggacct gaacgcttac ggtgacattt ttggcagcag tgtggaccac    300
gcctacgaga ctgtcgagct cgccaccaac aatcagactg cgctgatccg ctccggaaat    360
ggtctcggtg gctctaccct cgtcaacggt ggcgcttgga ctcgccccca caaggcacaa    420
gttgactcat gggagaccgt cttcggaaat gagggctgga actgggacag cgtggccgcc    480
tactccctcc aggctgagcg tgctcgcgca ccaaatgcca acagattgc tgctggccac    540 tactttaatg catcctgcca tggtatcaat ggtactgtcc acgccggacc ccgcgatacc    600
ggtgatgact actccccat cgtcaaggct ctcatgagcg ctgtcgaaga cagggcgtt    660 cccaccaaga aggacttggg atgcggtgac ccccatggtg tgtccatgtt ccccaacacc    720
ttgcacgaag accaagtgcg ctctgatgcc gctcgtgaat ggctcctccc caactaccag    780
cgtcccaacc tgcaagtcct cactggacgg tatgttggaa aggtcctgct cagccagaac    840
gctaccacac ctcgtgccgt tggcgtggaa ttcggcaccc acaagggcaa cacccacaac    900
gtctacgcta agcacgaggt cctcctggcc gctggatccg ctgtctctcc caccatcctc    960
gaatattccg gtatcggaat gaagtccatt ctagagcctc ttggaattga caccgtcgtt   1020
gacctgcccg ttggtctcaa ccttcaggac caggctacct ctaccgtccg ctcacgcatt   1080
acctccgccg gtgccggaca gggacaggcc gcttggttcg ctaccttcaa cgagaccttt   1140
ggcgactacg ccgaaaaggc tcacgagctg ctcaacacca gctggagca gtgggccgaa   1200 gaggccgtcg cccgtggcgg attccacaac accaccgctt tgctcatcca gtacgagaac   1260
taccgcgact ggatcgtcaa ggacaatgtc gcatactcgg aactcttcct cgacacggcc   1320
ggagtggcca gtttcgatgt gtgggatctt ctgcccttca ctagaggata cgtacacatc   1380
ctcgacaagg acccctacct ccgccatttc gcatacgacc ctcagtactt tctcaacgag   1440
cttgacctgc tcggccaggc tgccgccact cagctggccc gcaacatctc caactccggt   1500
```

| | |
|---|---|
| gccatgcaaa cttatttcgc tggagagact attcccggtg acaacctcgc gtatgatgcc | 1560 |
| gacttgagcg cctgggttga gtatatcccg tacaacttcc gccctaacta ccatggtgtg | 1620 |
| ggtacttgct ccatgatgcc gaaggagatg ggcggtgttg tcgacaatgc tgcccgtgtg | 1680 |
| tatggtgtgc agggactgcg agtcatcgat ggttctattc cccctacgca aatgtcgtcc | 1740 |
| catgttatga cggtctttta tgccatggcc ttgaaggttg cggatgccat cttggcggat | 1800 |
| tatgcttcca tgcagtga | 1818 |

<210> SEQ ID NO 27
<211> LENGTH: 1818
<212> TYPE: DNA
<213> ORGANISM: Aspergillus niger

<400> SEQUENCE: 27

| | |
|---|---|
| atgtctactc tccttgtgag ctcgcttgtg gtctccctcg ctgcggccct cccacactac | 60 |
| atcaggagca atggcatcga agccagcctc ctgactgacc caaggaggt tgccggccgc | 120 |
| actgtcgact acatcatcgc tggtggaggt ctgactggac tcaccactgc tgcccgtctg | 180 |
| acggagaacc ccgatatcac tgtgcttgtc atcgaaagtg ctcctacga gtctgacaga | 240 |
| ggtcctatca ttgaggacct gaacgcttac ggtgacattt ttggcagcag tgtggaccac | 300 |
| gcctacgaga ctgtcgagct cgccaccaac aatcagactg cgctgatccg ctccggaaat | 360 |
| ggtctcggtg gctctaccct cgtcaacggt ggcgcttgga ctcgccccca caaggcacaa | 420 |
| gttgactcat gggagaccgt cttcggaaat gagggctgga actgggacag cgtggccgcc | 480 |
| tactccctcc aggctgagcg tgctcgcgca ccaaatgcca aacagattgc tgctggccac | 540 |
| tactttaatg catcctgcca tggtatcaat ggtactgtcc acgccggacc ccgcgatacc | 600 |
| ggtgatgact actcccccat cgtcaaggct ctcatgagcg ctgtcgaaga caggggcgtt | 660 |
| cccaccaaga aggacttggg atgcggtgac ccccatggtg tgtccatgtt ccccaacacc | 720 |
| ttgcacgaag accaagtgcg ctctgatgcc gctcgtgaat ggctcctccc caactaccag | 780 |
| cgtcccaacc tgcaagtcct cactggacgg tatgttggaa aggtcctgct cagccagaac | 840 |
| gctaccacac tcgtgccgt tggcgtggaa ttcggcaccc acaagggcaa cacccacaac | 900 |
| gtctacgcta agcacgaggt cctcctggcc gctggatccg ctgtctctcc caccatcctc | 960 |
| gaatattccg gtatcggaat gaagtccatt ctagagcctc ttggaattga caccgtcgtt | 1020 |
| gacctgcccg ttggtctcaa ccttcaggac cagaccacct ctaccgtccg ctcacgcatt | 1080 |
| acctccgccg tgccggaca gggacaggcc gcttggttcg ctaccttcaa cgagacctttt | 1140 |
| ggcgactacg ccgaaaaggc tcacgagctg ctcaacacca gctggagca gtgggccgaa | 1200 |
| gaggccgtcg cccgtggcgg attccacaac accaccgctt tgctcatcca gtacgagaac | 1260 |
| taccgcgact ggatcgtcaa ggacaatgtc gcatactcgg aactcttcct cgacacggcc | 1320 |
| ggagtggcca gtttccatgt gtgggatctt ctgcccttca ctagaggata cgtacacatc | 1380 |
| ctcgacaagg acccctacct ccgccatttc gcatacgacc ctcagtactt tctcaacgag | 1440 |
| cttgacctgc tcggccaggc tgccgccact cagctggccc gcaacatctc caactccggt | 1500 |
| gccatgcaaa cttatttcgc tggagagact attcccggtg acaacctcgc gtatgatgcc | 1560 |
| gacttgagcg cctgggttga gtatatcccg tacaacttcc gccctaacta ccatggtgtg | 1620 |
| ggtacttgct ccatgatgcc gaaggagatg ggcggtgttg tcgacaatgc tgcccgtgtg | 1680 |
| tatggtgtgc agggactgcg agtcatcgat ggttctattc cccctacgca aatgtcgtcc | 1740 |

```
catgttatga cggtctttta tgccatggcc ttgaaggttg cggatgccat cttggcggat    1800
tatgcttcca tgcagtga                                                  1818

<210> SEQ ID NO 28
<211> LENGTH: 1818
<212> TYPE: DNA
<213> ORGANISM: Aspergillus niger

<400> SEQUENCE: 28
atgtctactc tccttgtgag ctcgcttgtg gtctccctcg ctgcggccct cccacactac      60
atcaggagca atggcatcga agccagcctc ctgactgacc caaggaggt tgccggccgc     120 actgtcgact acatcatcgc tggtggaggt ctgactggac tcaccactgc tgcccgtctg    180
acggagaacc ccgatatcac tgtgcttgtc atcgaaagtg gctcctacga gtctgacaga    240
ggtcctatca ttgaggacct gaacgcttac ggtgacattt ttggcagcag tgtggaccac    300
gcctacgaga ctgtcgagct cgccaccaac aatcagactg cgctgatccg ctccggaaat    360
ggtctcggtg gctctaccct cgtcaacggt ggcgcttgga ctcgccccca caaggcacaa    420
gttgactcat gggagaccgt cttcggaaat gagggctgga actgggacag cgtggccgcc    480
tactccctcc aggctgagcg tgctcgcgca ccaaatgcca aacagattgc tgctggccac    540
tactttaatg catcctgcca tggtatcaat ggtactgtcc acgccggacc ccgcgatacc    600
ggtgatgact actcccccat cgtcaaggct ctcatgagcg ctgtcgaaga caggggcgtt    660
cccaccaaga aggacttggg atgcggtgac ccccatggtg tgtccatgtt ccccaacacc    720
ttgcacgaag accaagtgcg ctctgatgcc gctcgtgaat ggctcctccc caactaccag    780
cgtcccaacc tgcaagtcct cactggacgg tatgttggaa aggtcctgct cagccagaac    840
gctaccacac tcgtgccgt tggcgtgaaa ttcggcaccc acaagggcaa cacccacaac    900
gtctacgcta agcacgaggt cctcctggcc gctggatccg ctgtctctcc caccatcctc    960
gaatattccg gtatcggaat gaagtccatt ctagagcctc ttggaattga caccgtcgtt   1020
gacctgcccg ttggtctcaa ccttcaggac cagaccacct ctaccgtccg ctcacgcatt   1080
acctccgccg gtgccggaca gggacaggcc gcttggttcg ctaccttcaa cgagaccttt   1140
ggcgactacg ccgaaaaggc tcacgagctg ctcaacacca agctggagca gtgggccgaa   1200
gaggccgtcg cccgtggcgg attccacaac accaccgctt tgctcatcca gtacgagaac   1260
taccgcgact ggatcgtcaa ggacaatgtc gcatactcgg aactcttcct cgacacggcc   1320
ggagtggcca gtttcgatgt gtgggatctt ctgcccttca ctagaggata cgtacacatc   1380
ctcgacaagg accctacct ccgccatttc gcatacgacc ctcagtactt tctcaacgag   1440
cttgacctgc tcggccaggc tgccgccact cagctggccc gcaacatctc caactccggt   1500
gccatgcaaa cttatttcgc tggagagact attcccggtg acaacctcgc gtatgatgcc   1560
gacttgagcg cctgggttga gtatatcccg tacaacttcc gccctaacta ccatggtgtg   1620
ggtacttgct ccatgatgcc gaaggagatg ggcggtgttg tcgacaatgc tgcccgtgtg   1680
tatggtgtgc agggactgcg agtcatcgat ggttctattc ccctacgca aatgtcgtcc   1740 cattctatga cggtctttta tgccatggcc ttgaaggttg cggatgccat cttggcggat   1800
tatgcttcca tgcagtga                                                 1818

<210> SEQ ID NO 29
<211> LENGTH: 1818
<212> TYPE: DNA
<213> ORGANISM: Aspergillus niger
```

<400> SEQUENCE: 29

```
atgtctactc tccttgtgag ctcgcttgtg gtctccctcg ctgcggccct cccacactac      60
atcaggagca atggcatcga agccagcctc ctgactgacc ccaaggaggt tgccggccgc     120
actgtcgact acatcatcgc tggtggaggt ctgactggac tcaccactgc tgcccgtctg     180
acggagaacc ccgatatcac tgtgcttgtc atcgaaagtg gctcctacga gtctgacaga     240
ggtcctatca ttgaggacct gaacgcttac ggtgacattt ttggcagcag tgtgaccac      300
gcctacgaga ctgtcgagct cgccaccaac aatcagactg cgctgatccg ctccggaaat     360
ggtctcggtg ctctaccct cgtcaacggt ggcacctgga ctcgccccca caaggcacaa      420
gttgactcat gggagaccgt cttcggaaat gagggctgga actgggacag cgtggccgcc     480
tactccctcc aggctgagcg tgctcgcgca ccaaatgcca acagattgc tgctggccac      540
tactttaatg catcctgcca tggtatcaat ggtactgtcc acgccggacc ccgcgatacc     600
ggtgatgact actcccccat cgtcaaggct ctcatgagcg ctgtcgaaga caggggcgtt     660
cccaccaaga aggacttggg atgcggtgac ccccatggtg tgtccatgtt ccccaacacc     720
ttgcacgaag accaagtgcg ctctgatgcc gctcgtgaat ggctcctccc caactaccag     780
cgtcccaacc tgcaagtcct cactggacgg tatgttggaa aggtcctgct cagccagaac     840
gctaccacac ctcgtgccgt tggcgtggaa ttcggcaccc acaagggcaa cccacacaac    900
gtctacgcta agcacgaggt cctcctggcc gctggatccg ctgtctctcc caccatcctc    960
gaatattccg gtatcggaat gaagtccatt ctagagcctc ttggaattga caccgtcgtt   1020
gacctgcccg ttggtctcaa ccttcaggac caggctacct ctaccgtccg ctcacgcatt   1080
acctccgccg gtgccggaca gggacaggcc gcttggttcg ctaccttcaa cgagacccttt  1140
ggcgactacg ccgaaaaggc tcacgagctg ctcaacacca gctggagca gtgggccgaa    1200
gaggccgtcg cccgtggcgg attccacaac accaccgctt tgctcatcca gtacgagaac   1260
taccgcgact ggatcgtcaa ggacaatgtc gcatactcgg aactcttcct cgacacggcc   1320
ggagtggcca gtttccatgt gtgggatctt ctgcccttca ctagaggata cgtacacatc   1380
ctcgacaagg acccctacct ccgccatttc gcatacgacc tcagtactt tctcaacgag   1440
cttgacctgc tcggccaggc tgccgccact cagctggccc gcaacatctc caactccggt   1500
gccatgcaaa cttatttcgc tggagagact attcccggtg acaacctcgc gtatgatgcc   1560
gacttgagcg cctgggttga gtatatcccg tacaacttcc gccctaacta ccatggtgtg   1620
ggtacttgct ccatgatgcc gaaggagatg ggcggtgttg tcgacaatgc tgcccgtgtg   1680
tatggtgtgc agggactgcg agtcatcgat ggttctattc cccctacgca aatgtcgtcc   1740
catgttatga cggtcttta tgccatggcc ttgaaggttg cggatgccat cttggcggat   1800
tatgcttcca tgcagtga                                                   1818
```

<210> SEQ ID NO 30
<211> LENGTH: 1818
<212> TYPE: DNA
<213> ORGANISM: Aspergillus niger

<400> SEQUENCE: 30

```
atgtctactc tccttgtgag ctcgcttgtg gtctccctcg ctgcggccct cccacactac      60
atcaggagca atggcatcga agccagcctc ctgactgacc ccaaggaggt tgccggccgc     120
actgtcgact acatcatcgc tggtggaggt ctgactggac tcaccactgc tgcccgtctg     180
```

-continued

| | |
|---|---|
| acggagaacc ccgatatcac tgtgcttgtc atcgaaagtg gctcctacga gtctgacaga | 240 |
| ggtcctatca ttgaggacct gaacgcttac ggtgacattt ttggcagcag tgtggaccac | 300 |
| gcctacgaga ctgtcgagct cgccaccaac aatcagactg cgctgatccg ctccggaaat | 360 |
| ggtctcggtg gctctaccct cgtcaacggt ggcacctgga ctcgccccca caaggcacaa | 420 |
| gttgactcat gggagaccgt cttcggaaat gagggctgga actgggacag cgtggccgcc | 480 |
| tactcccctcc aggctgagcg tgctcgcgca ccaaatgcca acagattgc tgctggccac | 540 |
| tactttaatg catcctgcca tggtatcaat ggtactgtcc acgccggacc ccgcgatacc | 600 |
| ggtgatgact actcccccat cgtcaaggct ctcatgagcg ctgtcgaaga caggggcgtt | 660 |
| cccaccaaga aggacttggg atgcggtgac ccccatggtg tgtccatgtt ccccaacacc | 720 |
| ttgcacgaag accaagtgcg ctctgatgcc gctcgtgaat ggctcctccc caactaccag | 780 |
| cgtcccaacc tgcaagtcct cactggacgg tatgttggaa aggtcctgct cagccagaac | 840 |
| gctaccacac ctcgtgccgt tggcgtggaa ttcggcaccc acaagggcaa cccccacaac | 900 |
| gtctacgcta agcacgaggt cctcctggcc gctggatccg ctgtctctcc caccatcctc | 960 |
| gaatattccg gtatcggaat gaagtccatt ctagagcctc ttggaattga caccgtcgtt | 1020 |
| gacctgcccg ttggtctcaa ccttcaggac caggctacct ctaccgtccg ctcacgcatt | 1080 |
| acctccgccg gtgccggaca gggacaggcc gcttggttcg ctaccttcaa cgagaccttt | 1140 |
| ggcgactacg ccgaaaaggc tcacgagctg ctcaacacca agctggagca gtgggccgaa | 1200 |
| gaggccgtcg cccgtggcgg attccacaac accaccgctt tgctcatcca gtacgagaac | 1260 |
| taccgcgact ggatcgtcaa ggacaatgtc gcatactcgg aactcttcct cgacacggcc | 1320 |
| ggagtggcca gtttcgatgt gtgggatctt ctgcccttca ctagaggata cgtacacatc | 1380 |
| ctcgacaagg accctacct ccgccatttc gcatacgacc ctcagtactt tctcaacgag | 1440 |
| cttgacctgc tcggccaggc tgccgccact cagctggccc gcaacatctc caactccggt | 1500 |
| gccatgcaaa cttatttcgc tggagagact attcccggtg acaacctcgc gtatgatgcc | 1560 |
| gacttgagcg cctgggttga gtatatcccg tacaacttcc gccctaacta ccatggtgtg | 1620 |
| ggtacttgct ccatgatgcc gaaggagatg ggcggtgttg tcgacaatgc tgcccgtgtg | 1680 |
| tatggtgtgc agggactgcg agtcatcgat ggttctattc cccctacgca aatgtcgtcc | 1740 |
| cattctatga cggtcttta tgccatggcc ttgaaggttg cggatgccat cttggcggat | 1800 |
| tatgcttcca tgcagtga | 1818 |

<210> SEQ ID NO 31
<211> LENGTH: 1818
<212> TYPE: DNA
<213> ORGANISM: Aspergillus niger

<400> SEQUENCE: 31

| | |
|---|---|
| atgtctactc tccttgtgag ctcgcttgtg gtctccctcg ctgcggccct cccacactac | 60 |
| atcaggagca atggcatcga agccagcctc ctgactgacc ccaaggaggt tgccggccgc | 120 |
| actgtcgact acatcatcgc tggtggaggt ctgactggac tcaccactgc tgcccgtctg | 180 |
| acggagaacc ccgatatcac tgtgcttgtc atcgaaagtg gctcctacga gtctgacaga | 240 |
| ggtcctatca ttgaggacct gaacgcttac ggtgacattt ttggcagcag tgtggaccac | 300 |
| gcctacgaga ctgtcgagct cgccaccaac aatcagactg cgctgatccg ctccggaaat | 360 |
| ggtctcggtg gctctaccct cgtcaacggt ggcacctgga ctcgccccca caaggcacaa | 420 |
| gttgactcat gggagaccgt cttcggaaat gagggctgga actgggacag cgtggccgcc | 480 |

```
tactccctcc aggctgagcg tgctcgcgca ccaaatgcca aacagattgc tgctggccac    540
tactttaatg catcctgcca tggtatcaat ggtactgtcc acgccggacc ccgcgatacc    600
ggtgatgact actcccccat cgtcaaggct ctcatgagcg ctgtcgaaga caggggcgtt    660
cccaccaaga aggacttggg atgcggtgac ccccatggtg tgtccatgtt ccccaacacc    720
ttgcacgaag accaagtgcg ctctgatgcc gctcgtgaat ggctcctccc caactaccag    780
cgtcccaacc tgcaagtcct cactggacgg tatgttggaa aggtcctgct cagccagaac    840
gctaccacac ctcgtgccgt tggcgtggaa ttcggcaccc acaagggcaa cacccacaac    900
gtctacgcta agcacgaggt cctcctggcc gctggatccg ctgtctctcc caccatcctc    960
gaatattccg gtatcggaat gaagtccatt ctagagcctc ttggaattga caccgtcgtt   1020
gacctgcccg ttggtctcaa ccttcaggac cagaccacct ctaccgtccg ctcacgcatt   1080
acctccgccg gtgccggaca gggacaggcc gcttggttcg ctaccttcaa cgagaccttt   1140
ggcgactacg ccgaaaaggc tcacgagctg ctcaacacca agctggagca gtgggccgaa   1200
gaggccgtcg cccgtggcgg attccacaac accaccgctt tgctcatcca gtacgagaac   1260
taccgcgact ggatcgtcaa ggacaatgtc gcatactcgg aactcttcct cgacacggcc   1320
ggagtggcca gtttccatgt gtgggatctt ctgcccttca ctagaggata cgtacacatc   1380
ctcgacaagg acccctacct ccgccatttc gcatacgacc tcagtacttt tctcaacgag   1440
cttgacctgc tcggccaggc tgccgccact cagctggccc gcaacatctc caactccggt   1500
gccatgcaaa cttatttcgc tggagagact attcccggtg acaacctcgc gtatgatgcc   1560
gacttgagcg cctgggttga gtatatcccg tacaacttcc gccctaacta ccatggtgtg   1620
ggtacttgct ccatgatgcc gaaggagatg ggcggtgttg tcgacaatgc tgcccgtgtg   1680
tatggtgtgc agggactgcg agtcatcgat ggttctattc cccctacgca aatgtcgtcc   1740
cattctatga cggtcttttta tgccatggcc ttgaaggttg cggatgccat cttggcggat   1800
tatgcttcca tgcagtga                                                 1818
```

<210> SEQ ID NO 32
<211> LENGTH: 1818
<212> TYPE: DNA
<213> ORGANISM: Aspergillus niger

<400> SEQUENCE: 32

```
atgtctactc tccttgtgag ctcgcttgtg gtctccctcg ctgcggccct cccacactac     60
atcaggagca atggcatcga agccagcctc ctgactgacc ccaaggaggt tgccggccgc    120
actgtcgact acatcatcgc tggtggaggt ctgactggac tcaccactgc tgcccgtctg    180
acggagaacc ccgatatcac tgtgcttgtc atcgaaagtg ctcctacga gtctgacaga    240 ggtcctatca ttgaggacct gaacgcttac ggtgacattt ttggcagcag tgtggaccac    300
gcctacgaga ctgtcgagct cgccaccaac aatcagactg cgctgatccg ctccggaaat    360
ggtctcggtg gctctaccct cgtcaacggt ggcgcttgga ctcgccccca caaggcacaa    420
gttgactcat gggagaccgt cttcggaaat gagggctgga actgggacag cgtggccgcc    480
tactccctcc aggctgagcg tgctcgcgca ccaaatgcca aacagattgc tgctggccac    540
tactttaatg catcctgcca tggtatcaat ggtactgtcc acgccggacc ccgcgatacc    600
ggtgatgact actcccccat cgtcaaggct ctcatgagcg ctgtcgaaga caggggcgtt    660
cccaccaaga aggacttggg atgcggtgac ccccatggtg tgtccatgtt ccccaacacc    720
```

```
ttgcacgaag accaagtgcg ctctgatgcc gctcgtgaat ggctcctccc caactaccag    780
cgtcccaacc tgcaagtcct cactggacgg tatgttggaa aggtcctgct cagccagaac    840
gctaccacac ctcgtgccgt tggcgtggaa ttcggcaccc acaagggcaa cacccacaac    900
gtctacgcta agcacgaggt cctcctggcc gctggatccg ctgtctctcc caccatcctc    960
gaatattccg gtatcggaat gaagtccatt ctagagcctc ttggaattga caccgtcgtt   1020
gacctgcccg ttggtctcaa ccttcaggac caggctacct ctaccgtccg ctcacgcatt   1080
acctccgccg gtgccggaca gggacaggcc gcttggttcg ctaccttcaa cgagaccttt   1140
ggcgactacg ccgaaaaggc tcacgagctg ctcaacacca agctggagca gtgggccgaa   1200
gaggccgtcg cccgtggcgg attccacaac accaccgctt tgctcatcca gtacgagaac   1260
taccgcgact ggatcgtcaa ggacaatgtc gcatactcgg aactcttcct cgacacggcc   1320
ggagtggcca gtttccatgt gtgggatctt ctgcccttca ctagaggata cgtacacatc   1380
ctcgacaagg accctacct ccgccatttc gcatacgacc ctcagtactt tctcaacgag   1440
cttgacctgc tcggccaggc tgccgccact cagctggccc gcaacatctc caactccggt   1500
gccatgcaaa cttatttcgc tggagagact attcccggtg acaacctcgc gtatgatgcc   1560
gacttgagcg cctgggttga gtatatcccg tacaacttcc gccctaacta ccatggtgtg   1620
ggtacttgct ccatgatgcc gaaggagatg ggcggtgttg tcgacaatgc tgcccgtgtg   1680
tatggtgtgc agggactgcg agtcatcgat ggttctattc cccctacgca aatgtcgtcc   1740
catgttatga cggtcttttta tgccatggcc ttgaaggttg cggatgccat cttggcggat   1800
tatgcttcca tgcagtga                                                 1818

<210> SEQ ID NO 33
<211> LENGTH: 1818
<212> TYPE: DNA
<213> ORGANISM: Aspergillus niger

<400> SEQUENCE: 33
atgtctactc tccttgtgag ctcgcttgtg gtctccctcg ctgcggccct cccacactac     60
atcaggagca atggcatcga agccagcctc ctgactgacc ccaaggaggt tgccggccgc    120
actgtcgact acatcatcgc tggtggaggt ctgactggac tcaccactgc tgcccgtctg    180
acggagaacc ccgatatcac tgtgcttgtc atcgaaagtg gctcctacga gtctgacaga    240
ggtcctatca ttgaggacct gaacgcttac ggtgacattt ttggcagcag tgtggaccac    300
gcctacgaga ctgtcgagct cgccaccaac aatcagactg cgctgatccg ctccggaaat    360
ggtctcggtg gctctaccct cgtcaacggt ggcgcttgga ctcgccccca caaggcacaa    420
gttgactcat gggagaccgt cttcggaaat gagggctgga actgggacag cgtggccgcc    480
tactccctcc aggctgagcg tgctcgcgca ccaaatgcca acagattgc tgctggccac    540
tactttaatg catcctgcca tggtatcaat ggtactgtcc acgccggacc ccgcgatacc    600
ggtgatgact actccccat cgtcaaggct ctcatgagcg ctgtcgaaga caggggcgtt    660
cccaccaaga aggacttggg atgcggtgac ccccatggtg tgtccatgtt ccccaacacc    720
ttgcacgaag accaagtgcg ctctgatgcc gctcgtgaat ggctcctccc caactaccag    780
cgtcccaacc tgcaagtcct cactggacgg tatgttggaa aggtcctgct cagccagaac    840
gctaccacac ctcgtgccgt tggcgtggaa ttcggcaccc acaagggcaa cacccacaac    900
gtctacgcta agcacgaggt cctcctggcc gctggatccg ctgtctctcc caccatcctc    960
gaatattccg gtatcggaat gaagtccatt ctagagcctc ttggaattga caccgtcgtt   1020
```

```
gacctgcccg ttggtctcaa ccttcaggac caggctacct ctaccgtccg ctcacgcatt    1080
acctccgccg gtgccggaca gggacaggcc gcttggttcg ctaccttcaa cgagaccttt    1140
ggcgactacg ccgaaaaggc tcacgagctg ctcaacacca agctggagca gtgggccgaa    1200
gaggccgtcg cccgtggcgg attccacaac accaccgctt tgctcatcca gtacgagaac    1260
taccgcgact ggatcgtcaa ggacaatgtc gcatactcgg aactcttcct cgacacggcc    1320
ggagtggcca gtttcgatgt gtgggatctt ctgcccttca ctagaggata cgtacacatc    1380
ctcgacaagg acccctacct ccgccatttc gcatacgacc ctcagtactt tctcaacgag    1440
cttgacctgc tcggccaggc tgccgccact cagctggccc gcaacatctc caactccggt    1500
gccatgcaaa cttatttcgc tggagagact attcccggtg acaacctcgc gtatgatgcc    1560
gacttgagcg cctgggttga gtatatcccg tacaacttcc gccctaacta ccatggtgtg    1620
ggtacttgct ccatgatgcc gaaggagatg ggcggtgttg tcgacaatgc tgcccgtgtg    1680
tatggtgtgc agggactgcg agtcatcgat ggttctattc cccctacgca aatgtcgtcc    1740
cattctatga cggtcttta tgccatggcc ttgaaggttg cggatgccat cttggcggat    1800
tatgcttcca tgcagtga                                                  1818

<210> SEQ ID NO 34
<211> LENGTH: 1818
<212> TYPE: DNA
<213> ORGANISM: Aspergillus niger

<400> SEQUENCE: 34
atgtctactc tccttgtgag ctcgcttgtg gtctccctcg ctgcggccct cccacactac      60
atcaggagca atggcatcga agccagcctc ctgactgacc caaggaggt tgccggccgc     120 actgtcgact acatcatcgc tggtggaggt ctgactggac tcaccactgc tgcccgtctg     180
acggagaacc ccgatatcac tgtgcttgtc atcgaaagtg gctcctacga gtctgacaga     240
ggtcctatca ttgaggacct gaacgcttac ggtgacattt ttggcagcag tgtggaccac     300
gcctacgaga ctgtcgagct cgccaccaac aatcagactg cgctgatccg ctccggaaat     360
ggtctcggtg gctctaccct cgtcaacggt ggcgcttgga ctcgccccca caaggcacaa     420
gttgactcat gggagaccgt cttcggaaat gagggctgga actgggacag cgtggccgcc     480
tactccctcc aggctgagcg tgctcgcgca ccaaatgcca acagattgc tgctggccac     540 tactttaatg catcctgcca tggtatcaat ggtactgtcc acgccggacc ccgcgatacc     600
ggtgatgact actcccccat cgtcaaggct ctcatgagcg ctgtcgaaga caggggcgtt     660
cccaccaaga aggacttggg atgcggtgac ccccatggtg tgtccatgtt ccccaacacc     720
ttgcacgaag accaagtgcg ctctgatgcc gctcgtgaat ggctcctccc caactaccag     780
cgtcccaacc tgcaagtcct cactggacgg tatgttggaa aggtcctgct cagccagaac     840
gctaccacac ctcgtgccgt tggcgtggaa ttcggcaccc acaagggcaa caccacaac     900 gtctacgcta agcacgaggt cctcctggcc gctggatccg ctgtctctcc caccatcctc     960
gaatattccg gtatcggaat gaagtccatt ctagagcctc ttggaattga caccgtcgtt    1020
gacctgcccg ttggtctcaa ccttcaggac cagaccacct ctaccgtccg ctcacgcatt    1080
acctccgccg gtgccggaca gggacaggcc gcttggttcg ctaccttcaa cgagaccttt    1140
ggcgactacg ccgaaaaggc tcacgagctg ctcaacacca agctggagca gtgggccgaa    1200
gaggccgtcg cccgtggcgg attccacaac accaccgctt tgctcatcca gtacgagaac    1260
```

```
taccgcgact ggatcgtcaa ggacaatgtc gcatactcgg aactcttcct cgacacggcc      1320
ggagtggcca gtttccatgt gtgggatctt ctgcccttca ctagaggata cgtacacatc      1380
ctcgacaagg acccctacct ccgccatttc gcatacgacc ctcagtactt tctcaacgag      1440
cttgacctgc tcggccaggc tgccgccact cagctggccc gcaacatctc caactccggt      1500
gccatgcaaa cttatttcgc tggagagact attcccggtg acaacctcgc gtatgatgcc      1560
gacttgagcg cctgggttga gtatatcccg tacaacttcc gccctaacta ccatggtgtg      1620
ggtacttgct ccatgatgcc gaaggagatg ggcggtgttg tcgacaatgc tgcccgtgtg      1680
tatggtgtgc agggactgcg agtcatcgat ggttctattc cccctacgca aatgtcgtcc      1740
cattctatga cggtctttta tgccatggcc ttgaaggttg cggatgccat cttggcggat      1800
tatgcttcca tgcagtga                                                    1818

<210> SEQ ID NO 35
<211> LENGTH: 1818
<212> TYPE: DNA
<213> ORGANISM: Aspergillus niger

<400> SEQUENCE: 35
atgtctactc tccttgtgag ctcgcttgtg gtctccctcg ctgcggccct cccacactac       60
atcaggagca atggcatcga agccagcctc ctgactgacc ccaaggaggt tgccggccgc      120
actgtcgact acatcatcgc tggtggaggt ctgactggac tcaccactgc tgcccgtctg      180
acggagaacc ccgatatcac tgtgcttgtc atcgaaagtg gctcctacga gtctgacaga      240
ggtcctatca ttgaggacct gaacgcttac ggtgacattt ttggcagcag tgtggaccac      300
gcctacgaga ctgtcgagct cgccaccaac aatcagactg cgctgatccg ctccggaaat      360
ggtctcggtg gctctaccct cgtcaacggt ggcacctgga ctcgccccca caaggcacaa      420
gttgactcat gggagaccgt cttcggaaat gagggctgga actgggacag cgtggccgcc      480 tactcccctcc aggctgagcg tgctcgcgca ccaaatgcca acagattgc tgctggccac      540 tactttaatg catcctgcca tggtatcaat ggtactgtcc acgccggacc ccgcgatacc      600
ggtgatgact actcccccat cgtcaaggct ctcatgagcg ctgtcgaaga cagggggcgtt      660 cccaccaaga aggacttggg atgcggtgac ccccatggtg tgtccatgtt ccccaacacc      720
ttgcacgaag accaagtgcg ctctgatgcc gctcgtgaat ggctcctccc caactaccag      780
cgtcccaacc tgcaagtcct cactggacgg tatgttggaa aggtcctgct cagccagaac      840
gctaccacac tcgtgccgt tggcgtggaa ttcggcaccc acaagggcaa cacccacaac      900
gtctacgcta agcacgaggt cctcctggcc gctggatccg ctgtctctcc caccatcctc      960
gaatattccg gtatcggaat gaagtccatt ctagagcctc ttggaattga caccgtcgtt     1020
gacctgcccg ttggtctcaa ccttcaggac caggctacct ctaccgtccg ctcacgcatt     1080
acctccgccg gtgccggaca gggacaggcc gcttggttcg ctaccttcaa cgagaccttt     1140
ggcgactacg ccgaaaaggc tcacgagctg ctcaacacca agctggagca gtgggccgaa     1200
gaggccgtcg cccgtggcgg attccacaac accaccgctt tgctcatcca gtacgagaac     1260
taccgcgact ggatcgtcaa ggacaatgtc gcatactcgg aactcttcct cgacacggcc     1320
ggagtggcca gtttccatgt gtgggatctt ctgcccttca ctagaggata cgtacacatc     1380
ctcgacaagg acccctacct ccgccatttc gcatacgacc ctcagtactt tctcaacgag     1440
cttgacctgc tcggccaggc tgccgccact cagctggccc gcaacatctc caactccggt     1500
gccatgcaaa cttatttcgc tggagagact attcccggtg acaacctcgc gtatgatgcc     1560
```

```
gacttgagcg cctgggttga gtatatcccg tacaacttcc gccctaacta ccatggtgtg    1620
ggtacttgct ccatgatgcc gaaggagatg ggcggtgttg tcgacaatgc tgcccgtgtg    1680
tatggtgtgc agggactgcg agtcatcgat ggttctattc cccctacgca aatgtcgtcc    1740
cattctatga cggtcttta tgccatggcc ttgaaggttg cggatgccat cttggcggat     1800
tatgcttcca tgcagtga                                                   1818
```

<210> SEQ ID NO 36
<211> LENGTH: 1818
<212> TYPE: DNA
<213> ORGANISM: Aspergillus niger

<400> SEQUENCE: 36

```
atgtctactc tccttgtgag ctcgcttgtg gtctccctcg ctgcggccct cccacactac      60
atcaggagca atggcatcga agccagcctc ctgactgacc ccaaggaggt tgccggccgc    120
actgtcgact acatcatcgc tggtggaggt ctgactggac tcaccactgc tgcccgtctg    180
acggagaacc ccgatatcac tgtgcttgtc atcgaaagtg gctcctacga gtctgacaga    240
ggtcctatca ttgaggacct gaacgcttac ggtgacattt ttggcagcag tgtgaccac     300 gcctacgaga ctgtcgagct cgccaccaac aatcagactg cgctgatccg ctccggaaat    360
ggtctcggtg ctctaccct cgtcaacggt ggcgcttgga ctcgccccca caaggcacaa     420
gttgactcat gggagaccgt cttcggaaat gagggctgga actgggacag cgtggccgcc    480 tactcctcc aggctgagcg tgctcgcgca ccaaatgcca acagattgc tgctggccac      540 tactttaatg catcctgcca tggtatcaat ggtactgtcc acgccggacc ccgcgatacc    600
ggtgatgact actcccccat cgtcaaggct ctcatgagcg ctgtcgaaga caggggcgtt    660
cccaccaaga aggacttggg atgcggtgac ccccatggtg tgtccatgtt ccccaacacc    720
ttgcacgaag accaagtgcg ctctgatgcc gctcgtgaat ggctcctccc caactaccag    780
cgtcccaacc tgcaagtcct cactggacgg tatgttggaa aggtcctgct cagccagaac    840
gctaccacac ctcgtgccgt tggcgtggaa ttcggcaccc acaagggcaa cacccacaac    900
gtctacgcta agcacgaggt cctcctggcc gctggatccg ctgtctctcc caccatcctc    960
gaatattccg gtatcggaat gaagtccatt ctagagcctc ttggaattga caccgtcgtt   1020
gacctgcccg ttggtctcaa ccttcaggac caggctacct ctaccgtccg ctcacgcatt   1080
acctccgccg gtgccggaca gggacaggcc gcttggttcg ctaccttcaa cgagaccttt   1140
ggcgactacg ccgaaaaggc tcacgagctg ctcaacacca gctggagca gtgggccgaa    1200 gaggccgtcg cccgtggcgg attccacaac accaccgctt tgctcatcca gtacgagaac   1260
taccgcgact ggatcgtcaa ggacaatgtc gcatactcgg aactcttcct cgacacggcc   1320
ggagtggcca gtttccatgt gtgggatctt ctgcccttca ctagaggata cgtacacatc   1380
ctcgacaagg accctacct ccgccatttc gcatacgacc tcagtacttt ctcaacgag    1440 cttgacctgc tcggccaggc tgccgccact cagctggccc gcaacatctc caactccggt   1500
gccatgcaaa cttatttcgc tggagagact attcccggtg acaacctcgc gtatgatgcc   1560
gacttgagcg cctgggttga gtatatcccg tacaacttcc gccctaacta ccatggtgtg   1620
ggtacttgct ccatgatgcc gaaggagatg ggcggtgttg tcgacaatgc tgcccgtgtg   1680
tatggtgtgc agggactgcg agtcatcgat ggttctattc cccctacgca aatgtcgtcc   1740
cattctatga cggtcttta tgccatggcc ttgaaggttg cggatgccat cttggcggat    1800
```
tatgcttcca tgcagtga                                         1818

<210> SEQ ID NO 37
<211> LENGTH: 1836
<212> TYPE: DNA
<213> ORGANISM: Aspergillus niger

<400> SEQUENCE: 37
aagcttaaaa aaatgtctac tctccttgtg agctcgcttg tggtctccct cgctgcggcc    60
ctcccacact acatcaggag caatggcatc gaagccagcc tcctgactga ccccaaggag   120
gttgccggcc gcactgtcga ctacatcatc gctggtggag gtctgactgg actcaccact   180
gctgcccgtc tgacggagaa ccccgatatc actgtgcttg tcatcgaaag tggctcctac   240
gagtctgaca gaggtcctat cattgaggac ctgaacgctt acggtgacat ttttggcagc   300
agtgtggacc acgcctacga gactgtcgag ctcgccacca caatcagac tgcgctgatc   360
cgctccggaa atggtctcgg tggctctacc ctcgtcaacg gtggcacctg gactcgcccc   420
cacaaggcac aagttgactc atgggagacc gtcttcggaa atgagggctg gaactgggac   480
agcgtggccg cctactccct ccaggctgag cgtgctcgcg caccaaatgc caaacagatt   540
gctgctggcc actactttaa tgcatcctgc catggtatca atggtactgt ccacgccgga   600
ccccgcgata ccggtgatga ctactccccc atcgtcaagg ctctcatgag cgctgtcgaa   660
gacaggggcg ttcccaccaa gaaggacttg ggatgcggtg accccatgg tgtgtccatg   720
ttccccaaca ccttgcacga agaccaagtg cgctctgatg ccgctcgtga atggctcctc   780
cccaactacc agcgtcccaa cctgcaagtc ctcactggac ggtatgttgg aaaggtcctg   840
ctcagccaga acgctaccac acctcgtgcc gttggcgtgg aattcggcac ccacaagggc   900
aacacccaca acgtctacgc taagcacgag gtcctcctgg ccgctggatc cgctgtctct   960
cccaccatcc tcgaatattc cggtatcgga atgaagtcca ttctagagcc tcttggaatt  1020
gacaccgtcg ttgacctgcc cgttggtctc aaccttcagg accagaccac ctctaccgtc  1080
cgctcacgca ttacctccgc cggtgccgga cagggacagg ccgcttggtt cgctaccttc  1140
aacgagacct ttggcgacta cgccgaaaag gctcacgagc tgctcaacac caagctggag  1200
cagtgggccg aagaggccgt cgcccgtggc ggattccaca acaccaccgc tttgctcatc  1260
cagtacgaga actaccgcga ctggatcgtc aaggacaatg tcgcatactc ggaactcttc  1320
ctcgacacgg ccggagtggc cagtttcgat gtgtgggatc ttctgccctt cactagagga  1380
tacgtacaca tcctcgacaa ggaccctac ctccgccatt tcgcatacga ccctcagtac  1440
tttctcaacg agcttgacct gctcggccag gctgccgcca ctcagctggc ccgcaacatc  1500
tccaactccg gtgccatgca aacttatttc gctggagaga ctattcccgg tgacaacctc  1560
gcgtatgatg ccgacttgag cgcctgggtt gagtatatcc cgtacaactt ccgccctaac  1620
taccatggtg tgggtacttg ctccatgatg ccgaaggaga tgggcggtgt tgtcgacaat  1680
gctgcccgtg tgtatggtgt gcagggactg cgagtcatcg atggttctat tccccctacg  1740
caaatgtcgt cccatgttat gacggtcttt tatgccatgg ccttgaaggt tgcggatgcc  1800
atcttggcgg attatgcttc catgcagtga ctcgag                            1836

<210> SEQ ID NO 38
<211> LENGTH: 1818
<212> TYPE: DNA
<213> ORGANISM: Aspergillus niger

<400> SEQUENCE: 38

-continued

```
atgcagactc tccttgtgag ctcgcttgtg gtctccctcg ctgcggccct cccacactac    60
atcaggagca atggcatcga agccagcctc ctgactgacc ccaaggaggt tgccggccgc   120
actgtcgact acatcatcgc tggtggaggt ctgactggac tcaccactgc tgcccgtctg   180
acggagaacc ccgatatcac tgtgcttgtc atcgaaagtg gctcctacga gtctgacaga   240
ggtcctatca ttgaggacct gaacgcttac ggtgacattt ttggcagcag tgtggaccac   300
gcctacgaga ctgtcgagct cgccaccaac aatcagactg cgctgatccg ctccggaaat   360
ggtctcggtg gctctaccct cgtcaacggt ggcacctgga ctcgccccca caaggcacaa   420
gttgactcat gggagaccgt cttcggaaat gagggctgga actgggacag cgtggccgcc   480
tactccctcc aggctgagcg tgctcgcgca ccaaatgcca aacagattgc tgctggccac   540
tactttaatg catcctgcca tggtatcaat ggtactgtcc acgccggacc ccgcgatacc   600
ggtgatgact actcccccat cgtcaaggct ctcatgagcg ctgtcgaaga cagggcgtt   660 cccaccaaga aggacttggg atgcggtgac ccccatggtg tgtccatgtt ccccaacacc   720
ttgcacgaag accaagtgcg ctctgatgcc gctcgtgaat ggctcctccc caactaccag   780
cgtcccaacc tgcaagtcct cactggacgg tatgttggaa aggtcctgct cagccagaac   840
gctaccacac ctcgtgccgt tggcgtggaa ttcggcaccc acaagggcaa cacccacaac   900
gtctacgcta agcacgaggt cctcctggcc gctggatccg ctgtctctcc caccatcctc   960
gaatattccg gtatcggaat gaagtccatt ctagagcctc ttggaattga caccgtcgtt  1020
gacctgcccg ttggtctcaa ccttcaggac cagaccacct ctaccgtccg ctcacgcatt  1080
acctccgccg gtgccggaca gggacaggcc gcttggttcg ctaccttcaa cgagaccttt  1140
ggcgactacg ccgaaaaggc tcacgagctg ctcaacacca agctggagca gtgggccgaa  1200
gaggccgtcg cccgtggcgg attccacaac accaccgctt tgctcatcca gtacgagaac  1260
taccgcgact ggatcgtcaa ggacaatgtc gcatactcgg aactcttcct cgacacggcc  1320
ggagtggcca gtttcgatgt gtgggatctt ctgcccttca ctagaggata cgtacacatc  1380
ctcgacaagg acccctacct ccgccatttc gcatacgacc ctcagtactt tctcaacgag  1440
cttgacctgc tcggccaggc tgccgccact cagctggccc gcaacatctc caactccggt  1500
gccatgcaaa cttatttcgc tggagagact attcccggtg acaacctcgc gtatgatgcc  1560
gacttgagcg cctgggttga gtatatcccg tacaacttcc gccctaacta ccatggtgtg  1620
ggtacttgct ccatgatgcc gaaggagatg ggcggtgttg tcgacaatgc tgcccgtgtg  1680
tatggtgtgc agggactgcg agtcatcgat ggttctattc cccctacgca aatgtcgtcc  1740
catgttatga cggtcttttta tgccatggcc ttgaaggttg cggatgccat cttggcggat  1800
tatgcttcca tgcagtga                                                1818
```

<210> SEQ ID NO 39
<211> LENGTH: 42
<212> TYPE: DNA
<213> ORGANISM: Artificial Sequence
<220> FEATURE:
<223> OTHER INFORMATION: primer for PCR
<400> SEQUENCE: 39

```
gatcagaagc ttaaaaaaat gtctactctc cttgtgagct cg                       42
```

<210> SEQ ID NO 40
<211> LENGTH: 33
<212> TYPE: DNA

```
<213> ORGANISM: Artificial Sequence
<220> FEATURE:
<223> OTHER INFORMATION: primer for PCR

<400> SEQUENCE: 40
gatcagctcg agtcactgca tggaagcata atc                                33

<210> SEQ ID NO 41
<211> LENGTH: 40
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (21)..(23)
<223> OTHER INFORMATION: n is a, c, g, or t

<400> SEQUENCE: 41
ccaccaacaa tcagactgcg nnnatccgct ccggaaatgg                         40

<210> SEQ ID NO 42
<211> LENGTH: 38
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (21)..(23)
<223> OTHER INFORMATION: n is a, c, g, or t

<400> SEQUENCE: 42
gctctaccct cgtcaacggt nnnacctgga ctcgcccc                           38

<210> SEQ ID NO 43
<211> LENGTH: 33
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (16)..(18)
<223> OTHER INFORMATION: n is a, c, g, or t

<400> SEQUENCE: 43
ctcgtcaacg gtggcnnntg gactcgcccc cac                                33

<210> SEQ ID NO 44
<211> LENGTH: 37
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (19)..(21)
<223> OTHER INFORMATION: n is a, c, g, or t

<400> SEQUENCE: 44
catggtatca atggtactnn ncacgccgga ccccgcg                            37

<210> SEQ ID NO 45
<211> LENGTH: 38
<212> TYPE: DNA
<213> ORGANISM: Artificial Sequence
<220> FEATURE:
<223> OTHER INFORMATION: primer for mutation
```

```
<220> FEATURE:
<221> NAME/KEY: misc_feature
<222> LOCATION: (20)..(22)
<223> OTHER INFORMATION: n is a, c, g, or t

<400> SEQUENCE: 45
caaccttcag gaccagaccn nntctaccgt ccgctcac                                   38

<210> SEQ ID NO 46
<211> LENGTH: 37
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (19)..(21)
<223> OTHER INFORMATION: n is a, c, g, or t

<400> SEQUENCE: 46
gtcgcatact cggaactcnn nctcgacacg gccggag                                    37

<210> SEQ ID NO 47
<211> LENGTH: 37
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (19)..(21)
<223> OTHER INFORMATION: n is a, c, g, or t

<400> SEQUENCE: 47
gccggagtgg ccagtttcnn ngtgtgggat cttctgc                                    37

<210> SEQ ID NO 48
<211> LENGTH: 43
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (20)..(22)
<223> OTHER INFORMATION: n is a, c, g, or t

<400> SEQUENCE: 48
catcctccgc catttcgcan nngaccctca gtactttctc aac                             43

<210> SEQ ID NO 49
<211> LENGTH: 40
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (21)..(23)
<223> OTHER INFORMATION: n is a, c, g, or t

<400> SEQUENCE: 49
cttatttcgc tggagagact nnncccggtg acaacctcgc                                 40

<210> SEQ ID NO 50
<211> LENGTH: 42
<212> TYPE: DNA
<213> ORGANISM: Artificial Sequence
<220> FEATURE:
```

```
<223> OTHER INFORMATION: primer for mutation
<220> FEATURE:
<221> NAME/KEY: misc_feature
<222> LOCATION: (17)..(19)
<223> OTHER INFORMATION: n is a, c, g, or t

<400> SEQUENCE: 50
cccgtacaac ttccgcnnna actaccatgg tgtgggtact tg                42

<210> SEQ ID NO 51
<211> LENGTH: 42
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (20)..(22)
<223> OTHER INFORMATION: n is a, c, g, or t

<400> SEQUENCE: 51
gtacaacttc cgccctaacn nncatggtgt gggtacttgc tc                42

<210> SEQ ID NO 52
<211> LENGTH: 45
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (21)..(23)
<223> OTHER INFORMATION: n is a, c, g, or t

<400> SEQUENCE: 52
ctacgcaaat gtcgtcccat nnnatgacgg tcttttatgc catgg             45

<210> SEQ ID NO 53
<211> LENGTH: 45
<212> TYPE: DNA
<213> ORGANISM: Artificial Sequence
<220> FEATURE:
<223> OTHER INFORMATION: primer for mutation
<220> FEATURE:
<221> NAME/KEY: misc_feature
<222> LOCATION: (24)..(26)
<223> OTHER INFORMATION: n is a, c, g, or t

<400> SEQUENCE: 53
ctacgcaaat gtcgtcccat gttnnnacgg tcttttatgc catgg             45

<210> SEQ ID NO 54
<211> LENGTH: 51
<212> TYPE: DNA
<213> ORGANISM: Artificial Sequence
<220> FEATURE:
<223> OTHER INFORMATION: primer for PCR

<400> SEQUENCE: 54
gatcagctcg agtcaatggt gatggtgatg atgctgcatg gaagcataat c       51

<210> SEQ ID NO 55
<211> LENGTH: 33
<212> TYPE: DNA
<213> ORGANISM: Artificial Sequence
<220> FEATURE:
<223> OTHER INFORMATION: primer for mutation

<400> SEQUENCE: 55
```

```
ctcgtcaacg gtggcgcttg gactcgcccc cac                                    33
```

<210> SEQ ID NO 56
<211> LENGTH: 35
<212> TYPE: DNA
<213> ORGANISM: Artificial Sequence
<220> FEATURE:
<223> OTHER INFORMATION: primer for mutation

<400> SEQUENCE: 56

```
ccttcaggac cagaccgctt ctaccgtccg ctcac                                  35
```

<210> SEQ ID NO 57
<211> LENGTH: 34
<212> TYPE: DNA
<213> ORGANISM: Artificial Sequence
<220> FEATURE:
<223> OTHER INFORMATION: primer for mutation

<400> SEQUENCE: 57

```
ggagtggcca gtttccatgt gtgggatctt ctgc                                   34
```

<210> SEQ ID NO 58
<211> LENGTH: 42
<212> TYPE: DNA
<213> ORGANISM: Artificial Sequence
<220> FEATURE:
<223> OTHER INFORMATION: primer for mutation

<400> SEQUENCE: 58

```
cgcaaatgtc gtcccattct atgacggtct tttatgccat gg                          42
```

<210> SEQ ID NO 59
<211> LENGTH: 605
<212> TYPE: PRT
<213> ORGANISM: Aspergillus niger

<400> SEQUENCE: 59

```
Met Ser Thr Leu Leu Val Ser Ser Leu Val Val Ser Leu Ala Ala Ala
1               5                   10                  15

Leu Pro His Tyr Ile Arg Ser Asn Gly Ile Glu Ala Ser Leu Leu Thr
            20                  25                  30

Asp Pro Lys Glu Val Ala Gly Arg Thr Val Asp Tyr Ile Ile Ala Gly
        35                  40                  45

Gly Gly Leu Thr Gly Leu Thr Thr Ala Ala Arg Leu Thr Glu Asn Pro
    50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
            100                 105                 110

Thr Ala Leu Ile Arg Ser Gly Asn Gly Leu Gly Gly Ser Thr Leu Val
        115                 120                 125

Asn Gly Gly Thr Trp Thr Arg Pro His Lys Ala Gln Val Asp Ser Trp
    130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175
```

```
Ala Ala Gly His Tyr Phe Asn Ala Ser Cys His Gly Ile Asn Gly Thr
            180                 185                 190

Val His Ala Gly Pro Arg Asp Thr Gly Asp Tyr Ser Pro Ile Val
        195                 200                 205

Lys Ala Leu Met Ser Ala Val Glu Asp Arg Gly Val Pro Thr Lys Lys
        210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
        290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ser Thr Val Arg Ser Arg Ile Thr Ser Ala Gly Ala Gly Gln Gly
        355                 360                 365

Gln Ala Ala Trp Phe Ala Thr Phe Asn Glu Thr Phe Gly Asp Tyr Ala
        370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe His Val Trp
        435                 440                 445

Asp Leu Leu Pro Phe Thr Arg Gly Tyr Val His Ile Leu Asp Lys Asp
        450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
            500                 505                 510

Gly Asp Asn Leu Ala Tyr Asp Ala Asp Leu Ser Ala Trp Val Glu Tyr
        515                 520                 525

Ile Pro Tyr Asn Phe Arg Pro Asn Tyr His Gly Val Gly Thr Cys Ser
        530                 535                 540

Met Met Pro Lys Glu Met Gly Gly Val Val Asp Asn Ala Ala Arg Val
545                 550                 555                 560

Tyr Gly Val Gln Gly Leu Arg Val Ile Asp Gly Ser Ile Pro Pro Thr
                565                 570                 575

Gln Met Ser Ser His Arg Met Thr Val Phe Tyr Ala Met Ala Leu Lys
            580                 585                 590
```

```
Val Ala Asp Ala Ile Leu Ala Asp Tyr Ala Ser Met Gln
            595                 600                 605

<210> SEQ ID NO 60
<211> LENGTH: 605
<212> TYPE: PRT
<213> ORGANISM: Aspergillus niger

<400> SEQUENCE: 60

Met Ser Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ile Ala Gly
            35                  40                  45

Gly Gly Leu Thr Gly Leu Thr Thr Ala Ala Arg Leu Thr Glu Asn Pro
50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
                100                 105                 110

Thr Ala Leu Ile Arg Ser Gly Asn Gly Leu Gly Gly Ser Thr Leu Val
            115                 120                 125

Asn Gly Gly Thr Trp Thr Arg Pro His Lys Ala Gln Val Asp Ser Trp
130                 135                 140

Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
            180                 185                 190

Val His Ala Gly Pro Arg Asp Thr Gly Asp Asp Tyr Ser Pro Ile Val
        195                 200                 205

Lys Ala Leu Met Ser Ala Val Glu Asp Arg Gly Val Pro Thr Lys Lys
210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
            260                 265                 270

Gly Lys Val Leu Leu Ser Gln Asn Ala Thr Thr Pro Arg Ala Val Gly
        275                 280                 285

Val Glu Phe Gly Thr His Lys Gly Asn Thr His Asn Val Tyr Ala Lys
    290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
            340                 345                 350

Thr Ser Thr Val Arg Ser Arg Ile Thr Ser Ala Gly Ala Gly Gln Gly
        355                 360                 365
```

```
Gln Ala Ala Trp Phe Ala Thr Phe Asn Glu Thr Phe Gly Asp Tyr Ala
        370                 375                 380

Glu Lys Ala His Glu Leu Leu Asn Thr Lys Leu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
            420                 425                 430

Ser Glu Leu Phe Leu Asp Thr Ala Gly Val Ala Ser Phe His Val Trp
        435                 440                 445

Asp Leu Leu Pro Phe Thr Arg Gly Tyr Val His Ile Leu Asp Lys Asp
450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Thr Gln Leu Ala Arg Asn Ile
            485                 490                 495

Ser Asn Ser Gly Ala Met Gln Thr Tyr Phe Ala Gly Glu Thr Ile Pro
                500                 505                 510

Gly Asp Asn Leu Ala Tyr Asp Ala Asp Leu Ser Ala Trp Val Glu Tyr
            515                 520                 525

Ile Pro Tyr Asn Phe Arg Pro Asn Tyr His Gly Val Gly Thr Cys Ser
530                 535                 540

Met Met Pro Lys Glu Met Gly Val Val Asp Asn Ala Ala Arg Val
545                 550                 555                 560

Tyr Gly Val Gln Gly Leu Arg Val Ile Asp Gly Ser Ile Pro Pro Thr
            565                 570                 575

Gln Met Ser Ser His Leu Met Thr Val Phe Tyr Ala Met Ala Leu Lys
        580                 585                 590

Val Ala Asp Ala Ile Leu Ala Asp Tyr Ala Ser Met Gln
        595                 600                 605

<210> SEQ ID NO 61
<211> LENGTH: 605
<212> TYPE: PRT
<213> ORGANISM: Aspergillus niger

<400> SEQUENCE: 61

Met Ser Thr Leu Leu Val Ser Ser Leu Val Ser Leu Ala Ala Ala
1               5                   10                  15

Leu Pro His Tyr Ile Arg Ser Asn Gly Ile Glu Ala Ser Leu Leu Thr
                20                  25                  30

Asp Pro Lys Glu Val Ala Gly Arg Thr Val Asp Tyr Ile Ile Ala Gly
            35                  40                  45

Gly Gly Leu Thr Gly Leu Thr Thr Ala Ala Arg Leu Thr Glu Asn Pro
50                  55                  60

Asp Ile Thr Val Leu Val Ile Glu Ser Gly Ser Tyr Glu Ser Asp Arg
65                  70                  75                  80

Gly Pro Ile Ile Glu Asp Leu Asn Ala Tyr Gly Asp Ile Phe Gly Ser
                85                  90                  95

Ser Val Asp His Ala Tyr Glu Thr Val Glu Leu Ala Thr Asn Asn Gln
                100                 105                 110

Thr Ala Leu Ile Arg Ser Gly Asn Gly Leu Gly Gly Ser Thr Leu Val
            115                 120                 125

Asn Gly Gly Thr Trp Thr Arg Pro His Lys Ala Gln Val Asp Ser Trp
```

```
                130             135             140
Glu Thr Val Phe Gly Asn Glu Gly Trp Asn Trp Asp Ser Val Ala Ala
145                 150                 155                 160

Tyr Ser Leu Gln Ala Glu Arg Ala Arg Ala Pro Asn Ala Lys Gln Ile
                165                 170                 175

Ala Ala Gly His Tyr Phe Asn Ala Ser Cys His Gly Ile Asn Gly Thr
                180                 185                 190

Val His Ala Gly Pro Arg Asp Thr Gly Asp Tyr Ser Pro Ile Val
                195                 200                 205

Lys Ala Leu Met Ser Ala Val Glu Asp Arg Gly Val Pro Thr Lys Lys
                210                 215                 220

Asp Leu Gly Cys Gly Asp Pro His Gly Val Ser Met Phe Pro Asn Thr
225                 230                 235                 240

Leu His Glu Asp Gln Val Arg Ser Asp Ala Ala Arg Glu Trp Leu Leu
                245                 250                 255

Pro Asn Tyr Gln Arg Pro Asn Leu Gln Val Leu Thr Gly Arg Tyr Val
                260                 265                 270

Gly Lys Val Leu Leu Ser Gln Asn Ala Thr Thr Pro Arg Ala Val Gly
                275                 280                 285

Val Glu Phe Gly Thr His Lys Gly Asn Thr His Asn Val Tyr Ala Lys
290                 295                 300

His Glu Val Leu Leu Ala Ala Gly Ser Ala Val Ser Pro Thr Ile Leu
305                 310                 315                 320

Glu Tyr Ser Gly Ile Gly Met Lys Ser Ile Leu Glu Pro Leu Gly Ile
                325                 330                 335

Asp Thr Val Val Asp Leu Pro Val Gly Leu Asn Leu Gln Asp Gln Thr
                340                 345                 350

Thr Ser Thr Val Arg Ser Arg Ile Thr Ser Ala Gly Ala Gly Gln Gly
                355                 360                 365

Gln Ala Ala Trp Phe Ala Thr Phe Asn Glu Thr Phe Gly Asp Tyr Ala
                370                 375                 380

Glu Lys Ala His Glu Leu Leu Asn Thr Lys Leu Glu Gln Trp Ala Glu
385                 390                 395                 400

Glu Ala Val Ala Arg Gly Gly Phe His Asn Thr Thr Ala Leu Leu Ile
                405                 410                 415

Gln Tyr Glu Asn Tyr Arg Asp Trp Ile Val Lys Asp Asn Val Ala Tyr
                420                 425                 430

Ser Glu Leu Phe Leu Asp Thr Ala Gly Val Ala Ser Phe His Val Trp
                435                 440                 445

Asp Leu Leu Pro Phe Thr Arg Gly Tyr Val His Ile Leu Asp Lys Asp
450                 455                 460

Pro Tyr Leu Arg His Phe Ala Tyr Asp Pro Gln Tyr Phe Leu Asn Glu
465                 470                 475                 480

Leu Asp Leu Leu Gly Gln Ala Ala Ala Thr Gln Leu Ala Arg Asn Ile
                485                 490                 495

Ser Asn Ser Gly Ala Met Gln Thr Tyr Phe Ala Gly Glu Thr Ile Pro
                500                 505                 510

Gly Asp Asn Leu Ala Tyr Asp Ala Asp Leu Ser Ala Trp Val Glu Tyr
                515                 520                 525

Ile Pro Tyr Asn Phe Arg Pro Asn Tyr His Gly Val Gly Thr Cys Ser
                530                 535                 540

Met Met Pro Lys Glu Met Gly Gly Val Val Asp Asn Ala Ala Arg Val
545                 550                 555                 560
```

Tyr Gly Val Gln Gly Leu Arg Val Ile Asp Gly Ser Ile Pro Pro Thr
            565                 570                 575

Gln Met Ser Ser His Pro Met Thr Val Phe Tyr Ala Met Ala Leu Lys
            580                 585                 590

Val Ala Asp Ala Ile Leu Ala Asp Tyr Ala Ser Met Gln
            595                 600             605

<210> SEQ ID NO 62
<211> LENGTH: 1818
<212> TYPE: DNA
<213> ORGANISM: Aspergillus niger

<400> SEQUENCE: 62

| | | | | | |
|---|---|---|---|---|---|
| atgtctactc | tccttgtgag | ctcgcttgtg | gtctccctcg | ctgcggccct | cccacactac | 60 |
| atcaggagca | atggcatcga | agccagcctc | ctgactgacc | ccaaggaggt | tgccggccgc | 120 |
| actgtcgact | acatcatcgc | tggtggaggt | ctgactggac | tcaccactgc | tgcccgtctg | 180 |
| acggagaacc | ccgatatcac | tgtgcttgtc | atcgaaagtg | ctcctacga | gtctgacaga | 240 |
| ggtcctatca | ttgaggacct | gaacgcttac | ggtgacattt | ttggcagcag | tgtggaccac | 300 |
| gcctacgaga | ctgtcgagct | cgccaccaac | aatcagactg | cgctgatccg | ctccggaaat | 360 |
| ggtctcggtg | ctctaccct | cgtcaacggt | ggcacctgga | ctcgccccca | caaggcacaa | 420 |
| gttgactcat | gggagaccgt | cttcggaaat | gagggctgga | actgggacag | cgtggccgcc | 480 |
| tactccctcc | aggctgagcg | tgctcgcgca | ccaaatgcca | aacagattgc | tgctggccac | 540 |
| tactttaatg | catcctgcca | tggtatcaat | ggtactgtcc | acgccggacc | ccgcgatacc | 600 |
| ggtgatgact | actccccat | cgtcaaggct | ctcatgagcg | ctgtcgaaga | cagggcgtt | 660 |
| cccaccaaga | aggacttggg | atgcggtgac | ccccatggtg | tgtccatgtt | ccccaacacc | 720 |
| ttgcacgaag | accaagtgcg | ctctgatgcc | gctcgtgaat | ggctcctccc | caactaccag | 780 |
| cgtcccaacc | tgcaagtcct | cactggacgg | tatgttggaa | aggtcctgct | cagccagaac | 840 |
| gctaccacac | tcgtgccgt | tggcgtggaa | ttcggcaccc | acaagggcaa | cacccacaac | 900 |
| gtctacgcta | agcacgaggt | cctcctggcc | gctggatccg | ctgtctctcc | caccatcctc | 960 |
| gaatattccg | gtatcggaat | gaagtccatt | ctagagcctc | ttggaattga | caccgtcgtt | 1020 |
| gacctgcccg | ttggtctcaa | ccttcaggac | cagaccacct | ctaccgtccg | ctcacgcatt | 1080 |
| acctccgccg | gtgccggaca | gggacaggcc | gcttggttcg | ctaccttcaa | cgagaccttt | 1140 |
| ggcgactacg | ccgaaaaggc | tcacgagctg | ctcaacacca | agctggagca | gtgggccgaa | 1200 |
| gaggccgtcg | cccgtggcgg | attccacaac | accaccgctt | tgctcatcca | gtacgagaac | 1260 |
| taccgcgact | ggatcgtcaa | ggacaatgtc | gcatactcgg | aactcttcct | cgacacggcc | 1320 |
| ggagtggcca | gtttccatgt | gtgggatctt | ctgcccttca | ctagaggata | cgtacacatc | 1380 |
| ctcgacaagg | accctacct | ccgccatttc | gcatacgacc | tcagtactt | tctcaacgag | 1440 |
| cttgacctgc | tcggccaggc | tgccgccact | cagctggccc | gcaacatctc | caactccggt | 1500 |
| gccatgcaaa | cttatttcgc | tggagagact | attcccggtg | acaacctcgc | gtatgatgcc | 1560 |
| gacttgagcg | cctgggttga | gtatatcccg | tacaacttcc | gccctaacta | ccatggtgtg | 1620 |
| ggtacttgct | ccatgatgcc | gaaggagatg | ggcggtgttg | tcgacaatgc | tgcccgtgtg | 1680 |
| tatggtgtgc | agggactgcg | agtcatcgat | ggttctattc | ccctacgca | aatgtcgtcc | 1740 |
| cataggatga | cggtctttta | tgccatggcc | ttgaaggttg | cggatgccat | cttggcggat | 1800 |
| tatgcttcca | tgcagtga | | | | | 1818 |

<210> SEQ ID NO 63
<211> LENGTH: 1818
<212> TYPE: DNA
<213> ORGANISM: Aspergillus niger

<400> SEQUENCE: 63

| | | | | | |
|---|---|---|---|---|---|
| atgtctactc | tccttgtgag | ctcgcttgtg | gtctccctcg | ctgcggccct | cccacactac | 60 |
| atcaggagca | atggcatcga | agccagcctc | ctgactgacc | ccaaggaggt | tgccggccgc | 120 |
| actgtcgact | acatcatcgc | tggtggaggt | ctgactggac | tcaccactgc | tgcccgtctg | 180 |
| acggagaacc | ccgatatcac | tgtgcttgtc | atcgaaagtg | gctcctacga | gtctgacaga | 240 |
| ggtcctatca | ttgaggacct | gaacgcttac | ggtgacattt | ttggcagcag | tgtggaccac | 300 |
| gcctacgaga | ctgtcgagct | cgccaccaac | aatcagactg | cgctgatccg | ctccggaaat | 360 |
| ggtctcggtg | gctctaccct | cgtcaacggt | ggcacctgga | ctcgccccca | caaggcacaa | 420 |
| gttgactcat | gggagaccgt | cttcggaaat | gagggctgga | actgggacag | cgtggccgcc | 480 |
| tactccctcc | aggctgagcg | tgctcgcgca | ccaaatgcca | aacagattgc | tgctggccac | 540 |
| tactttaatg | catcctgcca | tggtatcaat | ggtactgtcc | acgccggacc | ccgcgatacc | 600 |
| ggtgatgact | actcccccat | cgtcaaggct | ctcatgagcg | ctgtcgaaga | cagggggcgtt | 660 |
| cccaccaaga | aggacttggg | atgcggtgac | ccccatggtg | tgtccatgtt | ccccaacacc | 720 |
| ttgcacgaag | accaagtgcg | ctctgatgcc | gctcgtgaat | ggctcctccc | caactaccag | 780 |
| cgtcccaacc | tgcaagtcct | cactggacgg | tatgttggaa | aggtcctgct | cagccagaac | 840 |
| gctaccacac | tcgtgccgt | tggcgtggaa | ttcggcaccc | acaagggcaa | cacccacaac | 900 |
| gtctacgcta | agcacgaggt | cctcctggcc | gctggatccg | ctgtctctcc | caccatcctc | 960 |
| gaatattccg | gtatcggaat | gaagtccatt | ctagagcctc | ttggaattga | caccgtcgtt | 1020 |
| gacctgcccg | ttggtctcaa | ccttcaggac | cagaccacct | ctaccgtccg | ctcacgcatt | 1080 |
| acctccgccg | gtgccggaca | gggacaggcc | gcttggttcg | ctaccttcaa | cgagaccttt | 1140 |
| ggcgactacg | ccgaaaaggc | tcacgagctg | tcaacacca | agctggagca | gtgggccgaa | 1200 |
| gaggccgtcg | cccgtggcgg | attccacaac | accaccgctt | tgctcatcca | gtacgagaac | 1260 |
| taccgcgact | ggatcgtcaa | ggacaatgtc | gcatactcgg | aactcttcct | cgacacggcc | 1320 |
| ggagtggcca | gtttccatgt | gtgggatctt | ctgcccttca | ctagaggata | cgtacacatc | 1380 |
| ctcgacaagg | accctacct | ccgccatttc | gcatacgacc | ctcagtactt | tctcaacgag | 1440 |
| cttgacctgc | tcggccaggc | tgccgccact | cagctggccc | gcaacatctc | caactccggt | 1500 |
| gccatgcaaa | cttatttcgc | tggagagact | attcccggtg | acaacctcgc | gtatgatgcc | 1560 |
| gacttgagcg | cctgggttga | gtatatcccg | tacaacttcc | gccctaacta | ccatggtgtg | 1620 |
| ggtacttgct | ccatgatgcc | gaaggagatg | ggcggtgttg | tcgacaatgc | tgcccgtgtg | 1680 |
| tatggtgtgc | agggactgcg | agtcatcgat | ggttctattc | cccctacgca | aatgtcgtcc | 1740 |
| catttgatga | cggtcttttta | tgccatggcc | ttgaaggttg | cggatgccat | cttggcggat | 1800 |
| tatgcttcca | tgcagtga | | | | | 1818 |

<210> SEQ ID NO 64
<211> LENGTH: 1818
<212> TYPE: DNA
<213> ORGANISM: Aspergillus niger

<400> SEQUENCE: 64

-continued

```
atgtctactc tccttgtgag ctcgcttgtg gtctccctcg ctgcggccct cccacactac      60
atcaggagca atggcatcga agccagcctc ctgactgacc ccaaggaggt tgccggccgc     120
actgtcgact acatcatcgc tggtggaggt ctgactggac tcaccactgc tgcccgtctg     180
acggagaacc ccgatatcac tgtgcttgtc atcgaaagtg gctcctacga gtctgacaga     240
ggtcctatca ttgaggacct gaacgcttac ggtgacattt ttggcagcag tgtggaccac     300
gcctacgaga ctgtcgagct cgccaccaac aatcagactg cgctgatccg ctccggaaat     360
ggtctcggtg gctctaccct cgtcaacggt ggcacctgga ctcgccccca caaggcacaa     420
gttgactcat gggagaccgt cttcggaaat gagggctgga actgggacag cgtggccgcc     480
tactccctcc aggctgagcg tgctcgcgca ccaaatgcca aacagattgc tgctggccac     540
tactttaatg catcctgcca tggtatcaat ggtactgtcc acgccggacc ccgcgatacc     600
ggtgatgact actcccccat cgtcaaggct ctcatgagcg ctgtcgaaga caggggcgtt     660
cccaccaaga aggacttggg atgcggtgac ccccatggtg tgtccatgtt ccccaacacc     720
ttgcacgaag accaagtgcg ctctgatgcc gctcgtgaat ggctcctccc caactaccag     780
cgtcccaacc tgcaagtcct cactggacgg tatgttggaa aggtcctgct cagccagaac     840
gctaccacac ctcgtgccgt tggcgtggaa ttcggcaccc acaagggcaa cacccacaac     900
gtctacgcta agcacgaggt cctcctggcc gctggatccg ctgtctctcc caccatcctc     960
gaatattccg gtatcggaat gaagtccatt ctagagcctc ttggaattga caccgtcgtt    1020
gacctgcccg ttggtctcaa ccttcaggac cagaccacct ctaccgtccg ctcacgcatt    1080
acctccgccg gtgccggaca gggacaggcc gcttggttcg ctaccttcaa cgagacccttt  1140
ggcgactacg ccgaaaaggc tcacgagctg ctcaacacca agctggagca gtgggccgaa    1200
gaggccgtcg cccgtggcgg attccacaac accaccgctt tgctcatcca gtacgagaac    1260
taccgcgact ggatcgtcaa ggacaatgtc gcatactcgg aactcttcct cgacacggcc    1320
ggagtggcca gtttccatgt gtgggatctt ctgcccttca ctagaggata cgtacacatc    1380
ctcgacaagg acccctacct ccgccatttc gcatacgacc ctcagtactt tctcaacgag    1440
cttgacctgc tcggccaggc tgccgccact cagctggccc gcaacatctc caactccggt    1500
gccatgcaaa cttatttcgc tggagagact attcccggtg acaacctcgc gtatgatgcc    1560
gacttgagcg cctgggttga gtatatcccg tacaacttcc gccctaacta ccatggtgtg    1620
ggtacttgct ccatgatgcc gaaggagatg ggcggtgttg tcgacaatgc tgcccgtgtg    1680
tatggtgtgc agggactgcg agtcatcgat ggttctattc cccctacgca aatgtcgtcc    1740
catcctatga cggtcttttta tgccatggcc ttgaaggttg cggatgccat cttggcggat   1800
tatgcttcca tgcagtga                                                 1818
```

MUTANT ENZYME AND APPLICATION THEREOF

TECHNICAL FIELD

The present invention relates to a mutated enzyme and an enzyme modification method, and provides a glucose oxidase modified to resemble a dehydrogenase and a preparation method thereof. The present application claims priority to the Japanese Patent Application No. 2009-277096 filed on Dec. 5, 2009, and the content of the patent application is incorporated herein by reference in its entirety.

BACKGROUND ART

A Self-Monitering of Blood Glucose using an electrochemical biosensor has been widely used. The biosensor utilizes enzymes whose substrate is glucose, such as glucose dehydrogenase (hereinafter abbreviated as "GDH") and glucose oxidase (hereinafter abbreviated as "GO"). GO is highly specific to glucose and is excellent in thermostability. However, a measurement method of using GO is easily affected by dissolved oxygen in a measurement sample, and such a problem that the dissolved oxygen gives an adverse effect on a measurement result has been pointed out.

On the other hand, as an enzyme that does not receive an effect of dissolved oxygen and acts on glucose in absence of NAD (P), GDH having pyrroloquinoline quinone (PQQ) as a coenzyme (hereinafter abbreviated as "PQQ-GDH") has been known (for example, see Patent Documents 1 to 3). However, PQQ-GDH has problems such that (1) PQQ is easily dissociated from an enzyme, (2) specificity of glucose is low, and (3) since it is generally present in a membrane fraction, extraction and isolation operations thereof are performed with difficulty.

As an enzyme that does not receive an effect of dissolved oxygen and acts on glucose in absence of NAD (P), other than PQQ-GDH, a glucose dehydrogenase having a flavin adenine dinucleotide as a coenzyme (hereinafter abbreviated as "FAD-GDH") has been known. FAD-GDH has been obtained respectively from *Aspergillus oryzae* (Non-patent Documents 1 to 4, Patent Document 4) and *Aspergillus terreus* (Patent Document 5) so far. It has been known that, as general characteristics of FAD-GDH, reactivity to xylose is comparatively high (for example, in the case of FAD-GDH disclosed in Patent Document 5, reactivity to xylose is about 10% of action property to glucose) and an optimum temperature is high (for example, the optimum temperature of FAD-GDH disclosed in Patent Document 4 is about 60° C.). Note that enzyme modification has been vigorously tried for the purpose of enhancing practicality, and the like. Documents that report modification of FAD-GDH are shown below (Patent Documents 6 to 9).

Recently, a conformational analysis of FAD-GDH was carried out using the structure of GO, and it was reported that Glu414 and Arg502 are important for substrate recognition (Non-patent Documents 5 and 6).

PRIOR ART DOCUMENTS

Patent Documents

Patent Document 1: JP 2000-350588 A
Patent Document 2: JP 2001-197888 A
Patent Document 3: JP 2001-346587 A
Patent Document 4: WO No. 2007/139013
Patent Document 5: WO No. 2004/058958
Patent Document 6: JP 2009-225801 A
Patent Document 7: JP 2009-225800 A
Patent Document 8: JP 2009-159964 A
Patent Document 9: JP 2008-237210 A Non-Patent Documents Non-patent Document 1: Studies on the glucose dehydrogenase of *Aspergillus oryzae*. I. Induction of its synthesis by p-benzoquinone and hydroquinone, T. C. Bak, and R. Sato, Biochim. Biophys. Acta, 139, 265-276 (1967).
Non-patent Document 2: Studies on the glucose dehydrogenase of *Aspergillus oryzae*. II. Purification and physical and chemical properties, T. C. Bak, Biochim. Biophys. Acta, 139, 277-293 (1967).
Non-patent Document 3: Studies on the glucose dehydrogenase of *Aspergillus oryzae*. III. General enzymatic characteristics, T. C. Bak, Biochim. Biophys. Acta, 146, 317-327 (1967).
Non-patent Document 4: Studies on the glucose dehydrogenase of *Aspergillus oryzae*. IV. Histidyl residue as an active site, T. C. Bak, and R. Sato, Biochim. Biophys. Acta, 146, 328-335 (1967).
Non-patent Document 5: The Summaries of the Annual Meeting, 2009, The Pharmaceutical Society of Japan, Vol: 129, No: 3, Page: 118, Subject No: 26Q-pm115
Non-patent Document 6: The Summaries of the Annual Meeting, 2009, The Japanese Biochemical Society, Subject No: 3T5a-5 (3P-109)

SUMMARY OF THE INVENTION

Problems to be Solved by the Invention

FAD-GDH has advantages as compared to PQQ-GDH. On the other hand, FAD-GDH has comparatively high reactivity to xylose and thus holds a problem such that an accurate measurement of blood sugar levels undergoing xylose absorption test is hardly. In addition, since an optimum temperature is high, sufficient activity cannot be exhibited in the case of measuring at a low temperature such as a cold region. In such a measurement condition, temperature correction is necessary and an error of the measurement easily occurs. As described above, existing FAD-GDH has problems to be improved, and further improvement of practicality is expected. One object of the present invention is to respond to such a demand. Another object of the present invention is to provide a novel method for enzyme modification.

Means for Solving Problem

Approaches for obtaining high practical GDH are divided into two main methods such as (1) a method of modifying existing GDH (FAD-GDH and PQQ-GDH) and (2) a method of screening microorganisms, and the like. Numerous trials of these approaches have been already made (for example, Patent Documents 6 and 7 mentioned above), and a possibility that leads to creation of a more effective enzyme is low in the future. In view of the circumstance, the present inventors focused on the point that a glucose oxidase (GO) does not have the above described problem that FAD-GDH has. GO and FAD-GDH have been known for having comparatively high homology of the amino acid sequences. Focusing on the homology, the present inventors determined to employ a new approach of conferring GDH activity to GO, that is, making GO resemble GDH. Firstly, *Aspergillus niger*-derived GO was selected and its amino acid sequence was multiplyaligned with amino acid sequences of known FAD-GDHs. Then, amino acids which are conserved among the FAD-GDHs (high commonality) but different between the GO and the FAD-GDHs were searched in amino acids around the active center of the GO by using the alignment result and conformational data of the GO. As a result, 13 amino acid sites were identified. Then, when the mutated enzymes obtained by introducing mutation into these amino acid sites were prepared and characteristics thereof were examined, mutated enzymes having an increased ratio of GDH activity and GO activity (GDH activity/GO activity) were found. Thus, the sequences of the mutated enzymes were analyzed. As a result, the present inventors succeeded to identify 4 amino acid sites which are effective to increase of GDH activity, that is, effective to make GO resemble GDH. This result, on the other hand, suggests that amino acid sites except for the 4 sites among the initially identified 13 sites are not effective to increase of GDH activity. However, since the 13 sites are unmistakably amino acid sites found from detailed comparison between GO and FAD-GDHs, the remaining 9 sites also contain possibilities to be useful for modification and improvement of other characteristics such as substrate characteristics, coenzyme specificity, and temperature stability. In addition, a combination use of two or more sites has a possibility to improve a GDH activity and other characteristics. Thus, the remaining 9 amino acid sites have values and applications thereof are expected.

On the other hand, as a result of further studies, combinations of mutation sites, which are particularly effective to glucose dehydrogenation, were successfully identified. When the combination is employed, substrate specificity was also preferable (reactivity to xylose is low). In addition, as a result of trying optimization of mutation for the most excellent combination (that is, identification of the most effective amino acid after substitution), an amino acid after substitution, which is effective to glucose dehydrogenation, is identified, and at the same time, an amino acid after mutation, which becomes gives complete resemblance to glucose dehydrogenase completely, was found. Note that excellent substrate specificity (low reactivity to xylose) was also observed in a mutant.

By the way, it has been experienced in many cases that combination of two effective amino acid mutations gives a high possibility of generating an additive or synergistic effect. Therefore, 4 sites of positions to be mutated, which have been successfully identified, are not limited to a single use, but a combination thereof is also effective to make GO resemble GDH.

In addition, similarity in structures (primary structures, conformations) is high in enzymes in the same kind, and in view of the technical common knowledge of having high probability of generating a similar effect from a similar mutation, the mutation technique found by the present inventors can be applied also to *Penicillium amagasakiense*-derived GO, and other GOs, which have actually very high similarity in the structures to *Aspergillus niger*-derived GO shown in examples described later.

As described above, the present inventors succeeded in making GO resemble GDH and created mutant-type GO having high GDH activity. In addition, they also succeeded in identifying amino acid sites effective to mutation of GO. Some of the obtained mutants of GO did not show reactivity to xylose. That is, they succeeded in obtaining GDH that exceeds existing FAD-GDH from the viewpoint that reactivity to xylose is not shown.

The above described achievements, on the other hand, support the fact that an approach of utilizing a conformation around the active site as well as comprehensively comparing amino acid sequences in two kinds of enzymes with high similarity in the structures is an effective tool to modify an enzyme (particularly, conferring characteristics that the other enzyme has or characteristics that the other enzyme has in a more preferable condition to an enzyme to be modified).

The present inventions shown below are based on the above described achievements.

[1] A mutated enzyme, containing an amino acid sequence wherein one or at least two amino acids selected from the group consisting of (1) to (13) are substituted with another amino acid in an amino acid sequence of a microorganism-derived glucose oxidase:

(1) the amino acid corresponding to the amino acid at position 115 of the amino acid sequence of SEQ ID NO: 1;
(2) the amino acid corresponding to the amino acid at position 131 of the amino acid sequence of SEQ ID NO: 1;
(3) the amino acid corresponding to the amino acid at position 132 of the amino acid sequence of SEQ ID NO: 1;
(4) the amino acid corresponding to the amino acid at position 193 of the amino acid sequence of SEQ ID NO: 1;
(5) the amino acid corresponding to the amino acid at position 353 of the amino acid sequence of SEQ ID NO: 1;
(6) the amino acid corresponding to the amino acid at position 436 of the amino acid sequence of SEQ ID NO: 1;
(7) the amino acid corresponding to the amino acid at position 446 of the amino acid sequence of SEQ ID NO: 1;
(8) the amino acid corresponding to the amino acid at position 472 of the amino acid sequence of SEQ ID NO: 1;
(9) the amino acid corresponding to the amino acid at position 511 of the amino acid sequence of SEQ ID NO: 1;
(10) the amino acid corresponding to the amino acid at position 535 of the amino acid sequence of SEQ ID NO: 1;
(11) the amino acid corresponding to the amino acid at position 537 of the amino acid sequence of SEQ ID NO: 1;
(12) the amino acid corresponding to the amino acid at position 582 of the amino acid sequence of SEQ ID NO: 1; and
(13) the amino acid corresponding to the amino acid at position 583 of the amino acid sequence of SEQ ID NO: 1.

[2] The mutated enzyme according to [1], wherein the amino acid sequence of a microorganism-derived glucose oxidase is the amino acid sequence of SEQ ID NO: 1 or 2.

[3] The mutated enzyme according to [1] or [2], wherein the substituted amino acid is the amino acid (3), the amino acid (5), the amino acid (7) or the amino acid (12), or a combination of at least two amino acids selected from these amino acids.

[4] The mutated enzyme according to [3], wherein the amino acid after substitution is: alanine for the amino acid (3); alanine for the amino acid (5); histidine for the amino acid (7); and serine, arginine, leucine or proline for the amino acid (12).

[5] The mutated enzyme according to [1] or [2], wherein the substituted amino acid is the amino acid (3), the amino acid (7) or the amino acid (12), or a combination of at least two amino acids selected from these amino acids.

[6] The mutated enzyme according to [5], wherein the amino acid after substitution is: alanine for the amino acid (3); histidine for the amino acid (7); and serine, arginine, leucine or proline for the amino acid (12).

[7] The mutated enzyme according to [1] or [2], wherein the substituted amino acids are the amino acid (7) and the amino acid (12).

[8] The mutated enzyme according to [7], wherein the amino acid after substitution is: histidine for the amino acid (7); and serine, arginine, leucine or proline for the amino acid (12).

[9] The mutated enzyme according to [1], containing any one of the amino acid sequences of SEQ ID NOs: 7 to 21 and 59 to 61.

[10] A gene coding for the mutated enzyme according to any one of [1] to [9].

[11] The gene according to [10], containing any one of the nucleotide sequences of SEQ ID NOs: 22 to 36 and 62 to 64.

[12] A recombinant DNA, containing the gene according to [10] or [11].

[13] A microorganism having the recombinant DNA according to [12].

[14] A glucose measurement method, wherein glucose in a sample is measured using the mutated enzyme according to any one of [1] to [9].

[15] A glucose measuring reagent, containing the mutated enzyme according to any one of [1] to [9].

[16] A glucose measuring kit, containing the glucose measuring reagent according to [15].

[17] A method, wherein a glucose amount in an industrial product or a raw material thereof is reduced by using the mutated enzyme according to any one of [1] to [9].

[18] An enzyme preparation, containing the mutated enzyme according to any one of [1] to [9].

[19] A method of designing a mutated enzyme, including the following steps (i) and (ii):

(i) a step of specifying one or at least two amino acids selected from the group consisting of (1) to (13) in an amino acid sequence of an enzyme to be mutated that is a microorganism-derived glucose oxidase or a microorganism-derived flavin adenine dinucleotide-dependent glucose dehydrogenase:

(1) the amino acid corresponding to the amino acid at position 115 of the amino acid sequence of SEQ ID NO: 1;

(2) the amino acid corresponding to the amino acid at position 131 of the amino acid sequence of SEQ ID NO: 1;

(3) the amino acid corresponding to the amino acid at position 132 of the amino acid sequence of SEQ ID NO: 1;

(4) the amino acid corresponding to the amino acid at position 193 of the amino acid sequence of SEQ ID NO: 1;

(5) the amino acid corresponding to the amino acid at position 353 of the amino acid sequence of SEQ ID NO: 1;

(6) the amino acid corresponding to the amino acid at position 436 of the amino acid sequence of SEQ ID NO: 1;

(7) the amino acid corresponding to the amino acid at position 446 of the amino acid sequence of SEQ ID NO: 1;

(8) the amino acid corresponding to the amino acid at position 472 of the amino acid sequence of SEQ ID NO: 1;

(9) the amino acid corresponding to the amino acid at position 511 of the amino acid sequence of SEQ ID NO: 1;

(10) the amino acid corresponding to the amino acid at position 535 of the amino acid sequence of SEQ ID NO: 1;

(11) the amino acid corresponding to the amino acid at position 537 of the amino acid sequence of SEQ ID NO: 1;

(12) the amino acid corresponding to the amino acid at position 582 of the amino acid sequence of SEQ ID NO: 1; and

(13) the amino acid corresponding to the amino acid at position 583 of the amino acid sequence of SEQ ID NO: 1; and (ii) a step of constructing an amino acid sequence wherein the amino acid sequence specified in the step (i) is substituted with another amino acid in the amino acid sequence of the enzyme to be mutated.

[20] The designing method according to [19], wherein the enzyme to be mutated is a microorganism-derived glucose oxidase, and the amino acid substituted in the step (i) is the amino acid (3), the amino acid (5), the amino acid (7) or the amino acid (12), or a combination of at least two amino acids selected from these amino acids.

[21] The designing method according to [19], wherein the enzyme to be mutated is a microorganism-derived glucose oxidase, and the amino acid substituted in the step (i) is the amino acid (3), the amino acid (7) or the amino acid (12), or a combination of at least two amino acids selected from these amino acids.

[22] The designing method according to [19], wherein the enzyme to be mutated is a microorganism-derived glucose oxidase, and the amino acids substituted in the step (i) are the amino acid (7) and the amino acid (12).

[23] The designing method according to any one of [20] to [22], wherein the microorganism-derived glucose oxidase is a glucose oxidase of *Aspergillus niger* or *Penicillium amagasakiense*.

[24] The designing method according to [23], wherein the amino acid sequence of the glucose oxidase is the amino acid sequence of SEQ ID NO: 1 or 2.

[25] The designing method according to [19], wherein the enzyme to be mutated is a flavin adenine dinucleotide-dependent glucose dehydrogenase of *Penicillium italicum, Penicillium lilacinoechinulatum, Aspergillus oryzae* or *Aspergillus terreus*.

[26] The designing method according to [25], wherein the amino acid sequence of the flavin adenine dinucleotide-dependent glucose dehydrogenase is any one of the amino acid sequences of SEQ ID NOs: 3 to 6.

[27] A method for preparing a mutated enzyme, including the following steps (I) to (III):

(I) a step of preparing a nucleic acid coding for any one of the amino acid sequences of SEQ ID NOs: 7 to 21 and 59 to 61 or an amino acid sequence constructed in the designing method according to any one of [19] to [26];

(II) a step of expressing the nucleic acid; and (III) a step of recovering the expression product.

BRIEF DESCRIPTION OF THE DRAWINGS

FIG. 1 shows comparison between an amino acid sequence of an *Aspergillus niger*-derived GO and an amino acid sequence of a *Penicillium amagasakiense*-derived GO. Amino acids to be mutated were shown with underlines. Amino acids that were effective to GDH activity improvement among the amino acids to be mutated were shown with boldface. Arrows indicate amino acids of the active site. "*" denotes identical, ":" denotes conserved substitutions, and "." denotes semi-conserved substitutions.

FIG. 2 shows comparison between an amino acid sequence of a microorganism-derived GO and amino acid sequences of microorganism-derived FAD-GDHs. The amino acid sequence of *Penicillium italicum*-derived FAD-GDH (N-terminal side portion in SEQ ID NO: 3), the amino acid sequence of *Penicillium lilacinoechinulatum*-derived FAD-GDH (N-terminal side portion in SEQ ID NO: 4), the amino acid sequence of *Aspergillus oryzae*-derived FAD-GDH (N-terminal side portion in SEQ ID NO: 5), the amino acid sequence of *Aspergillus terreus*-derived FAD-GDH (N-terminal side portion in SEQ ID NO: 6), and the amino acid sequence of *Aspergillus niger*-derived GO (N-terminal side portion in SEQ ID NO: 1) are shown in this order from the upper column. Among amino acids around the active site of the GO, amino acids which are conserved among the FAD- GDHs (having high commonality) but are different between the GO and the FAD-GDHs were shown with underlines and numbers were assigned to the amino acids in the order from N-terminal sides.

FIG. 3 shows comparison between an amino acid sequence of a microorganism-derived GO and amino acid sequences of microorganism-derived FAD-GDHs (continuation of FIG. 2). The amino acid sequence of *Penicillium italicum*-derived FAD-GDH (C-terminal side portion in SEQ ID NO: 3), the amino acid sequence of *Penicillium lilacinoechinulatum*-derived FAD-GDH (C-terminal side portion in SEQ ID NO: 4), the amino acid sequence of *Aspergillus oryzae* FAD-GDH-derived (C-terminal side portion in SEQ ID NO: 5), the amino acid sequence of *Aspergillus terreus*-derived FAD-GDH (C-terminal side portion in SEQ ID NO: 6), and the amino acid sequence of *Aspergillus niger*-derived GO (C-terminal side portion in SEQ ID NO: 1) are shown in this order from the upper column. Among amino acids around the active center of the GO, amino acids which are conserved among the FAD-GDHs (having high commonality) but are different between the GO and the FAD-GDHs were shown with underlines and numbers were assigned to the amino acids in the order from N-terminal sides. Arrows indicate amino acids of the active site of the GO.

FIG. 4 shows the sequence (SEQ ID NO: 37) containing a gene sequence of an *Aspergillus niger*-derived GO amplified in PCR. A HindIII restriction enzyme site (boxed) and a Kozak sequence (underlined) are added to the 5'-terminal, and a XhoI restriction enzyme site (boxed) is added to the 3'-terminal. Note that due to addition of the Kozak sequence, the second amino acid is changed to serine from glutamine. The gene sequence of the *Aspergillus niger*-derived GO is set forth in SEQ ID NO: 38.

FIG. 6 is a table showing results of observation of activities in liquid culture. Among mutated enzyme-transformant, those showing positive colonies (which did not color in a GO assay, and colored in a GDH assay) were subjected to liquid culture, and GO activity and GDH activity were compared. The transformant having both of a high GDH activity and a high ratio of GDH activity and GO activity (GDH activity/GO activity) as compared to an unmutated (pYES-GO) were shown with shade. In the table, pYES-GO denotes a transformant obtained by transformation with unmutated enzyme, pYES2 denotes a transformant obtained by transformation with a plasmid before inserting a gene, GO denotes GO "Amano" 2 (Amano Enzyme Inc.), and FAD-GDH denotes GDH "Amano" 8 (Amano Enzyme Inc.), respectively.

FIG. 8 is a table showing mutation of mutated enzyme-transformants in which large changes were observed in GDH/GO activity ratios. T353H of 5-1-5 was presumed to be caused by mixing. Similarly, D446S of 7-2-17 and D446R of 7-2-42 were presumed to be also caused by mixing.

FIG. 10 is a table showing amino acids to be mutated in respective enzymes. (1) The amino acid corresponding to the amino acid at position 115 of the amino acid sequence of SEQ ID NO: 1; (2) the amino acid corresponding to the amino acid at position 131 of the amino acid sequence of SEQ ID NO: 1; (3) the amino acid corresponding to the amino acid at position 132 of the amino acid sequence of SEQ ID NO: 1; (4) the amino acid corresponding to the amino acid at position 193 of the amino acid sequence of SEQ ID NO: 1; (5) the amino acid corresponding to the amino acid at position 353 of the amino acid sequence of SEQ ID NO: 1; (6) the amino acid corresponding to the amino acid at position 436 of the amino acid sequence of SEQ ID NO: 1; (7) the amino acid corresponding to the amino acid at position 446 of the amino acid sequence of SEQ ID NO: 1; (8) the amino acid corresponding to the amino acid at position 472 of the amino acid sequence of SEQ ID NO: 1; (9) the amino acid corresponding to the amino acid at position 511 of the amino acid sequence of SEQ ID NO: 1; (10) the amino acid corresponding to the amino acid at position 535 of the amino acid sequence of SEQ ID NO: 1; (11) the amino acid corresponding to the amino acid at position 537 of the amino acid sequence of SEQ ID NO: 1; (12) the amino acid corresponding to the amino acid at position 582 of the amino acid sequence of SEQ ID NO: 1; and (13) the amino acid corresponding to the amino acid at position 583 of the amino acid sequence of SEQ ID NO: 1 were shown with each enzyme.

FIG. 11 shows comparison of activities of multiply-mutated GO. GDH/GO activity ratios of various transfomant having different combinations of mutation were compared using culture supernatants as samples. Mutation contained in each mutated enzyme-transfomant was shown with open circle.

FIG. 12 shows specific activities of mutated enzymes produced from mutated enzyme-transfomant having effective combinations of mutation. Mutation contained in each mutated enzyme-transfomant was shown with open circle.

FIG. 14 shows comparison of activities of D446 and V582 multiply-mutated enzymes. GDH/GO activity ratios were compared in various enzymes having different amino acids after substitution. *: GO activity falls below the detection limit.

DETAILED DESCRIPTION OF THE INVENTION

Figure 5:
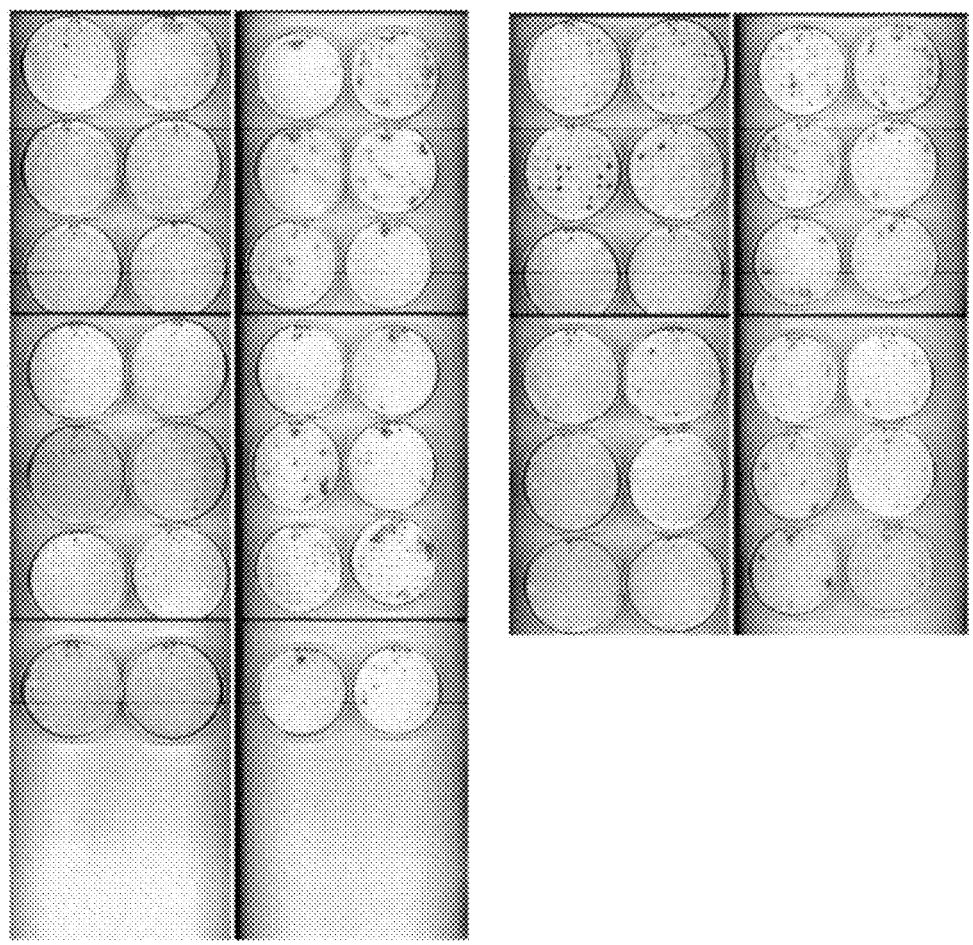
FIG. 5 shows results of a plate assay. A library (*Saccharomyces cerevisiae*) containing a plasmid into which mutation is introduced was prepared and a grown colony was replicated in an expression plate to then examine GO activity and GHD activity in a plate assay.

For the sake of explanation, a part of terms used with respect to the present invention will be defined below.
(Terms)
The term "mutated enzyme" means an enzyme obtained by mutation or modification of "an enzyme to be a base" by a technique disclosed in the present specification. "Mutated enzyme", "mutant-type enzyme" and "modified enzyme" are used interchangeably. An enzyme to be a base is typically a wild type enzyme, which, however, does not hinder an application of an enzyme that has been already subjected to an artificial operation as the "enzyme to be a base". Note that the "enzyme to be a base" is also called "an enzyme to be mutated" or "a target enzyme" in the specification.

Approximating a certain enzyme (for the sake of explanation, called the enzyme A) to another enzyme (for the sake of explanation, called the enzyme B), that is, modifying one or more characteristics of the enzyme A in order to approach to the corresponding characteristics of the enzyme B, is referred to as "making the enzyme A resemble the enzyme B". Examples of "characteristics" herein include enzyme activity (for example, glucose oxidase activity when the enzyme A is a glucose oxidase), substrate specificity, temperature characteristics (such as optimum temperature and temperature stability), pH characteristics (such as optimum pH and pH stability), coenzyme specificity, and reactivity to a mediator.

(Enzyme Obtained by Mutating Glucose Oxidase)

The first aspect of the present invention relates to an enzyme that is obtained by mutating a microorganism-derived glucose oxidase (GO) (hereinafter also referred to as "mutated GO"). The mutated GO of the present invention has an amino acid sequence wherein one or at least two amino acids selected from the group consisting of (1) to (13) are substituted with another amino acid in the amino acid sequence of a microorganism-derived GO (enzyme to be mutated):

(1) the amino acid corresponding to the amino acid at position 115 of the amino acid sequence of SEQ ID NO: 1;
(2) the amino acid corresponding to the amino acid at position 131 of the amino acid sequence of SEQ ID NO: 1;
(3) the amino acid corresponding to the amino acid at position 132 of the amino acid sequence of SEQ ID NO: 1;
(4) the amino acid corresponding to the amino acid at position 193 of the amino acid sequence of SEQ ID NO: 1;
(5) the amino acid corresponding to the amino acid at position 353 of the amino acid sequence of SEQ ID NO: 1;
(6) the amino acid corresponding to the amino acid at position 436 of the amino acid sequence of SEQ ID NO: 1;
(7) the amino acid corresponding to the amino acid at position 446 of the amino acid sequence of SEQ ID NO: 1;
(8) the amino acid corresponding to the amino acid at position 472 of the amino acid sequence of SEQ ID NO: 1;
(9) the amino acid corresponding to the amino acid at position 511 of the amino acid sequence of SEQ ID NO: 1;
(10) the amino acid corresponding to the amino acid at position 535 of the amino acid sequence of SEQ ID NO: 1;
(11) the amino acid corresponding to the amino acid at position 537 of the amino acid sequence of SEQ ID NO: 1;
(12) the amino acid corresponding to the amino acid at position 582 of the amino acid sequence of SEQ ID NO: 1; and
(13) the amino acid corresponding to the amino acid at position 583 of the amino acid sequence of SEQ ID NO: 1.

As shown in examples described later, the amino acid at position 115, amino acid at position 131, amino acid at position 132, amino acid at position 193, amino acid at position 353, amino acid at position 436, amino acid at position 446, amino acid at position 472, amino acid at position 511, amino acid at position 535, amino acid at position 537, amino acid at position 582, and amino acid at position and 583, which are mentioned above, are amino acids found by comparison between an *Aspergillus niger*-derived GO and various kinds of FAD-GDHs, are present around at the active site of the GO and distinctive to the GO. In the present invention, by mutating amino acids corresponding to those amino acids, which are supposed to have an important role in characteristics of GO, modification and improvement of characteristics of the enzyme are achieved.

Herein, the term "corresponding" when used for an amino acid residue in the present specification means contributing equally to exhibition of functions among proteins (enzymes) being compared. For example, when an amino acid sequence for comparison to the base amino acid sequence (that is, the amino acid sequence set forth in SEQ ID NO: 1) is aligned while considering partial homology of the primary structure (that is, an amino acid sequence) so that the most appropriate comparison can be achieved (in this event, the alignment may be optimized by introducing gaps if necessary), an amino acid located at a position corresponding to a specific amino acid in the base amino acid sequence can be specified as a "corresponding amino acid". The "corresponding amino acid" can also be specified by comparison between conformations (three-dimensional structures) in place of or in addition to the comparison between primary structures. Utilization of conformational information can give highly credible comparison results. In this case, a technique of performing an alignment with comparing atomic coordinates of conformations of a plurality of enzymes can be adopted. Conformational information of an enzyme to be mutated is available from, for example, the Protein Data Bank (http://www.pdbj.org/index_j.html).

One example of a method for determination of a protein conformation by the X-ray crystal structure analysis will be shown below.

(1) A protein is crystallized. Crystallization is essential to determine a conformation, and in addition, crystallization is industrially useful as a purification method of a protein at high purity and a stable preservation method of a protein at high density. In this case, it is preferable that a protein to which a substrate or its analogous compound as a ligand is bound is used for crystallization.

(2) The prepared crystal is irradiated with X-ray to collect diffraction data. There are many cases that a protein crystal is damaged due to X-ray irradiation and the diffraction ability is deteriorated. In such cases, a low-temperature measurement technique of rapidly cooling the crystal to about −173° C. and collecting diffraction data in the state has recently prevailed. In addition, ultimately, synchrotron orbit radiation having high luminance is utilized to collect high resolution data that is used for structural determination.

(3) In addition to the diffraction data, phase information is necessary in order to perform the crystal structure analysis. When a crystal structure of an analogous protein to a desired protein is unknown, it is impossible to determine the structure in a molecular substitution method, and a phase problem has to be solved by a heavy-atom isomorphous replacement method. The heavy-atom isomorphous replacement method is a method in which a metallic atom having a high atomic number such as mercury or platinum is introduced into a crystal and contribution of a large X-ray scattering ability of such a metallic atom to X ray diffraction data is utilized to collect phase information. The determined phase is possibly improved by smoothing an electron density of a solvent region in the crystal. Since a water molecule in the solvent region has large fluctuation, the electron density is hardly observed, and thus adjusting the electron density in this region to close to 0 makes it possible to approach the real electron density, which results in improving a phase. When plural molecules are contained in an asymmetrical unit, equation of electron densities of these molecules makes it possible to more significantly improve a phase. A model of a protein is fit to an electron density map calculated using the phase improved as described above. This process is performed on computer graphics using a program such as QUANTA made by MSI Co. (USA). After the process, structure refinement is performed using a program such as X-PLOR made by MSI Co. to complete the structure analysis. When a crystal structure of an analogous protein to a desired protein is known, it can be determined in a molecular substitution method using the atomic coordinate of the known protein. Molecular substitution and structure refinement can be performed using a program such as CNS_SOLVE ver.11.

Examples of a microorganism-derived GO that is an enzyme to be mutated include an *Aspergillus niger*-derived GO and a *Penicillium amagasakiense*-derived GO. The amino acid sequence of *Aspergillus niger*-derived GO and the amino acid sequence of a *Penicillium amagasakiense*-derived GO, which are registered in the public database, are set forth in SEQ ID NO: 1 and SEQ ID NO: 2, respectively. In addition, alignment comparison of these two amino acid sequences is shown in FIG. 1.

When the *Aspergillus niger*-derived GO having the amino acid sequence of SEQ ID NO: 1 is an enzyme to be mutated, the amino acid (1) is the amino acid at position 115 in SEQ ID NO: 1, the amino acid (2) is the amino acid at position 131 in SEQ ID NO: 1, the amino acid (3) is the amino acid at position 132 in SEQ ID NO: 1, the amino acid (4) is the amino acid at position 193 in SEQ ID NO: 1, the amino acid (5) is the amino acid at position 353 in SEQ ID NO: 1, the amino acid (6) is the amino acid at position 436 in SEQ ID NO: 1, the amino acid (7) is the amino acid at position 446 in SEQ ID NO: 1, the amino acid (8) is the amino acid at position 472 in SEQ ID NO: 1, the amino acid (9) is the amino acid at position 511 in SEQ ID NO: 1, the amino acid (10) is the amino acid at position 535 in SEQ ID NO: 1, the amino acid (11) is the amino acid at position 537 in SEQ ID NO: 1, the amino acid (12) is the amino acid at position 582 in SEQ ID NO: 1, and the amino acid (13) is the amino acid at position and 583 in SEQ ID NO: 1.

On the other hand, when a *Penicillium amagasakiense*-derived GO having the amino acid sequence of SEQ ID NO: 2 is an enzyme to be mutated, the amino acid (1) is the amino acid at position 115 in SEQ ID NO: 2, the amino acid (2) is the amino acid at position 131 in SEQ ID NO: 2, the amino acid (3) is the amino acid at position 132 in SEQ ID NO: 2, the amino acid (4) is the amino acid at position 193 in SEQ ID NO: 2, the amino acid (5) is the amino acid at position 353 in SEQ ID NO: 2, the amino acid (6) is the amino acid at position 436 in SEQ ID NO: 2, the amino acid (7) is the amino acid at position 446 in SEQ ID NO: 2, the amino acid (8) is the amino acid at position 472 in SEQ ID NO: 2, the amino acid (9) is the amino acid at position 511 in SEQ ID NO: 2, the amino acid (10) is the amino acid at position 535 in SEQ ID NO: 2, the amino acid (11) is the amino acid at position 537 in SEQ ID NO: 2, the amino acid (12) is the amino acid at position 582 in SEQ ID NO: 2, and the amino acid (13) is the amino acid at position and 583 in SEQ ID NO: 2.

An amino acid to be substituted is preferably the amino acid (3), the amino acid (5), the amino acid (7) or the amino acid (12). These are amino acids which have been confirmed to be effective to improvement of GDH activity, as shown in examples described later. In a mutated GO in which at least one of these amino acids is substituted, higher GDH activity can be exhibited as compared to the enzyme before mutation. A specific example of a mutated GO in which the amino acid (3) is substituted is an enzyme containing the amino acid sequence of SEQ ID NO: 7. In the same manner, a specific example of a mutated GO in which the amino acid (5) is substituted is an enzyme containing the amino acid sequence of SEQ ID NO: 8, a specific example of a mutated GO in which the amino acid (7) is substituted is an enzyme containing the amino acid sequence of SEQ ID NO: 9, and a specific example of a mutated GO in which the amino acid (12) is substituted is an enzyme containing the amino acid sequence of SEQ ID NO: 10. These mutated GOs all show higher GDH activities as compared to the *Aspergillus niger*-derived GO that is the enzyme before mutation.

A kind of an amino acid after substitution is not particularly limited and preferably selected so as not to correspond to so-called "conservative amino acid substitution". The "conservative amino acid substitution" herein refers to substituting a certain amino acid residue with an amino acid residue having a side chain with the same characteristics. Amino acid residues are classified into some families according to their side chains, such as basic side chains (e.g., lysine, arginine, and histidine), acidic side chains (e.g., asparaginic acid, and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). The conservative amino acid substitution is typically substitution between amino acid residues in the same family.

Examples of an amino acid after substitution include alanine for the amino acid (3), alanine for the amino acid (5), histidine for the amino acid (7), and serine, arginine, leucine and proline for the amino acid (12).

Among the above described amino acids (1) to (13), two or more amino acids may be substituted. Examples of combinations of amino acids to be substituted are listed below:
  Combination of (3) and (5)
  Combination of (3) and (7)
  Combination of (3) and (12)
  Combination of (5) and (7)
  Combination of (5) and (12)
  Combination of (7) and (12)
  Combination of (3), (5) and (7)
  Combination of (3), (5) and (12)
  Combination of (3), (7) and (12)
  Combination of (5), (7) and (12)
  Combination of (3), (5), (7) and (12)

Examples of amino acid sequences of mutated enzymes obtained by applying the above described combinations are shown in SEQ ID NOs: 11 to 21. These sequences are amino acid sequences of mutated GOs obtained by applying the above described combinations to the *Aspergillus niger*-derived GO. The relationships between SEQ ID NOs and combinations of mutation are as follows.
  SEQ ID NO: 11: Combination of (3) and (5)
  SEQ ID NO: 12: Combination of (3) and (7)
  SEQ ID NO: 13: Combination of (3) and (12)
  SEQ ID NO: 14: Combination of (5) and (7)
  SEQ ID NO: 15: Combination of (5) and (12)
  SEQ ID NO: 16: Combination of (7) and (12)
  SEQ ID NO: 17: Combination of (3), (5) and (7)
  SEQ ID NO: 18: Combination of (3), (5) and (12)
  SEQ ID NO: 19: Combination of (3), (7) and (12)
  SEQ ID NO: 20: Combination of (5), (7) and (12)
  SEQ ID NO: 21: Combination of (3), (5), (7) and (12)
  SEQ ID NO: 59: Combination of (7) and (12)
  SEQ ID NO: 60: Combination of (7) and (12)
  SEQ ID NO: 61: Combination of (7) and (12)

Considering the experimental results shown in examples described later (confirmation of effects of mutation combinations), combination of (3) and (12), combination of (7) and (12), and combination of (3), (7) and (12) are preferable among the above combinations. A particularly preferable combination is combination of (7) and (12) (specific examples of amino acid sequences of mutated enzymes in this combination are SEQ ID NOs: 16 and 59 to 61 as described above). An amino acid after substitution is preferably histidine for the amino acid (7), and preferably serine (SEQ ID NO: 16), arginine (SEQ ID NO: 59), leucine (SEQ ID NO: 60) or proline (SEQ ID NO: 61) for the amino acid (12). For the amino acid (12), an amino acid after substitution is particularly preferably proline.

Generally, when a part of an amino acid sequence of a certain protein is modified, the modified protein may have the equal function to that of the protein before the modification. That is to say, the modification of the amino acid sequence may not have a substantial effect on the function of the protein, so that the function of the protein may be maintained before and after the modification. When this technical common sense is considered, an enzyme that has a recognizable slight difference in the amino acid sequence (provided that the difference occurs in sites other than the sites in which the above substitutions have been made) and has no substantially recognizable difference in the function can be regarded as an enzyme that is substantially the same as the above mutated GO in comparison with the mutated GO comprising the amino acid sequence in which one or more amino acids selected from the group consisting of the above (1) to (13) have been substituted with another amino acid. The term "slight difference in the amino acid sequence" as used herein typically means that the amino acid sequence is mutated (changed) by the deletion or substitution of one to several amino acids (the upper limit: e.g. 3, 5, 7, or 10 amino acids) constituting the amino acid sequence, or by the addition, insertion, or combination thereof, of one to several amino acids (the upper limit: e.g. 3, 5, 7, or 10 amino acids). The identity (%) of between the amino acid sequence in the "substantially the same enzyme" and the amino acid sequence of the above mutated GO as a standard is preferably 90% or more, more preferably 95% or more, yet more preferably 98% or more, and most preferably 99% or more. In addition, the difference in the amino acid sequence may occur in a plurality of positions. The "slight difference in the amino acid sequences" is preferably generated by a conservative amino acid substitution.

(Nucleic Acid Coding for Mutated GO, Etc.)

The second aspect of the present invention provides a nucleic acid relating to the mutated GO of the invention. That is, provided are a gene coding for the mutated GO, a nucleic acid that can be used as a probe for identifying a nucleic acid coding for the mutated GO, and a nucleic acid that can be used as a primer for amplifying or mutating a nucleic acid coding for the mutated GO.

The gene coding for a mutated GO is typically used in preparation of the mutated GO. According to a genetic engineering procedure using the gene coding for a mutated GO, a mutated GO in a more homogeneous state can be obtained. Further, the method can be a preferable method also in the case of preparing a large amount of a mutated GO. Note that uses of the gene coding for a mutated GO are not limited to preparation of a mutated GO. For example, the nucleic acid can also be used as a tool for an experiment intended for clarification of action mechanisms of a mutated GO or a tool for designing or preparing a further mutant of an enzyme.

The "gene coding for a mutated GO" herein refers to a nucleic acid capable of obtaining the mutated GO when it is expressed, and includes, as a matter of course of a nucleic acid having a nucleotide sequence corresponding to the amino acid sequence of the mutated GO, also a nucleic acid obtained by adding a sequence that does not code for an amino acid sequence to such a nucleic acid. Degeneracy of a codon is also considered.

Examples of sequences of genes coding for the mutated GO are shown in SEQ ID NOs: 22 to 36 and 62 to 64. These sequences are genes coding for the mutated GO obtained by specific amino acids substitution to *Aspergillus niger* GO. Amino acid substitution in each sequence is as follows.

SEQ ID NO: 22: T132A
SEQ ID NO: 23: T353A
SEQ ID NO: 24: D446H
SEQ ID NO: 25: V582S
SEQ ID NO: 26: T132A and T353A
SEQ ID NO: 27: T132A and D446H
SEQ ID NO: 28: T132A and V582S
SEQ ID NO: 29: T353A and D446H
SEQ ID NO: 30: T353A and V582S
SEQ ID NO: 31: D446H and V582S
SEQ ID NO: 32: T132A, T353A and D446H
SEQ ID NO: 33: T132A, T353A and V582S
SEQ ID NO: 34: T132A, D446H and V582S
SEQ ID NO: 35: T353A, D446H and V582S
SEQ ID NO: 36: T132A, T353A, D446H and V582S
SEQ ID NO: 62: D446H and V582R
SEQ ID NO: 63: D446H and V582L
SEQ ID NO: 64: D446H and V582P The nucleic acid of the present invention can be prepared in an isolated state by use of a standard genetic engineering technique, molecular biological technique, biochemical technique, and the like in reference to the present specification or the sequence information disclosed in the appended sequence listing.

Another embodiment of the present invention provides a nucleic acid different in a nucleotide sequence in a part (hereinafter also referred to as a "homologous nucleic acid", and a nucleotide sequence defining a homologous nucleic acid is also referred to as a "homologous nucleotide sequence") as compared to the nucleotide sequence of the gene coding for the mutated GO of the invention, although functions of a protein coded by the nucleic acid are equal. An example of the homologous nucleic acid includes a DNA composed of a nucleotide sequence containing substitution, deletion, insertion, addition or inversion of 1 to several nucleotides on the basis of the nucleotide sequence of the nucleic acid coding for the mutated GO of the present invention and coding for a protein having enzyme activity characteristic to the mutated GO (i.e. GDH activity). Substitution or deletion of bases may occur in a plurality of sites. The "plurality" herein depends on positions or kinds of amino acid residues in a conformation of a protein coded by the nucleic acid but means, for example, 2 to 40 bases, preferably 2 to 20 bases, and more preferably 2 to 10 bases.

Such a homologous nucleic acid as described above can be obtained by, for example, a restriction enzyme treatment, a treatment with exonuclease, DNA ligase, etc., and introduction of mutation by a site-directed mutagenesis method (Molecular Cloning, Third Edition, Chapter 13, Cold Spring Harbor Laboratory Press, New York), and a random mutagenesis method (Molecular Cloning, Third Edition, Chapter 13, Cold Spring Harbor Laboratory Press, New York). The homologous nucleic acid can be obtained also in other methods such as exposure to ultraviolet radiation.

Another embodiment of the present invention relates to a nucleic acid having the complementary nucleotide sequence to the nucleotide sequence of the gene coding for the mutated GO of the invention. Another embodiment of the present invention provides a nucleic acid having a nucleotide sequence with an identity of at least about 60%, 70%, 80%, 90%, 95%, 99%, or 99.9% to the nucleotide sequence of the gene coding for the mutated GO of the invention or the complementary nucleotide sequence Another embodiment of the present invention relates to a nucleic acid having a nucleotide sequence hybridizing to the complementary nucleotide sequence to the nucleotide sequence of the gene coding for the mutated GO of the invention or its homologous nucleotide sequence under stringent conditions. The "stringent conditions" herein refer to conditions wherein a so-called specific hybrid is formed and a nonspecific hybrid is not formed. Such stringent conditions are known by a person skilled in the art and can be set in reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization liquid (50% formamide, 10×SSC (0.15 M NaCl, 15 mM sodium citrate, pH 7.0), a 5×Denhardt solution, 1% SDS, 10% dextran sulfate, 10 μg/ml of modified salmon sperm DNA, and a 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), a 1×Denhardt solution, 1% SDS, 10% dextran sulfate, 10 μg/ml of modified salmon sperm DNA, and a 50 mM phosphate buffer (pH 7.5) as a hybridization liquid.

Another embodiment of the present invention provides a nucleic acid (nucleic acid fragment) having a part of the nucleotide sequence of the gene coding for the mutated GO of the invention or the complementary nucleotide sequence. Such a nucleic acid fragment can be used in detection, identification, and/or amplification of a nucleic acid having the nucleotide sequence of the gene coding for the mutated GO of the present invention. For example, the nucleic acid fragment is designed so as to at least contain a part being hybridized to a sequential nucleotide moiety (for example, about 10 to about 100 nucleotides length, preferably about 20 to about 100 bases length, more preferably about 30 to about 100 bases length) in the nucleotide sequence of the gene coding for the mutated GO of the invention. When used as a probe, the nucleic acid fragment can be labeled. Examples such as fluorescent substances, enzymes, and radioactive isotopes can be used for the labeling.

Another aspect of the present invention relates to a recombinant DNA containing the gene of the present invention (the gene coding for a mutated GO). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of a host cell. Examples include a M13 phage or an altered form thereof, a λ phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of the nucleic acid of the present invention into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

For the host cell, microorganisms such as *Escherichia coli* and budding yeasts (*Saccharomyces cerevisiae*) are preferably used from the viewpoint of easiness of handling, and host cells capable of duplicating a recombinant DNA and expressing a gene of a mutated GO can be used. Examples of *Escherichia coli* include *Escherichia coli* BL21(DE3)pLysS in the case of using a T7 promoter, and *Escherichia coli* JM109 in other cases. Examples of budding yeasts include budding yeast SHY2, AH22, or INVSc1 (Invitrogen Ltd.).

Another aspect of the present invention relates to a microorganism having the recombinant DNA of the invention (that is, a transformant). The microorganism of the invention can be obtained by transfection or transformation using the vector of the invention described above. The transfection or transformation can be performed in, for example, the calcium chloride method (J. Mol. Biol., 53, 159 (1970)), the Hanahan method (J. Mol. Biol., 166, 557 (1983)), the SEM method (Gene, 96, 23 (1990)), a method by Chung, et al. (Proc. Natl. Acad. Sci. U.S.A. 86, 2172 (1989)), the calcium phosphate coprecipitation method, the electroporation method (Potter, H. et al., Proc. Natl. Acad. Sci. U.S.A. 81, 7161-7165 (1984)), and the lipofectin method (Feigner, P. L. et al., Proc. Natl. Acad. Sci. U.S.A. 84, 7413-7417 (1984)). Note that the microorganism of the present invention can be used in producing the mutated GO of the present invention (see the section of the preparation method of mutated enzyme described later).

(Use of Mutated GO)

The third aspect of the present invention relates to a use of the mutated GO. In this aspect, firstly, a glucose measurement method using a mutated GO is provided. In the glucose measurement method of the present invention, a glucose amount in a sample is measured using a redox reaction by the present enzyme. The present invention is used, for example, in a measurement of a blood sugar level, a measurement of a glucose concentration in foods (such as seasonings, beverages, etc.), and the like. Furthermore, the present invention may be used in order to examine a fermentation degree in production steps of fermented foods (such as vinegar) or fermented beverages (such as beer and liquor).

The present invention also provides a glucose measuring reagent containing the present enzyme. The reagent is used in the above described glucose measurement method of the present invention.

The present invention further provides a kit for carrying out the glucose measurement method of the present invention (glucose measuring kit). The kit of the present invention contains a reaction reagent, a buffer solution, a glucose standard solution, and the like as arbitrary elements, other than a glucose measuring reagent containing the present enzyme. In addition, an instruction for use is generally appended to the glucose measuring kit of the present invention.

The present invention provides, as a further use, a method of reducing a glucose content by acting the mutated GO of the present invention on industrial products (e.g., various foods such as processed foods, confectionery, soft drinks, alcoholic beverages, and nutritional supplements; and cosmetics) or raw materials thereof, and an enzyme preparation that is used in the use. For example, when the mutated GO of the present invention is applied to foods, the Maillard reaction can be restrained due to decrease of a glucose content, and the like. The enzyme preparation of the present invention may contain a vehicle, a buffer, a suspending agent, a stabilizer, a preservative, a antiseptic agent, physiological saline, and the like, other than the active ingredient (mutated GO). For the vehicle, starch, dextrin, maltose, trehalose, lactose, D-glucose, sorbitol, D-mannitol, sucrose, glycerol, or the like can be used. For the buffer, phosphate, citrate, acetate, or the like can be used. For the stabilizer, propylene glycol, ascorbic acid, or the like can be used. For the preservative, phenol, benzalkonium chloride, benzyl alcohol, chlorobutanol, methyl paraben, or the like can be used. For the antiseptic agent, ethanol, benzalkonium chloride, parahydroxybenzoic acid, chlorobutanol, or the like can be used.

(Method of Designing Mutated Enzyme)

Another aspect of the present invention relates to a method of designing a mutated enzyme. In the designing method of the present invention, the following steps (i) and (ii) are carried out.

The step (i): one or at least two amino acids selected from the group below are specified in an amino acid sequence of an enzyme to be mutated that is a microorganism-derived glucose oxidase (microorganism-derived GO) or a microorganism-derived flavin adenine dinucleotide-dependent glucose dehydrogenase (microorganism-derived FDA-GDH):

(1) the amino acid corresponding to the amino acid at position 115 of the amino acid sequence of SEQ ID NO: 1;
(2) the amino acid corresponding to the amino acid at position 131 of the amino acid sequence of SEQ ID NO: 1;
(3) the amino acid corresponding to the amino acid at position 132 of the amino acid sequence of SEQ ID NO: 1;
(4) the amino acid corresponding to the amino acid at position 193 of the amino acid sequence of SEQ ID NO: 1;
(5) the amino acid corresponding to the amino acid at position 353 of the amino acid sequence of SEQ ID NO: 1;
(6) the amino acid corresponding to the amino acid at position 436 of the amino acid sequence of SEQ ID NO: 1;
(7) the amino acid corresponding to the amino acid at position 446 of the amino acid sequence of SEQ ID NO: 1;
(8) the amino acid corresponding to the amino acid at position 472 of the amino acid sequence of SEQ ID NO: 1;
(9) the amino acid corresponding to the amino acid at position 511 of the amino acid sequence of SEQ ID NO: 1;
(10) the amino acid corresponding to the amino acid at position 535 of the amino acid sequence of SEQ ID NO: 1;
(11) the amino acid corresponding to the amino acid at position 537 of the amino acid sequence of SEQ ID NO: 1;
(12) the amino acid corresponding to the amino acid at position 582 of the amino acid sequence of SEQ ID NO: 1; and
(13) the amino acid corresponding to the amino acid at position 583 of the amino acid sequence of SEQ ID NO: 1.

The above described amino acids (1) to (13) to be substituted were found by comparison between a microorganism-derived GO and plural kinds of microorganism-derived FAD-GDHs. Change of enzyme characteristics is expected due to substituting these amino acids. Examples of characteristics that can be changed are listed: GO activity, GDH activity, substrate specificity, temperature characteristics (such as optimum temperature, temperature stability), pH characteristics (optimum pH, pH stability), coenzyme specificity, and reactivity to a mediator.

An enzyme to be mutated in the designing method of the present invention is a microorganism-derived GO or a microorganism-derived FAD-GDH. The enzyme to be mutated is typically a wild-type enzyme (enzyme that is found in nature). However, such a condition does not inhibit a use of an enzyme that has already undergone any of mutation or modification. Examples of a microorganism-derived GO include *Aspergillus niger*-derived GO and *Penicillium amagasakiense*-derived GO, examples of a microorganism-derived FAD-GDH include *Penicillium italicum*-derived FAD-GDH, *Penicillium lilacinoechinulatum*-derived FAD-GDH, *Aspergillus oryzae*-derived FAD-GDH and *Aspergillus terreus*-derived FAD-GDH. As amino acid sequences of the enzymes exemplified herein, those registered in the public database are specified below. Note that an enzyme containing any one of the amino acid sequences is used as the enzyme to be mutated in a preferable embodiment.

*Aspergillus niger*-derived GO: the amino acid sequence of SEQ ID NO: 1
*Penicillium amagasakiense*-derived GO: the amino acid sequence of SEQ ID NO: 2
*Penicillium italicum*-derived FAD-GDH: the amino acid sequence of SEQ ID NO: 3
*Penicillium lilacinoechinulatum*-derived FAD-GDH: the amino acid sequence of SEQ ID NO: 4
*Aspergillus oryzae*-derived FAD-GDH: the amino acid sequence of SEQ ID NO: 5
*Aspergillus terreus*-derived FAD-GDH: the amino acid sequence of SEQ ID NO: 6

Note that amino acids corresponding to the above described amino acids (1) to (13) for the respective enzymes exemplified above will be collectively shown in the table in FIG. 10.

In the present invention, the following step (ii) is carried out after the step (i).

The step (ii): construction an amino acid sequence wherein the amino acid sequence specified in the step (i) is substituted with another amino acid in the amino acid sequence of the enzyme to be mutated.

A kind of the amino acid after substitution is not particularly limited. Therefore, either of conservative amino acid substitution or nonconservative amino acid substitution may be adopted. The "conservative amino acid substitution" herein refers to substituting a certain amino acid residue by an amino acid residue having a side chain with the same characteristics. Amino acid residues are classified into some families according to their side chains, such as basic side chains (e.g., lysine, arginine, and histidine), acidic side chains (e.g., asparaginic acid, and glutamic acid), uncharged polar side chains (e.g., asparagine, glutamine, serine, threonine, tyrosine, and cysteine), nonpolar side chains (e.g., glycine, alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, and tryptophan). The conservative amino acid substitution is preferably substitution between amino acid residues in the same family.

(Preparation Method of Mutated Enzyme)

A further aspect of the present invention relates to a preparation method of a mutated enzyme. In one embodiment of the preparation method of a mutated enzyme of the present invention, the mutated GO that the present inventors succeeded in obtaining is prepared in a genetic engineering technique. In the case of this embodiment, a nucleic acid coding for any one of the amino acid sequences of SEQ ID NOs: 7 to 10 is prepared (step (I)). Herein, "a nucleic acid coding for a specific amino acid sequence" is a nucleic acid capable of obtaining a polypeptide having the amino acid sequence in the case of being expressed, and as a matter of course of a nucleic acid having a nucleotide sequence corresponding to the amino acid sequence, may be a nucleic acid added with an extra sequence (may be a sequence coding for an amino acid sequence or a sequence not coding for an amino acid sequence). Degeneracy of a codon is also considered. "A nucleic acid coding for any one of the amino acid sequences of SEQ ID NOs: 7 to 10" can be prepared into a state of being isolated by using a standard genetic engineering technique, molecular biological technique, biochemical technique, and the like in reference to sequence information disclosed in the present specification or the appended sequence listing. Herein, all of the amino acid sequences of SEQ ID NOs: 7 to 10 are obtained by mutation to the amino acid sequence of the Aspergillus niger-derived GO. Therefore, a nucleic acid (gene) coding for any one of the amino acid sequences of SEQ ID NOs: 7 to 10 can be obtained also by adding necessary mutation to the gene coding for the Aspergillus niger-derived GO (SEQ ID NO: 38). A large number of methods for site-directed mutagenesis have been known in the present technical field (for example, see Molecular Cloning, Third Edition, Cold Spring Harbor Laboratory Press, New York), and among those methods, a suitable method can be selected to be used. A method of saturation mutagenesis can be adopted as the method of site-directed mutagenesis. The method of saturation mutagenesis is a "semi-rational, semi-random" technique of assuming a position which relates to a desired function based on a conformation of a protein and introducing amino acid saturation (J. Mol. Biol. 331, 585-592 (2003)). For example, use of a kit such as Quick change (Stratagene Corporation) and Overlap extension PCR (Nucleic Acid Res. 16, 7351-7367 (1988)) makes it possible to introduce position specific amino acid saturation. A Taq polymerase and the like can be used for a DNA polymerase used in PCR. Provided that a DNA polymerase having high precision such as KOD-PLUS—(TOYOBO CO., LTD.) or Pfu turbo (Stratagene Corporation) is preferably used.

In another embodiment of the present invention, a mutated enzyme is prepared based on an amino acid sequence that is designed by the designing method of the present invention. In the case of this embodiment, a nucleic acid coding for an amino acid sequence constructed by the designing method of the present invention is prepared in the step (i). For example, based on the amino acid sequence constructed by the designing method of the present invention, necessary mutation (that is, substitution of an amino acid in a specific position in a protein that is an expressed product) is added to a gene coding for an enzyme to be mutated and a nucleic acid (gene) coding for the mutated enzyme is obtained.

Following the step (I), the prepared nucleic acid is expressed (step (II)). For example, firstly, an expression vector inserted with the above described nucleic acid is prepared and a host cell is transformed using this constructed vector. The "expression vector" refers to a vector that can introduce a nucleic acid inserted therein into a desired cell (host cell) and is capable of being expressed in the cell. The expression vector generally contains a promoter sequence that is necessary for expression of an inserted nucleic acid, an enhancer sequence that promotes expression, and the like. An expression vector containing a selection marker can also be used. When such an expression vector is used, presence or absence (and its degree) of the expression vector can be confirmed by using a selection marker.

Then, a transformant is cultured under the condition of producing a mutated enzyme that is an expressed product. Culture of the transformant may follow a general method. An assimilable carbon compound may be used as a carbon source used for a medium, and examples such as glucose, sucrose, lactose, maltose, molasses, and pyruvic acid are used. An available nitrogen compound may be used as a nitrogen source, and examples such as peptone, meat extract, yeast extract, casein hydrolysate, and soybean bran alkali extract are used. Other than those substances, phosphate, carbonate, sulfate, salts of magnesium, calcium, potassium, iron, manganese and zinc, specific amino acids, specific vitamins, and the like are used according to necessity.

On the other hand, a culture temperature can be set within the range from 30 to 40° C. (preferably at around 37° C.). A culture time can be set by considering growing characteristics of a transformant to be cultured and production characteristics of a mutant-type enzyme. A pH of a medium is set within the range wherein a transformant grows and an enzyme is produced. The pH of a medium is preferably set at about 6.0 to 9.0 (preferably at around pH 7.0).

Subsequently, the expressed product (mutated enzyme) is recovered (step (III)). A culture liquid containing fungas bodies after culture may be used as an enzyme solution directly or after undergoing condensation, removal of impurities, or the like, but the expressed product is generally once recovered from the culture liquid or fungas bodies. When the expressed product is a secretion type protein, it can be recovered from the culture liquid, and in other cases, the expressed product can be recovered from cells. In the case of recovering from the culture liquid, for example, an undissolved substance is removed by filtration and centrifugation on a culture supernatant, and then, a purified product of a mutated enzyme can be obtained by separation and purification in combination of vacuum concentration, membrane concentration, salting out using ammonium sulfate or sodium sulfate, fractional precipitation by methanol, ethanol, or acetone, dialysis, heating treatment, isoelectric treatment, various kinds of chromatography such as gel filtration, adsorption chromatography, ion exchange chromatography, and affinity chromatography (for example, gel filtration with Sephadex gel (GE Healthcare Life Sciences), etc., DEAE sepharose CL-6B (GE Healthcare Life Sciences), octyl sepharose CL-6B (GE Healthcare Life Sciences), CM sepharose CL-6B (GE Healthcare Life Sciences)). On the other hand, in the case of recovering the expressed product from cells, a culture liquid is subjected to filtration, centrifugation, or the like, to thus obtain the cells, then the cells are crushed by a mechanical method such as a pressure treatment and an ultrasonic treatment, or an enzymatic method with a lysozyme or the like, thereafter carrying out separation and purification in the same manner as described above, and a purified product of a mutated enzyme can be thus obtained.

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

Generally, genetic expression and recovery of the expressed product (mutated enzyme) are carried our using an appropriate host-vector system as described above, but a cell-free synthesis system may also be employed. Herein, the "cell-free synthesis system (cell-free transcription system, cell-free transcription/translation system)" refers to in vitro synthesis of mRNA or a protein from a nucleic acid (DNA or mRNA) being a template, which codes for the mRNA or the protein, using a ribosome, a transcription/translation factor derived from living cells (alternately, obtained in a genetic engineering technique) or the like, not using living cells. In the cell-free synthesis system, a cell extraction obtained from a cell disruptor that is purified according to necessity is generally used. The cell extraction generally includes ribosome necessary for protein synthesis and various factors such as an initiation factor, and various enzymes such as tRNA. When a protein is synthesized, this cell extraction is added with other substances necessary for protein synthesis, such as various amino acids, energy sources (e.g., ATP and GTP), and creatine phosphate. As a matter of course, ribosome and various factors and/or various enzymes, and the like, which are separately prepared, may be supplemented if necessary in the protein synthesis.

Development of a transcription/translation system reconstructing various molecules (factors) necessary for protein synthesis has also been reported (Shimizu, Y. et al.: Nature Biotech., 19, 751-755, 2001). In this synthesis system, a gene of 31 kinds of factors composed of 3 kinds of initiation factors constituting a protein synthesis system of bacteria, 3 kinds of elongation factors, 4 kinds of factors associated with termination, 20 kinds of aminoacyl tRNA synthesis enzymes that make each amino acid combine with tRNA, and a methionyl tRNA formyl transfer enzyme is amplified from an *Escherichia coli* genome, and a protein synthesis system is reconstructed in vitro using them. Such a reconstructed synthesis system may be used in the present invention.

The term "cell-free transcription/translation system" is interchangeably used with a cell-free protein synthesis system, an in vitro translation system or an in vitro transcription/translation system. In the in vitro translation system, RNA is used as a template to synthesize a protein. Any of RNA, mRNA, an in vitro transcribed product, or the like is used as the template RNA. On the other hand, in the in vitro transcription/translation system, DNA is used as a template. The template DNA should include in a ribosome bonding region, and preferably contains a suitable terminator sequence. In addition, in the in vitro transcription/translation system, a condition of adding factors necessary for each reaction is established so that a transcription reaction and a translation reaction proceed sequentially.

EXAMPLES

For the purpose of creating GDH having high practicality, a new technique was sought in place of a conventional method (a method of modifying an existing GDH or a method of focusing on screening). Firstly, a glucose oxidase (GO) which does not have a specific problem to FAD-GDH (such as comparatively high reactivity to xylose, high optimum temperature) has been focused. It has been known that GO and FAD-GDH have comparatively high homology in the amino acid sequences. Drawing attention on the homology, a new approach such as conferring GDH activity to GO, that is, making GO resemble GDH, was employed.

1. Alignment Comparison of GO and FAD-GDH

From alignment comparison using an *Aspergillus niger*-derived GO and an *Aspergillus oryzae*, *Aspergillus terreus*, *Penicillium italicum*, or *Penicillium lilacinoechinulatum*-derived FAD-GDHs, which are currently known for their amino acid sequences, and the conformation of the *Aspergillus niger*-derived GO, which has been already clarified in the conformation, amino acids that are conserved among the FAD-GDHs (having high commonality) but different between the GO and the FAD-GDHs in amino acids around the active center of the GO were searched (FIGS. 2 and 3). Note that, for alignment comparison, Clustal W2 was used (a special site is provided in the website of EMBL (European Molecular Biology Laboratory)-EBI (European Bioinformatics Institute); http://www.ebi.ac.uk/Tools/clustalw2/index.html).

Thirteen amino acids identified by the search (L115, G131, T132, V193, T353, F436, D446, Y472, I511, P535, Y537, V582, M583) were used as samples to be introduced with mutation.

2. Preparation of GO Gene, Introduction of Mutation and Plate Assay

For a GO gene, because of no report of expressing in *Escherichia coli* in the past, a GO gene was inserted into a HindIII-XhoI portion of pYES2 (Invitrogen Ltd.) to be expressed using *Saccharomyces cerevisiae* (*S. cerevisiae*) as a host.

A genomic DNA was extracted from the *Aspergillus niger* GO-1 strain (possessed by Amano Enzyme Inc.), using a Gen Elute Plant Genomic DNA kit (Sigma Co.) and a GO gene was then obtained by PCR. The conditions of the PCR are shown in the following.

(Composition of Reaction Solution)
  10×LA buffer (TAKARA BIO INC.) 5 μL
  2.5 mM dNTPs (TAKARA BIO INC.) 8 μL
  25 mM $MgCl_2$ (TAKARA BIO INC.) 5 μL
  Forward primer (50 μM) 1 μL
  Reverse primer (50 μM) 1 μL
  Template 1 μL
  LA Taq (TAKARA BIO INC.) 0.5 μL
  $stH_2O$ 28.5 μL
(Sequences of Primers)

```
Forward primer:
                                    (SEQ ID NO: 39)
GATCAGAAGCTTAAAAAAATGTCTACTCTCCTTGTGAGCTCG Reverse primer:
                                    (SEQ ID NO: 40)
GATCAGCTCGAGTCACTGCATGGAAGCATAATC
```

(Reaction Conditions)

After reacting at 94° C. for 2 minutes, reaction cycles at 94° C. for 30 seconds, at 52° C. for 30 seconds, and at 72° C. for 2 minutes were repeated 35 times, thereafter reacting at 72° C. for 7 minutes and finally leaving at 4° C.

Figure 4:
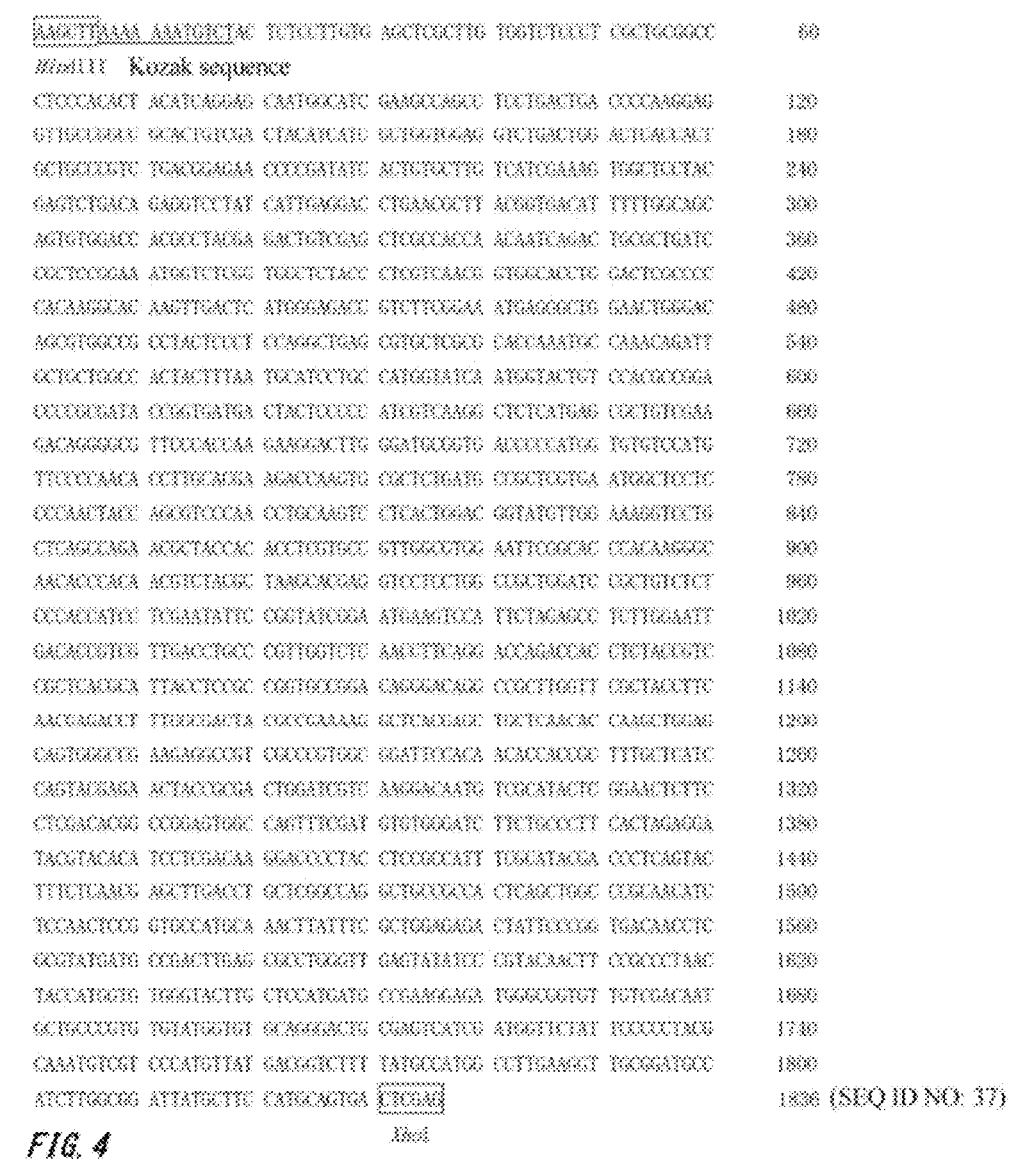

An amplified product after PCR was inserted into pYES2 to form a pYES-GO-K-P-2 plasmid, to confirm the sequence of the insert (FIG. 4). From the viewpoint that no problem was found in the sequence, an operation for mutation was carried out to construct a plasmid having a mutant glucose oxidase based on the following synthesized oligonucleotides in which L115, G131, T132, V193, T353, F436, D446, Y472, I511, P535, Y537, V582, and M583 were designed to be substituted with plural kinds of amino acids, respectively, and synthesized oligonucleotides complementary thereto, using the constructed pYES-GO-K-P-2 plasmid as a template, according to the attached protocol with a QuikChange Site-Directed Mutagensesis Kit (Stratagene co.).

```
primer for GO-L115-mutation:
                                    (SEQ ID NO: 41)
CCACCAACAATCAGACTGCGNNNATCCGCTCCGGAAATGG primer for GO-G131-mutation:
                                    (SEQ ID NO: 42)
GCTCTACCCTCGTCAACGGTNNNACCTGGACTCGCCCC primer for GO-T132-mutation:
                                    (SEQ ID NO: 43)
CTCGTCAACGGTGGCNNNTGGACTCGCCCCCAC primer for GO-V193-mutation:
                                    (SEQ ID NO: 44)
CATGGTATCAATGGTACTNNNCACGCCGGACCCCGCG primer for GO-T353-mutation:
                                    (SEQ ID NO: 45)
CAACCTTCAGGACCAGACNNNTCTACCGTCCGCTCAC primer for GO-F436-mutation:
                                    (SEQ ID NO: 46)
GTCGCATACTCGGAACTCNNNCTCGACACGGCCGGAG primer for GO-D446-mutation:
                                    (SEQ ID NO: 47)
GCCGGAGTGGCCAGTTTCNNNGTGTGGGATCTTCTGC primer for GO-Y472-mutation:
                                    (SEQ ID NO: 48)
CATCCTCCGCCATTTCGCANNNGACCCTCAGTACTTTCTCAAC primer for GO-I551-mutation:
                                    (SEQ ID NO: 49)
CTTATTTCGCTGGAGAGACTNNNCCCGGTGACAACCTCGC primer for GO-P535-mutation:
                                    (SEQ ID NO: 50)
CCCGTACAACTTCCGCNNNAACTACCATGGTGTGGGTACTTG primer for GO-Y537-mutation:
                                    (SEQ ID NO: 51)
GTACAACTTCCGCCCTAACNNNCATGGTGTGGGTACTTGCTC primer for GO-V582-mutation:
                                    (SEQ ID NO: 52)
CTACGCAAATGTCGTCCCATNNNATGACGGTCTTTTATGCCATGG primer for GO-M583-mutation:
                                    (SEQ ID NO: 53)
CTACGCAAATGTCGTCCCATGTTNNNACGGTCTTTTATGCCATGG
```

*Escherichia coli* DH5α was transformed with the plasmid after mutation introduction, and plasmid extraction was carried out to prepare a mutant library. *Saccharomyces cerevisiae* INVSc1 (Invitrogen Ltd.) was transformed with the obtained library, and the grown colony was replicated in an expression plate, to then confirm expression and mutation introduction by a plate assay (FIG. 5). For F436, growth of a mutated enzyme-transformant could not be observed. Note that the manual of pYES2 was used as a reference for the experimental operations.

Plate Assay Method

Each coloring liquid was immersed into 80 mm-filter paper and then placed on a plate to observe color development.

<GO Assay>

50 mM PIPES-NaOH (cont. 0.1% Triton X-100) pH 7.0 20 mL

10% glucose 5 mL 25 u/mL PO "Amano" 3 (Amano Enzyme Inc.) 5 mL o-dianidine 5 mg

<GDH Assay>

50 mM PIPES-NaOH (cont. 0.1% Triton X-100) pH 7.0 23 mL

10% glucose 5 mL 3 mmol/L 1-methoxy PMS 1 mL 6.6 mmol/L NTB 1 mL

3. Confirmation of Activity in Liquid Culture

A positive colony observed in the plate assay (which did not develop color in the GO assay and developed color in the GDH assay) was subjected to liquid culture to examine GO activity and GDH activity. Note that the manual of pYES2 was used as a reference for the experimental operations.

<GO Assay Reagents>

Phenol-containing phosphoric acid buffer solution 19 mL

10% glucose 5 mL 25 u/mL PO "Amano" 3 (Amano Enzyme Inc.) 5 mL 0.4 g/dL 4-aminoantipyrine 1 mL <GDH Assay Reagents>

50 mM PIPES-NaOH (cont. 0.1% Triton X-100) pH 7.0 21 mL

10% glucose 5 mL 3 mmol/L PMS 3 mL 6.6 mmol/L NTB 1 mL

Figure 7:
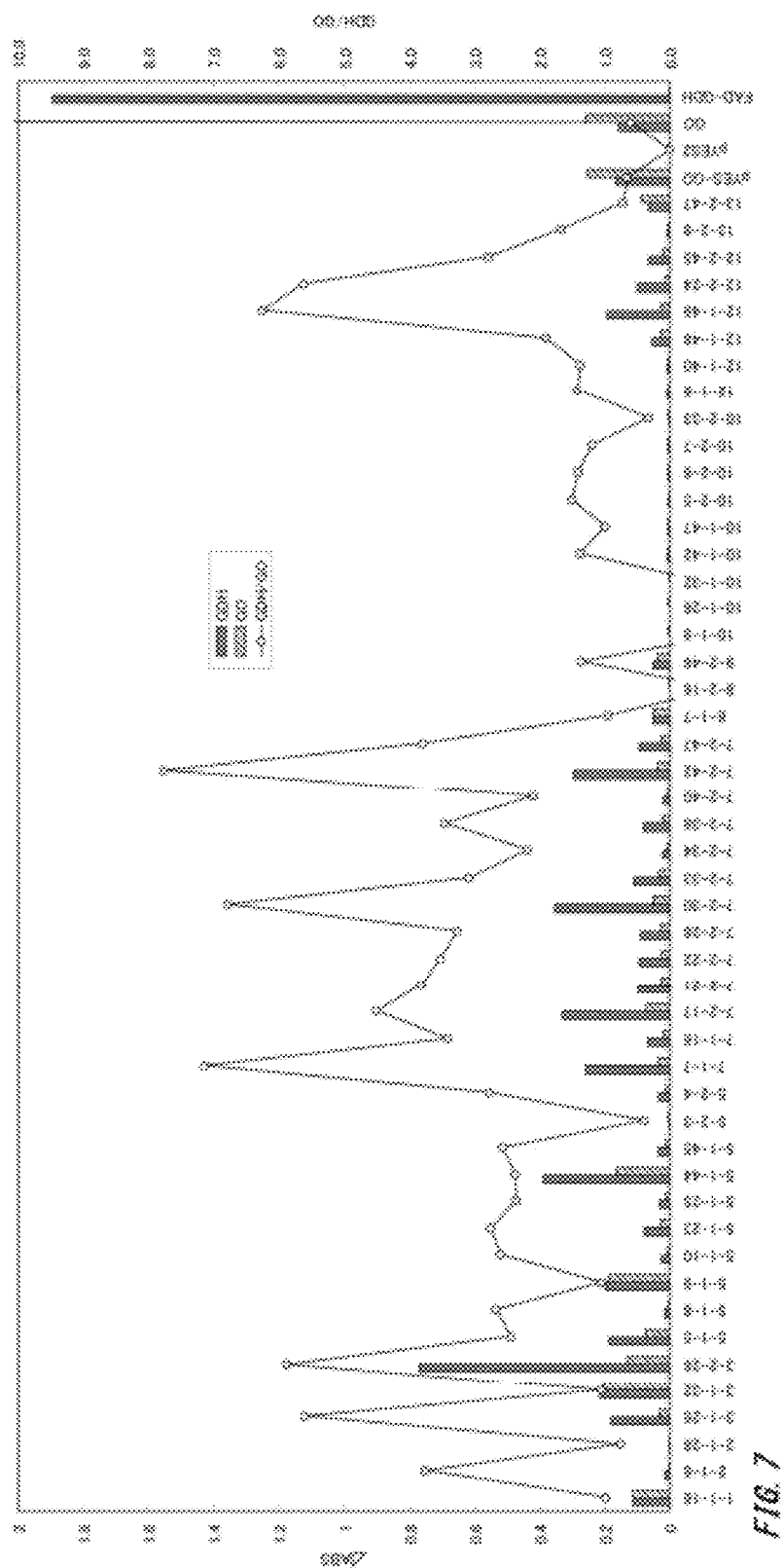
FIG. 7 is a graph showing results of observation of activities in liquid culture. GOH activity and GO activity of each mutated enzyme-transformant are shown with bars and a GDH activity/GO activity is shown with a line graph. pYES-GO denotes an unmutated transformant. In the graph, pYES-GO denotes a transformant obtained by transformation with unmutated enzyme, pYES2 denotes a transformant obtained by transformation with a plasmid before inserting a gene, GO denotes GO "Amano" 2 (Amano Enzyme Inc.), and FAD-GDH denotes GDH "Amano" 8 (Amano Enzyme Inc.), respectively.

20 μL of a supernatent was added to 200 μL of each reagent to be reacted at 37° C. Absorbances were measured after 10 minutes and 60 minutes from initiation of the reaction and GO activity and GDH activity were determined from the absorbance difference. A ratio of GDH activity and GO activity (GDH activity/GO activity) was calculated for each mutated enzyme-transformant to be compared (FIGS. 6 and 7). Note that transformants having an unmutated GO (expressed as pYES-GO in FIGS. 6 and 7), transformants obtained by transformation with a plasmid before inserting a GO gene (expressed as pYES-2 in FIGS. 6 and 7), GO "Amano" 2 (expressed as GO in FIGS. 6 and 7), and GDH "Amano" 8 (expressed as FAD-GDH in FIGS. 6 and 7) were used as samples to be compared (controls).

For mutated enzyme-transformants having significant changes observed in GDH/GO activity ratios, amino acid sequences at mutation introduction positions were confirmed (FIG. 8). Effective mutation was identified based on the results shown in FIGS. 6 to 8. Firstly, with respect to T132, a mutated enzyme-transformant having T132A (substitution to alanine from threonine) has a higher GDH/GO activity ratio than a mutated enzyme-transformant having T132V (substitution to valine from threonine) does, and thus, T132A was determined to be effective mutation. With respect to T353, although two mutations, T353A and T353H, were observed in the mutated enzyme-transformant (5-1-5), mutated enzyme-transformants (5-1-9, 5-1-44) which have T353A solely were present, and thus, the 5-1-5 strain was presumed to be a mixture of the two strains; therefore, T353A was determined to be effective mutation. With respect to D446, D446H was also determined to be effective mutation based on the same presumption. Furthermore, mutation, V582S, contained in the mutated enzyme-transformant 12-1-49 was also determined to be effective mutation. Note that amino acid sequences of GO, which have the above 4 mutations solely or in combination, and corresponding nucleotide sequences (gene sequences) are listed below.

Mutation: amino acid sequence: nucleotide sequence
T132A: SEQ ID NO: 7: SEQ ID NO: 22
T353A: SEQ ID NO: 8: SEQ ID NO: 23
D446H: SEQ ID NO: 9: SEQ ID NO: 24
V582S: SEQ ID NO: 10: SEQ ID NO: 25
T132A and T353A: SEQ ID NO: 11: SEQ ID NO: 26
T132A and D446H: SEQ ID NO: 12: SEQ ID NO: 27
T132A and V582S: SEQ ID NO: 13: SEQ ID NO: 28
T353A and D446H: SEQ ID NO: 14: SEQ ID NO: 29
T353A and V582S: SEQ ID NO: 15: SEQ ID NO: 30
D446H and V582S: SEQ ID NO: 16: SEQ ID NO: 31
T132A, T353A and D446H: SEQ ID NO: 17: SEQ ID NO: 32
T132A, T353A and V582S: SEQ ID NO: 18: SEQ ID NO: 33
T132A, D446H and V582S: SEQ ID NO: 19: SEQ ID NO: 34
T353A, D446H and V582S: SEQ ID NO: 20: SEQ ID NO: 35
T132A, T353A, D446H and V582S: SEQ ID NO: 21: SEQ ID NO: 36

4. Confirmation of Substrate Specificity of Mutant-Type GO

Substrate specificity as to GDH activity was examined on an enzyme having effective mutation (mutant-type GO).

<GDH Assay Reagents>
50 mM PIPES-NaOH (cont. 0.1% Triton X-100) pH 7.0 21 mL
10% substrate 5 mL
3 mmol/L PMS 1 mL
6.6 mmol/L NTB 3 mL 20 µL of a culture supernatent of each of the mutated enzyme-transformants (3-1-26, 3-2-26, 5-1-5, 5-1-9, 5-1-44, 7-1-7, 7-2-17, 7-2-30, 7-2-42, and 12-1-49) was added to 200 µL of each reagent to be reacted at 37° C. Absorbances were measured after 10 minutes and 60 minutes from initiation of the reaction and a GDH activity was determined from the absorbance difference. A GDH activity in the case of using each substrate was expressed as a ratio to the GDH activity (100%) in the case of using glucose as a substrate. Note that a transformant having an unmutated GO (expressed as pYES-GO in FIG. 9) was used as a sample to be compared (control).

Figure 9:
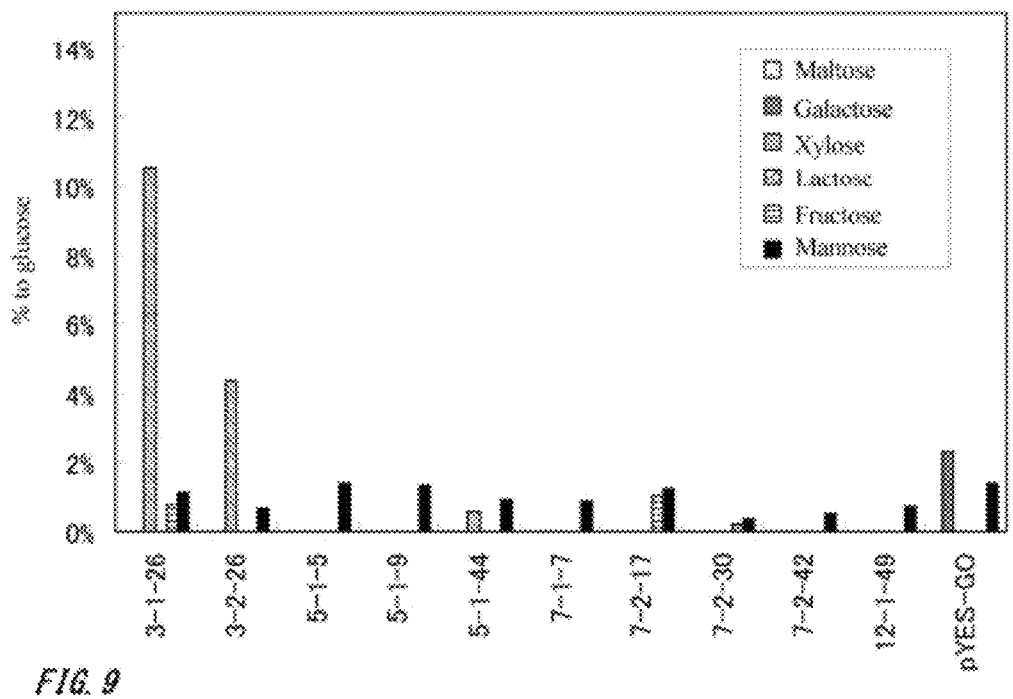
FIG. 9 is a graph showing substrate specificity of a mutant of GO. Reactivity to each substrate was calculated as a relative activity to glucose. pYES-GO denotes a transformant obtained by transformation with unmutated enzyme

As shown in FIG. 9, change in substrate specificity is observed in mutated enzyme-transformants. Mutated enzyme-transformants, 5-1-5, 5-1-9, 7-1-7, 7-2-17, 7-2-30, 7-2-42 and 12-1-49, do not show reactivity to xylose. Mutant-type GOs of these transformants are more excellent than existing FAD-GDH from the viewpoint that reactivity to xylose is not shown. Thus, by amino acid substitution, a problem specific to existing FAD-GDH while glucose dehydrogenating GO was solved. Note that since reactivity to xylose was generated due to mutation to T132, it was suggested that the site corresponding to the mutation could be involved with reactivity to xylose in FAD-GDH.

5. Confirmation of Effect of Mutation Combination

Effects were verified regarding combinations of gene mutations that were supposed to be effective mutations. In order to simplify later purification, a GO gene (GO-3) added with a histidine tag in the C terminal of an *Aspergillus niger* GO-1 strain-derived glucose oxidase gene was prepared by a PCR reaction, and inserted in pYES2 to construct a pYES-GO-3 plasmid.

(Composition of Reaction Solution)
10×LA buffer (TAKARA BIO INC.) 5 µL
2.5 mM dNTPs (TAKARA BIO INC.) 8 µL
25 mM MgCl$_2$ (TAKARA BIO INC.) 5 µL
Forward primer (50 µM) 1 µL
Reverse primer (50 µM) 1 µL
Template 1 µL
LA Taq (TAKARA BIO INC.) 0.5 µL
stH$_2$O 28.5 µL (Sequences of Primers)

```
Forward primer:
                                    (SEQ ID NO: 39)
GATCAGAAGCTTAAAAAAATGTCTACTCTCCTTGTGAGCTCG Reverse primer:
                                    (SEQ ID NO: 54)
GATCAGCTCGAGTCAATGGTGATGGTGATGATGCTGCATGGAAGCATAAT
C
```

(Reaction Conditions)

After reacting at 94° C. for 2 minutes, reaction cycles at 94° C. for 30 seconds, at 52° C. for 30 seconds, and at 72° C. for 2 minutes were repeated 35 times, thereafter reacting at 72° C. for 7 minutes and finally leaving at 4° C.

An amplified product after PCR was inserted into pYES2 to form a pYES-GO-3 plasmid, to confirm the sequence of the insert. From the viewpoint that no problem was found in the sequence, an operation for mutation was carried out to construct a plasmid having a multiply-mutated glucose oxidase based on the following synthesized oligonucleotides designed to be substituted to T132A, T353A, D446H, and V582S, respectively, and synthesized oligonucleotides complementary thereto, using the constructed pYES-GO-3 plasmid as a template, according to the attached protocol with a QuikChange Site-Directed Mutagensesis Kit (Stratagene co.).

```
GO-T132A-1:
                                    (SEQ ID NO: 55)
CTCGTCAACGGTGGCGCTTGGACTCGCCCCCAC

GO-T353A-1:
                                    (SEQ ID NO: 56)
CCTTCAGGACCAGACCGCTTCTACCGTCCGCTCAC

GO-D446H-1:
                                    (SEQ ID NO: 57)
GGAGTGGCCAGTTTCCATGTGTGGGATCTTCTGC

GO-V582S-1:
                                    (SEQ ID NO: 58)
CGCAAATGTCGTCCCATTCTATGACGGTCTTTTATGCCATGG
```

*Escherichia coli* DH5α was transformed with the plasmid after mutation introduction, and plasmid extraction was carried out to prepare a mutant library. *Saccharomyces cerevisiae* INVSc1 (Invitrogen Ltd.) was transformed with the obtained library, and the grown colony was subjected to liquid culture to confirm a GO activity and a GDH activity. Note that the manual of pYES2 was used as a reference for the experimental operations.

<GO Assay Reagents>
Phenol contained-phosphoric acid buffer solution 19 mL
10% glucose 5 mL
25 u/mL PO-3 5 mL
0.4 g/dL 4-A.A 1 mL <GDH Assay Reagents>
50 mM PIPES-NaOH (cont. 0.1% Triton X-100) pH 7.0 21 mL
10% glucose 5 mL
3 mmol/L PMS 3 mL
6.6 mmol/L NTB 1 mL 20 µL of a supernatent was added to 200 µL of each reagent to be reacted at 37° C. Absorbances were measured after 10 minutes and 30 minutes from initiation of the reaction and a GO activity and a GDH activity were determined from the absorbance difference. A ratio of a GDH activity and a GO activity (GDH activity/GO activity) was calculated for each mutated enzyme-transformant to be compared. Note that transformants having an unmutated GO into which a histidine tag was inserted (expressed as pYES-GO-3), transformants obtained by transformation with a plasmid before inserting a GO gene (expressed as pYES-2), GO "Amano" 2 (expressed as GO), and GDH "Amano" 8 (expressed as FAD-GDH) were used as samples to be compared (controls).

Results are shown in FIG. 11. Multiply-mutated enzymes of T132A and V582S (pYES-GO-M7), D446H and V582S (pYES-GO-M10), T132A, D446H and V582S (pYES-GO-M13) showed significant change in GDH/GO activity ratios as compared to each single-mutated enzyme or wild enzyme before introduction of mutation (pYES-GO-3).

6. Confirmation of Specific Activity and Substrate Specificity of Purified Multiply-Mutated Enzyme Then, for combinations of T132A, D446H and V582S which showed effects (T132A and D446H, T132A and V582S, D446H and V582S, T132A, D446H and V582S), transformants were subjected to liquid culture and purified using Ni-Sepharose to then examine a specific activity and substrate specificity. Note that the manual of pYES2 was used as a reference for the expression in liquid culture.

<GDH Assay Reagents>

50 mM PIPES-NaOH (cont. 0.1% Triton X-100) pH 7.0 21 mL

10% glucose 5 mL 3 mmol/L PMS 3 mL 6.6 mmol/L NTB 1 mL

20 μL of a purified enzyme solution or a standard enzyme solution was added to 200 μL of each reagent to be reacted at 37° C., and a gap of absorbances was determined after 5 minutes and 10 minutes from initiation of the reaction. An activity value was obtained from a calibration curve determined with a standard enzyme and a specific activity was calculated with a protein amount determined in the Bradford method. Results are shown in FIG. 12. The obtained specific activity of the purified enzyme was about 3 to 8 u/mg (protein).

Substrate specificity as to GDH activity was examined on the enzymes having effective mutation by using the purified enzymes thereof.

<GDH Assay Reagents>

50 mM PIPES-NaOH (cont. 0.1% Triton X-100) pH 7.0 21 mL

10% substrate 5 mL 3 mmol/L PMS 3 mL 6.6 mmol/L NTB 1 mL

20 μL of a culture supernatent of each of the mutated enzyme-transformants (M6, M7, M10, M13) was added to 200 μL of each reagent to be reacted at 37° C. Absorbances were measured after 5 minutes and 10 minutes from initiation of the reaction and a GDH activity was determined from the absorbance difference. A GDH activity in the case of using each substrate was expressed as a ratio to the GDH activity (100%) in the case of using glucose as a substrate. Note that GDH "Amano" 8 (expressed as FAD-GDH) was used as a control.

Figure 13:
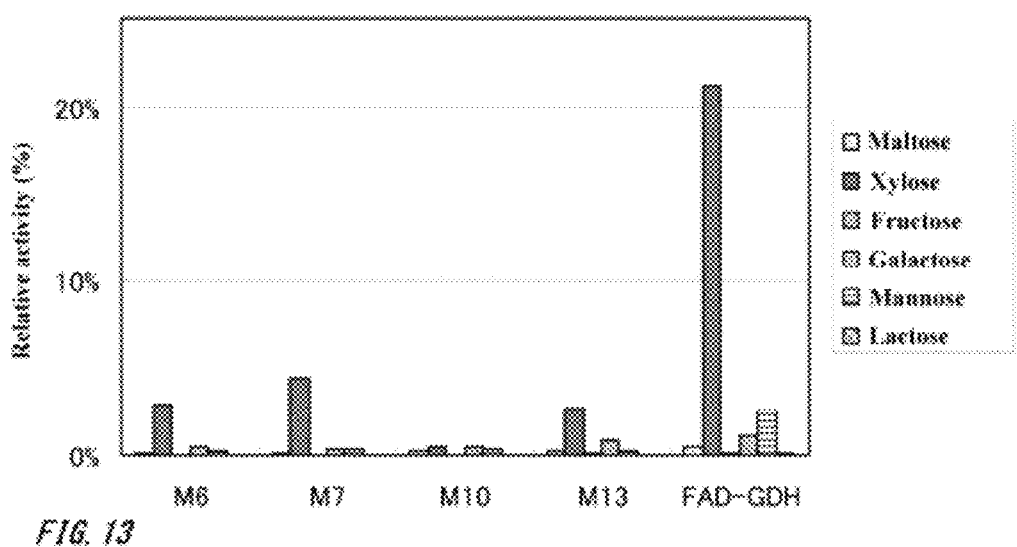
FIG. 13 shows substrate specificity of mutatedmutant-type enzymes produced from mutated enzyme-transfomant having effective combinations of mutation. Reactivities to maltose, xylose, fructose, galactose, mannose and lactose were compared.

Results are shown in FIG. 13. Change in substrate specificity was observed in mutated enzyme-transformants. Reactivity to xylose was not shown in D446H and V582S (pYES-GO-M10), in particular. Mutant-type GOs of the transformants are more excellent than existing FAD-GDH from the viewpoint that reactivity to xylose is not shown. Thus, by amino acid substitution, a problem specific to existing FAD-GDH was solved while making GO resemble GDH.

7. Study of Optimal Amino Acid for D446 and V582 Multiply-Mutated Enzyme

For the mutation combination of D446 and V582, in order that respective amino acids have optimal amino acid combination, an operation for mutation was carried out to construct a plasmid having a mutant glucose oxidase based on the synthesized oligonucleotides of SEQ ID NO: 47 and SEQ ID NO: 52 and the synthesized oligonucleotides thereto, using the pYES-GO-K-P-2 plasmid as a template, according to the attached protocol with a QuikChange Site-Directed Mutagensesis Kit (Stratagene co.). *Escherichia coli* DH5α was transformed with the plasmid after mutation introduction, and plasmid extraction was carried out to prepare a D446 and V582 multiply-mutated library. *Saccharomyces cerevisiae* INVSc1 (Invitrogen Ltd.) was transformed with the obtained library, and the obtained transformants were subjected to liquid culture using a 96-deep well, and those having improved GDH activities and improved ratios of GDH/GO activities were obtained. The combination of D446H and V582S was used as a control. Note that the manual of pYES2 was used as a reference for the experimental operations.

Results are shown in FIG. 14. GDH activities and ratios of GDH/GO activities were improved in combinations of D446H and V582R, D446H and V582L, D446H and V582P more than in the combination of D446H and V582S which is the original combination. Among these, the GO activity of the combination of D446H and V582P fell below the detection limit, and complete resemblance to GDH was achieved by amino acid substitution.

8. Study on Properties of D446H and V582P Multiply-Mutated Enzyme (1) Culture and Purification The manual of pYES2 was used as a reference for expression in liquid culture, and the transformant was inoculated to 100 mL of a medium (pH 5.4) containing 0.67% Yeast Nitrogen Base without Amino Acids (manufactured by Nippon Becton Dickinson Company, Ltd.) and 2% glucose, which was prepared in a 500 mL-shaking flask with a preservation plate, and subjected to pre-culture at 30° C., 140 rotations/min for 20 hours.

After completion of the pre-culture, bacterial bodies were recovered in centrifugation, and inoculated to 100 mL of a medium (pH 5.4) containing 0.67% Yeast Nitrogen Base without Amino Acids (manufactured by Nippon Becton Dickinson Company, Ltd.), 2% galactose, and 1% raffinose, which was prepared again to be OD660=0.4 in a 500 mL-shaking flask, and subjected to main culture at 30° C., 140 rotations/min for 5 hours.

After completion of the culture, desalting concentration was carried out with an ultrafiltration membrane (trade name MICROZA, molecular weight cut off 6000, manufactured by Asahi Kasei Corporation), and the desalted concentrated solution was adsorbed to a negative ion exchange resin (trade name HiTrap DEAE FF, manufactured by GE Healthcare Japan Corporation) column that was equilibrated with a 20 mM Phosphate buffer solution (pH 7.0), and washed with the above-mentioned buffer solution. After washing, a mutant-type GO was eluted using a NaCl-containing 30 mM MOPS buffer solution (pH 7.0), in the Liner gradient method having a NaCl concentration of 0 to 1.0M. A partially purified mutant-type GO (D446H and V582P multiply-mutated enzyme) was obtained in the purification method as described above.

(2) Confirmation of Substrate Specificity

Substrate specificity in GDH activity was examined on a partially purified mutant-type GO enzyme (D446H and V582P multiply-mutated enzyme).

<GDH Assay Reagents>

50 mM PIPES-NaOH (cont. 0.1% Triton X-100) pH 7.0 21 mL

10% substrate 5 mL 3 mmol/L PMS 3 mL 6.6 mmol/L NTB 1 mL

20 μL of a culture supernatent of a partially purified mutant-type GO enzyme (D446H and V582P multiply-mutated enzyme) was added to 200 μL of each reagent to be reacted at 37° C. Absorbances were measured after 10 minutes and 30 minutes from initiation of the reaction and a GDH activity was determined from the absorbance difference. A GDH activity in the case of using each substrate was expressed as a ratio to the GDH activity (100%) in the case of using glucose as a substrate. Note that GDH "Amano" 8 (expressed as FAD-GDH in FIGS. 6 and 7) was used as a control.

Figure 15:
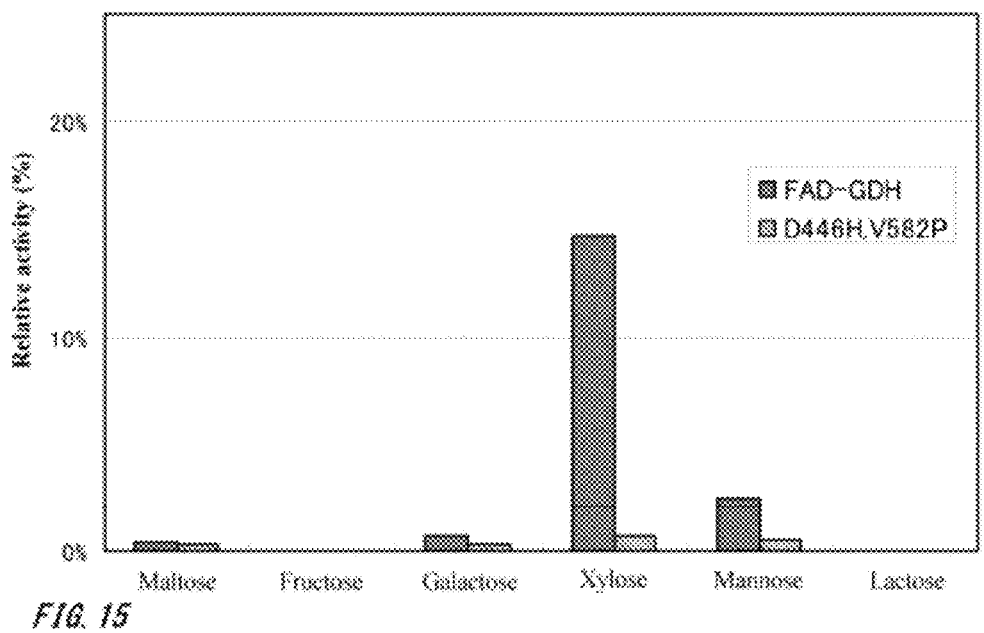
FIG. 15 shows substrate specificity of D446H and V582P multiply-mutated enzymes. Reactivities to maltose, xylose, fructose, galactose, mannose and lactose were compared to FAD-GDH (GDH "Amano" 8 (Amano Enzyme Inc.)).

Results are shown in FIG. 15. The partially purified mutant-type GO enzyme (D446H and V582P multiply-mutated enzyme) did not show reactivity to xylose and was far more excellent in substrate specificity as compared to GDH "Amano" 8.

INDUSTRIAL APPLICABILITY

The mutated GO provided by the present invention is effective to detection and quantitative determination of a glucose amount in a sample. On the other hand, the designing method and the preparation method of the present invention are used as means for obtaining GDH or GO having improved characteristics. Particularly, the methods are expected to be used as means for obtaining modified GO which resembles GDH or modified GDH which resembles GO.

The invention is not limited by the description of the embodiments and examples of the invention described above at all. Various modified embodiments are also included in the invention within the range that a person skilled in the art can easily conceive of, without deviating from the description of the scope of patent claims.

Contents of treatises, unexamined patent publications, and examined patent publications specified in this specification are all incorporated herewith by their references.

FREE TEXT OF SEQUENCE LISTING

SEQ ID NOs: 39 to 40, 54: explanation of artificial sequence: PCR primer

SEQ ID NOs: 41 to 53 and 55 to 58: explanation of artificial sequence: primer for mutation introduction

The invention claimed is:

1. An isolated mutated microorganism-derived glucose oxidase, comprising an amino acid sequence wherein one or at least two amino acids selected from the group consisting of (1) to (13) are substituted with another amino acid relative to an amino acid sequence of an unmutated microorganism-derived glucose oxidase:

(1) the amino acid corresponding to the amino acid at position 115 of the amino acid sequence of SEQ ID NO: 1;

(2) the amino acid corresponding to the amino acid at position 131 of the amino acid sequence of SEQ ID NO: 1;

(3) the amino acid corresponding to the amino acid at position 132 of the amino acid sequence of SEQ ID NO: 1;

(4) the amino acid corresponding to the amino acid at position 193 of the amino acid sequence of SEQ ID NO: 1;

(5) the amino acid corresponding to the amino acid at position 353 of the amino acid sequence of SEQ ID NO: 1;

(6) the amino acid corresponding to the amino acid at position 436 of the amino acid sequence of SEQ ID NO: 1;

147

(7) the amino acid corresponding to the amino acid at position 446 of the amino acid sequence of SEQ ID NO: 1;
(8) the amino acid corresponding to the amino acid at position 472 of the amino acid sequence of SEQ ID NO: 1;
(9) the amino acid corresponding to the amino acid at position 511 of the amino acid sequence of SEQ ID NO: 1;
(10) the amino acid corresponding to the amino acid at position 535 of the amino acid sequence of SEQ ID NO: 1;
(11) the amino acid corresponding to the amino acid at position 537 of the amino acid sequence of SEQ ID NO: 1;
(12) the amino acid corresponding to the amino acid at position 582 of the amino acid sequence of SEQ ID NO: 1; and
(13) the amino acid corresponding to the amino acid at position 583 of the amino acid sequence of SEQ ID NO: 1
wherein the unmutated microorganism-derived glucose oxidase has at least 90% identity to SEQ ID NO: 1;
wherein the isolated mutated enzyme has higher glucose dehydrogenase activity relative to the unmutated microorganism-derived glucose oxidase; and
wherein the amino acid (7) is aspartic acid when the amino acid (7) is not substituted and the amino acid (7) is histidine when substituted.

2. The isolated mutated microorganism-derived glucose oxidase according to claim 1, wherein the substituted amino acid is the amino acid (3), the amino acid (5), the amino acid (7) or the amino acid (12), or a combination of at least two amino acids selected from these amino acids.

3. The isolated mutated microorganism-derived glucose oxidase according to claim 2, wherein the amino acid after substitution is: alanine for the amino acid (3); alanine for the amino acid (5); histidine for the amino acid (7); and serine, arginine, leucine or proline for the amino acid (12).

4. The isolated mutated microorganism-derived glucose oxidase according to claim 2, wherein the substituted amino acid is the amino acid (3), the amino acid (7) or the amino acid (12), or a combination of at least two amino acids selected from these amino acids.

5. The isolated mutated microorganism-derived glucose oxidase according to claim 4, wherein the amino acid after substitution is: alanine for the amino acid (3); histidine for the amino acid (7); and serine, arginine, leucine or proline for the amino acid (12).

6. The isolated mutated microorganism-derived glucose oxidase according to claim 4, wherein the substituted amino acids are the amino acid (7) and the amino acid (12).

7. The isolated mutated microorganism-derived glucose oxidase according to claim 6, wherein the amino acid after substitution is: histidine for the amino acid (7); and serine, arginine, leucine or proline for the amino acid (12).

8. The isolated mutated microorganism-derived glucose oxidase according to claim 1, comprising any one of the amino acid sequences of SEQ ID NOs: 7 to 21 and 59 to 61.

9. An isolated gene coding for the isolated mutated microorganism-derived glucose oxidase according to claim 1.

10. The isolated gene according to claim 9, comprising any one of the nucleotide sequences of SEQ ID NOs: 22 to 36 and 62 to 64.

11. A recombinant DNA, comprising the isolated gene according to claim 9.

148

12. A microorganism having the recombinant DNA according to claim 11.

13. A glucose measurement method, wherein glucose in a sample is measured using the isolated mutated microorganism-derived glucose oxidase according to claim 1.

14. A glucose measuring reagent, comprising the isolated mutated microorganism-derived glucose oxidase according to claim 1.

15. A glucose measuring kit, comprising the glucose measuring reagent according to claim 14.

16. A method, wherein a glucose amount in an industrial product or a raw material thereof is reduced by using the isolated mutated microorganism-derived glucose oxidase according to claim 1.

17. An enzyme preparation, comprising the isolated mutated microorganism-derived glucose oxidase according to claim 1.

18. The isolated mutated microorganism-derived glucose oxidase of claim 1, wherein the unmutated microorganism-derived glucose oxidase has at least 95% identity to SEQ ID NO: 1.

19. The isolated mutated microorganism-derived glucose oxidase of claim 1, wherein the unmutated microorganism-derived glucose oxidase has at least 98% identity to SEQ ID NO: 1.

20. The isolated mutated microorganism-derived glucose oxidase of claim 1,
wherein the unmutated microorganism-derived glucose oxidase is the amino acid sequence of SEQ ID NO: 1.

21. An isolated mutated microorganism-derived glucose oxidase, comprising an amino acid sequence wherein one or at least two amino acids selected from the group consisting of (1) to (13) are substituted with another amino acid relative to an amino acid sequence of an unmutated microorganism-derived glucose oxidase:
(1) the amino acid corresponding to the amino acid at position 115 of the amino acid sequence of SEQ ID NO: 1;
(2) the amino acid corresponding to the amino acid at position 131 of the amino acid sequence of SEQ ID NO: 1;
(3) the amino acid corresponding to the amino acid at position 132 of the amino acid sequence of SEQ ID NO: 1;
(4) the amino acid corresponding to the amino acid at position 193 of the amino acid sequence of SEQ ID NO: 1;
(5) the amino acid corresponding to the amino acid at position 353 of the amino acid sequence of SEQ ID NO: 1;
(6) the amino acid corresponding to the amino acid at position 436 of the amino acid sequence of SEQ ID NO: 1;
(7) the amino acid corresponding to the amino acid at position 446 of the amino acid sequence of SEQ ID NO: 1;
(8) the amino acid corresponding to the amino acid at position 472 of the amino acid sequence of SEQ ID NO: 1;
(9) the amino acid corresponding to the amino acid at position 511 of the amino acid sequence of SEQ ID NO: 1;
(10) the amino acid corresponding to the amino acid at position 535 of the amino acid sequence of SEQ ID NO: 1;

(11) the amino acid corresponding to the amino acid at position 537 of the amino acid sequence of SEQ ID NO: 1;
(12) the amino acid corresponding to the amino acid at position 582 of the amino acid sequence of SEQ ID NO: 1; and
(13) the amino acid corresponding to the amino acid at position 583 of the amino acid sequence of SEQ ID NO: 1 wherein the isolated mutated enzyme has higher glucose dehydrogenase activity relative to the unmutated microorganism-derived glucose oxidase;

wherein the unmutated microorganism-derived glucose oxidase is the amino acid sequence of SEQ ID NO: 1.

* * * * *